US006100263A

United States Patent [19]

Bayer et al.

[11] Patent Number: 6,100,263

[45] Date of Patent: Aug. 8, 2000

[54] PHENYLACETIC ACID DERIVATIVES, PREPARATION THEREOF AND INTERMEDIATES THEREFOR, AND COMPOSITIONS CONTAINING THEM

[75] Inventors: Herbert Bayer; Hubert Sauter, both of Mannheim; Ruth Müller, Andernach; Wassilios Grammenos; Albrecht Harreus, both of Ludwigshafen; Reinhard Kirstgen, Neustadt; Franz Röhl, Schifferstadt; Eberhard Ammermann, Heppenheim; Gisela Lorenz, Hambach, all of Germany

[73] Assignee: BASF Aktiengesellschaft, Ludwigshafen, Germany

[21] Appl. No.: 09/334,385

[22] Filed: Jun. 16, 1999

Related U.S. Application Data

[62] Division of application No. 09/015,692, Jan. 29, 1998, Pat. No. 5,981,581, which is a division of application No. 08/687,480, Aug. 5, 1996, Pat. No. 5,889,059, which is a continuation of application No. PCT/EP95/00007, Jan. 3, 1995.

[30] Foreign Application Priority Data

| | | | |
|---|---|---|---|
| Feb. 4, 1994 | [DE] | Germany | 44 03 448 |
| Jun. 17, 1994 | [DE] | Germany | 44 21 182 |

[51] Int. Cl.$^7$ .......... A01N 43/54; A01N 43/40; C07D 213/56; C07D 239/26

[52] U.S. Cl. .......... 514/241; 514/256; 514/357; 514/365; 514/374; 514/378; 514/400; 514/401; 514/471; 544/215; 544/335; 546/337; 548/204; 548/236; 548/247; 548/337.1; 548/375.1; 549/426

[58] Field of Search .......... 558/3, 7; 564/74, 564/164, 165; 514/599, 620, 241, 256, 357, 365, 374, 378, 400, 401, 471; 544/215, 335; 546/337; 548/204, 236, 247, 337.1, 375.1; 549/426

[56] References Cited

U.S. PATENT DOCUMENTS

| | | | |
|---|---|---|---|
| 5,194,662 | 3/1993 | Brandt et al. | 560/35 |
| 5,221,691 | 6/1993 | Clough et al. | 514/619 |
| 5,393,782 | 2/1995 | Wingert et al. | 514/599 |
| 5,756,426 | 5/1998 | Ziegler et al. | 504/599 |
| 5,981,581 | 11/1999 | Bayer et al. | 514/522 |

FOREIGN PATENT DOCUMENTS

| | | |
|---|---|---|
| 2104806 | 3/1994 | Canada . |
| 398692 | 11/1990 | European Pat. Off. . |
| 567828 | 4/1992 | European Pat. Off. . |
| 513580 | 11/1992 | European Pat. Off. . |
| 528682 | 2/1993 | European Pat. Off. . |
| 9007493 | 7/1990 | WIPO . |
| 9426700 | 11/1994 | WIPO . |
| 9518789 | 7/1995 | WIPO . |

OTHER PUBLICATIONS

*Pat. Abstr. of Japan,* vol. 17, No. 644 (C–1134) (English abstract of JP–A 05/201,946, Aug. 10, 1993).

*Pat. Abstr. of Japan,* vol. 18, No. 19 (C–1152) (English abstract of JP–A 05/255,012, May 10, 1993).

*Pat. Abstr. of Japan,* vol. 18, No. 93 (C–1166) (English abstract of JP–A 05/294,948, Sep. 11, 1993).

*Primary Examiner*—Richard L. Raymond
*Attorney, Agent, or Firm*—Keil & Weinkauf

[57] ABSTRACT

Phenylacetic acid derivatives of the formula I

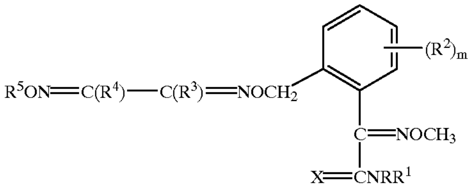

where the substituents and the index have the following meanings:

X is oxygen or sulfur;

R is hydrogen or alkyl;

$R^1$ is hydrogen or alkyl;

$R^2$ is cyano, nitro, trifluoromethyl, halogen, alkyl or alkoxy;

m is 0, 1 or 2, it being possible for the $R^2$ radicals to be different if m is 2;

and their salts, processes and intermediates for their preparation, and their use are described.

21 Claims, No Drawings

PHENYLACETIC ACID DERIVATIVES, PREPARATION THEREOF AND INTERMEDIATES THEREFOR, AND COMPOSITIONS CONTAINING THEM

This is a Divisional Application of application Ser. No. 09/015,692, filed Jan. 29, 1998 (U.S. Pat. No. 5,981,581), which is a Divisional Application of application Ser. No. 08/687,480, filed on Aug. 05, 1996 (U.S. Pat. No. 5,889, 059), which is a continuation of PCT/EP 95/00,007, filed on Jan. 03, 1995.

The present invention relates to phenylacetic acid derivatives of the formula I (I)

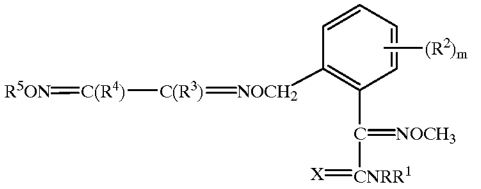

where the substituents and the index have the following meanings:

X is oxygen or sulfur;

R is hydrogen and $C_1$–$C_4$-alkyl;

$R^1$ is hydrogen and $C_1$–$C_4$-alkyl;

$R^2$ is cyano, nitro, trifluoromethyl, halogen, $C_1$–$C_4$-alkyl and $C_1$–$C_4$-alkoxy;

m is 0, 1 or 2, it being possible for the $R^2$ radicals to be different if m is 2;

$R^3$ is hydrogen, cyano, nitro, hydroxyl, amino, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino or di-$C_1$–$C_4$-alkylamino;

$R^4$ is hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N—$C_2$–$C_6$-alkenyl-N—$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N—$C_2$–$C_6$-alkynyl-N—$C_1$–$C_6$-alkylamino, it being possible for the hydrocarbon radicals of these groups to be partly or completely halogenated or to carry one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkoxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals in turn to be partly or completely halogenated and/or to carry one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and C(=NOR$^6$)—$A_n$—$R^7$;

$C_3$–$C_6$-cycloalkyl, $C_3$–$C_6$-cycloalkoxy, $C_3$–$C_6$-cycloalkylthio, $C_3$–$C_6$-cycloalkylamino, N—$C_3$–$C_6$-cycloalkyl-N—$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N—$C_3$–$C_6$-cycloalkenyl-N—$C_1$–$C_6$-alkylamino, heterocyclyl, heterocyclyloxy, heterocyclylthio, heterocyclylamino, N-heterocyclyl-N—-$C_1$–$C_6$-alkylamino, aryl, aryloxy, arylthio, arylamino, N-aryl-N—$C_1$–$C_6$-alkylamino, hetaryl, hetaryloxy, hetarylthio, hetarylamino, N-hetaryl-N—$C_1$–$C_6$-alkylamino, it being possible for the cyclic radicals to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

$R^5$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkoxy, heterocyclyl, heterocyclyloxy, benzyl, benzyloxy, aryl, aryloxy, arylthio, hetaryl, hetaryloxy and hetarylthio, it being possible for the cyclic groups in turn to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or C(=NOR$^6$)—$A_n$—$R^7$;

aryl, arylcarbonyl, arylsulfonyl, hetaryl, hetarylcarbonyl or hetarylsulfonyl, it being possible for these radicals to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or C(═NOR$^6$)—$A_n$—R$^7$; where A is oxygen, sulfur or nitrogen and where the nitrogen carries hydrogen or $C_1$–$C_6$-alkyl;

n is 0 or 1;

R$^6$ is hydrogen or $C_1$–$C_6$-alkyl and

R$^7$ is hydrogen or $C_1$–$C_6$-alkyl, and their salts.

The invention additionally relates to processes and intermediates for preparing these compounds and compositions containing them for controlling animal pests and harmful fungi.

Phenylacetic acid derivatives for pest control are disclosed in the literature (EP-A 398 692, EP-A 477 631, EP-A 513 580, EP-A 567 828, EP-A 528 682, EP-A 463 488, WO-A 92/13,830).

It is an object of the present invention to provide novel compounds having improved action.

We have found that this object is achieved by the phenylacetic acid derivatives I defined at the outset. We have additionally found processes and intermediates for their preparation and compositions containing them for controlling animal pests and harmful fungi and their use within this context.

The compounds I are obtainable in various ways by processes known per se in the literature.

Fundamentally, it is insignificant in the synthesis of the compounds I whether the group $^{\ominus}$C(NOCH$_3$)—CONRR$^1$ or the group —CH$_2$ON═C(R$^3$)—C(R$^4$)═NOR$^5$ is constructed first.

The construction of the group —C(NOCH$_3$)—CONRR$^1$ is disclosed, for example, in the literature cited at the outset.

The manner of the synthesis of the —CH$_2$ON═C(R$^3$)—C(R$^4$)═NOR$^5$ side chain essentially depends on the nature of the substituents R$^3$ and R$^4$.

1. In the case in which R$^3$ and R$^4$ are not halogen, the construction of the group —CH$_2$ON-═C(R$^3$)—C(R$^4$)═NOR$^5$ in general proceeds by reacting a benzyl derivative of the formula II with a hydroxyimine of the formula III.

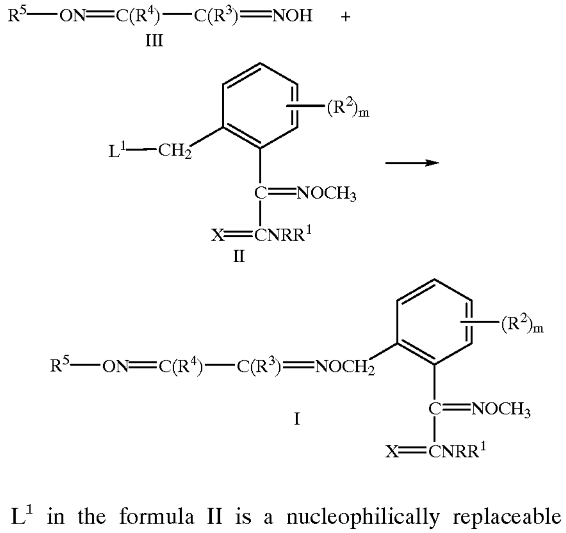

L$^1$ in the formula II is a nucleophilically replaceable leaving group, eg. halogen or sulfonate groups, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate or triethylamine according to the methods described in Houben-Weyl, Vol. E 14b, p. 370 ff and Houben-Weyl, Vol. 10/1 p. 1189 ff.

The hydroxyimine III required is obtained, for example, by reaction of a corresponding dihydroxyimine IV with a nucleophilically substituted reagent VI

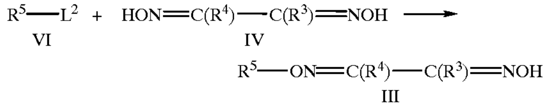

L$^2$ in the formula VI is a nucleophilically replaceable leaving group, eg. halogen or sulfonate groups, preferably chlorine, bromine, iodine, mesylate, tosylate or triflate.

The reaction is carried out in a manner known per se in an inert organic solvent in the presence of a base, eg. potassium carbonate, potassium hydroxide, sodium hydride, pyridine or triethylamine according to the methods described in Houben-Weyl, Vol. E 14b, p. 307 ff, p. 370 ff and p. 385 ff; Houben-Weyl, Vol. 10/4, p. 55 ff, p. 180 ff and p. 217 ff; Houben-Weyl, Vol. E5, p. 780 ff.

1.1 Alternatively, the compounds I can also be obtained by converting the benzyl derivative II first to a corresponding benzyl oxime of the formula V using the dihydroxyimine IV, V then being reacted with the nucleophilically substituted reagent VI to give I.

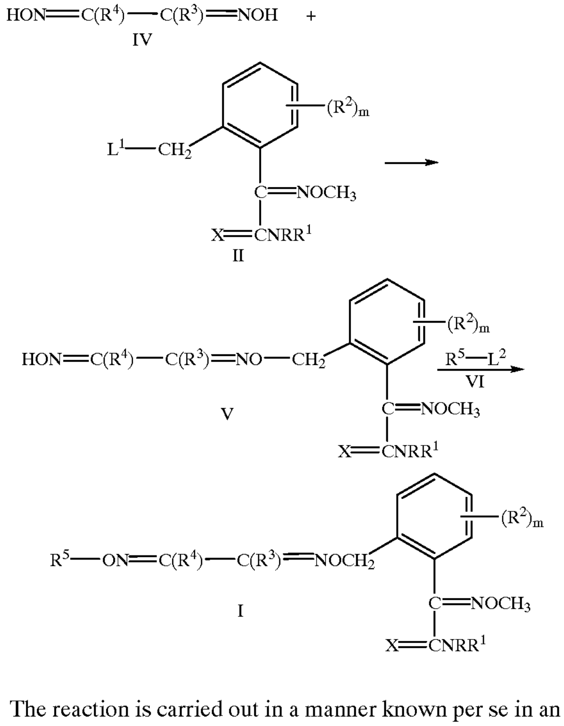

The reaction is carried out in a manner known per se in an inert organic solvent in the presence of a base, eg. potassium carbonate, potassium hydroxide, sodium hydride, pyridine or triethylamine according to the methods described in Houben-Weyl, Vol. 10/1, p. 1189 ff; Houben-Weyl, Vol. E 14b, p. 307 ff, p. 370 ff and p. 385 ff; Houben-Weyl, Vol. 10/4, p. 55 ff, p. 180 ff and p. 217 ff; Houben-Weyl, Vol. E5, p. 780 ff.

1.2 In a similar manner, it is also possible to prepare the required hydroxyimine of the formula III from a carbonylhydroxyimine VII by reaction with a hydroxylamine IXa or its salt IXb.

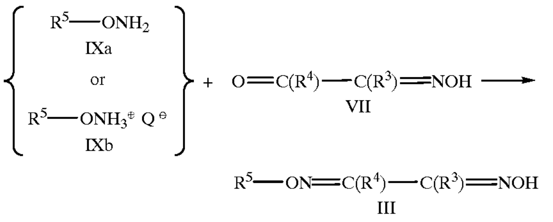
IXa
or
IXb
VII
III $Q^{\ominus}$ in the formula IXb is the anion of an acid, in particular of an inorganic acid, eg. halide such as chloride.

The reaction is carried out in a manner known per se in an inert organic solvent according to the methods described in EP-A 513 580; Houben-Weyl, Volume 10/4, p. 73 ff; Houben-Weyl, Vol. E14b, p. 369 ff and p. 385 ff.

1.3 Alternatively, the compounds I can also be obtained by converting the benzyl derivative II first to a corresponding benzylketoxyimine of the formula VIII using the carbonylhydroxyimine VII, VIII then being reacted with the hydroxylamine IXa or its salt IXb to give I.

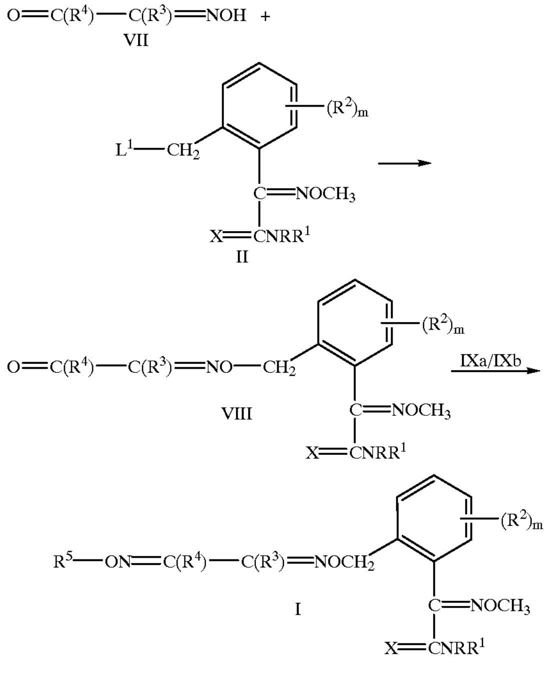

VII
II
VIII
I

The reaction is carried out in a manner known per se in an inert organic solvent according to the methods described in Houben-Weyl, Vol. E14b, p. 369 ff; Houben-Weyl, Vol. 10/1, p. 1189 ff and Houben-Weyl, Vol. 10/4, p. 73 ff or EP-A 513 580.

1.4 Another possibility for preparing the compounds I is the reaction of the benzyl derivative II with N-hydroxyphthalimide and subsequent hydrazinolysis to the benzylhydroxylamine IIa and the further reaction of IIa with a carbonyl compound X.

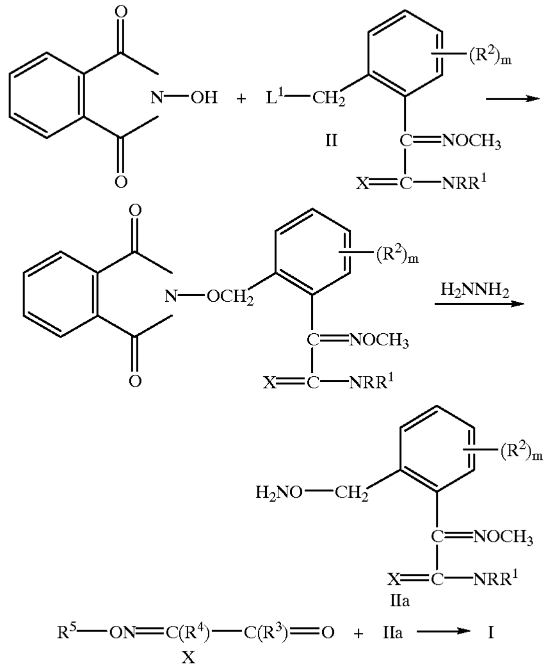

II
IIa
X
I

The reaction is carried out in a manner known per se in an inert organic solvent according to the methods described in EP-A 463 488 and German Appl. No. 42 28 867.3.

The carbonyl compound X required is obtained, for example, by reaction of a corresponding hydroxyiminocarbonyl VIIa with a nucleophilically substituted reagent VI

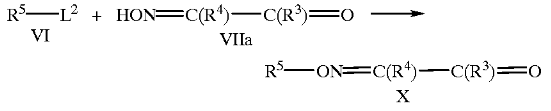
VI
VIIa
X or by reaction of a corresponding dicarbonyl XI with a hydroxylamine IXa or its salt IXb

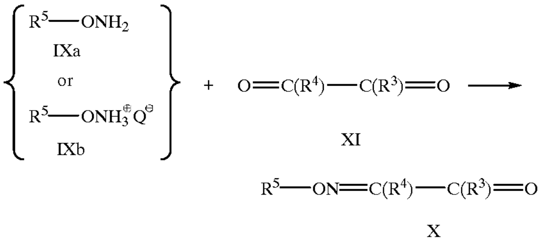
IXa
or
IXb
XI
X

The reactions are carried out in a manner known per se in an inert organic solvent according to the methods described in EP-A 513 580, Houben-Weyl, Vol. 10/4, p. 55 ff, p. 73 ff, p. 180 ff and p. 217 ff, Houben-Weyl, Vol. E14b, p. 307 ff and 369 ff, Houben-Weyl, Vol. E5, p. 780 ff.

1.5 Correspondingly, the compounds I can also be obtained by converting the benzylhydroxylamine IIa first to the corresponding benzyloxyimine of the formula V using the hydroxyiminocarbonyl VIIa, V then being reacted with the nucleophilically substituted reagent VI to give I as described above.

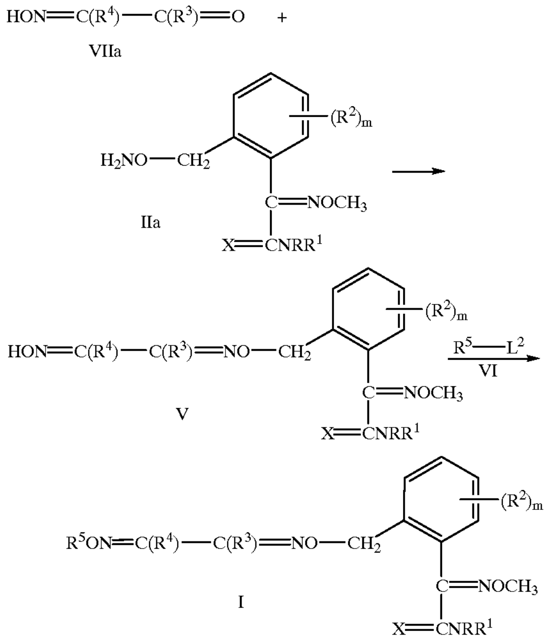

VIIa, IIa, V, I 1.6 In a similar manner, the compounds I can also be prepared by converting the benzylhydroxylamine IIa first to the benzyloxyimine VIII using the dicarbonyl of the formula XI and then reacting VIII with the hydroxylamine IXa or its salt IXb to give I as described above.

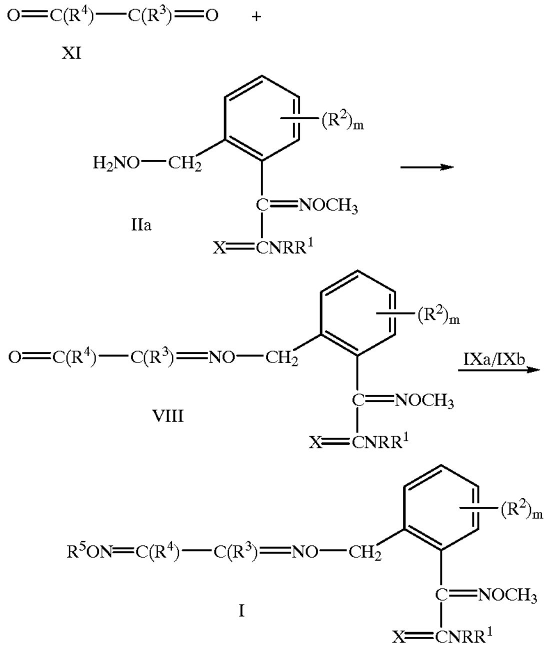

XI, IIa, VIII, I

2. Compounds in which $R^3$ and/or $R^4$ are a halogen atom are obtained by methods known per se from the corresponding precursors in which the radical concerned is a hydroxyl group (cf. Houben-Weyl, Vol. E5, p. 631; J. Org. Chem. 36 (1971), 233; J. Org. Chem. 57 (1992), 3245). Preferably, the corresponding reactions to give the halogen derivative are performed in stages I and VIII.

3. Compounds in which $R^3$ and/or $R^4$ are bonded to the structure via an O, S or N atom are obtained by methods known per se from the corresponding precursors in which the radical concerned is a halogen atom (cf. Houben-Weyl, Vol. E5, p. 826 ff and 1280 ff, J. Org. Chem. 36 (1971), 233, J. Org. Chem. 46 (1981), 3623). Preferably, the corresponding conversions of the halogen derivative are performed in stages I and VIII.

4. Compounds in which $R^3$ and/or $R^4$ are bonded to the structure via an oxygen atom are in some cases also obtained by methods known per se from the corresponding precursors in which the radical concerned is a hydroxyl group (cf. Houben-Weyl, Vol. E5, p. 826–829, Aust. J. Chem. 27 (1974), 1341–9). Preferably, the corresponding reactions to give the alkoxy derivatives are performed in stages I and VIII.

5. Compounds in which $R^3$ is not halogen are preferably obtained by first converting a compound X to the corresponding benzoic acid XIII according to the methods described in EP-A 493 711 using a lactone XII and converting XIII via the corresponding halides to the cyanocarboxylic acids XIV, which are then converted by way of the Pinner reaction (Angew. Chem. 94 (1982), 1) to the α-keto esters XV. The corresponding carboxamides, which are subsequently converted to the compounds I, are obtained from the derivatives XV by amidation.

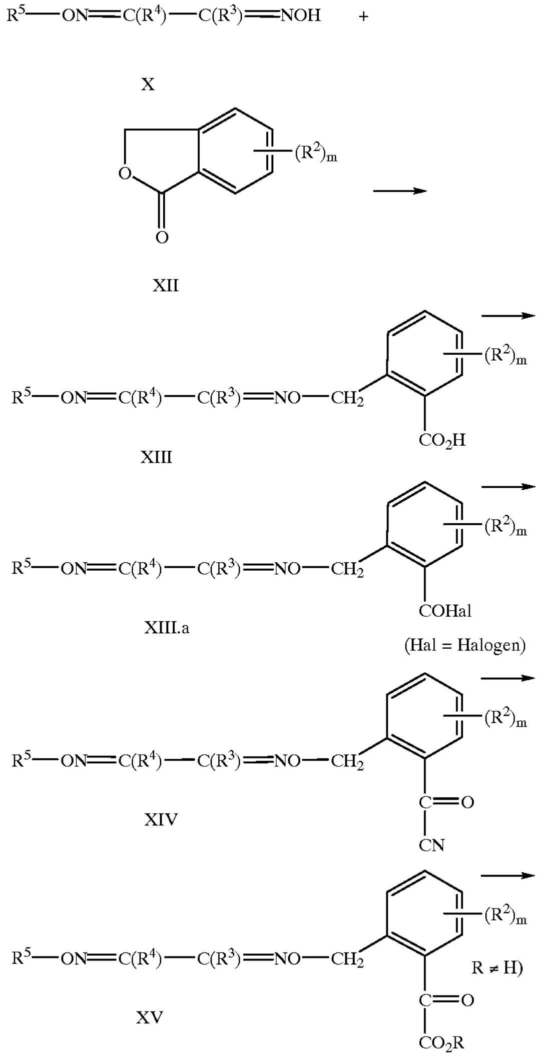

X, XII, XIII, XIII.a, XIV, XV

-continued

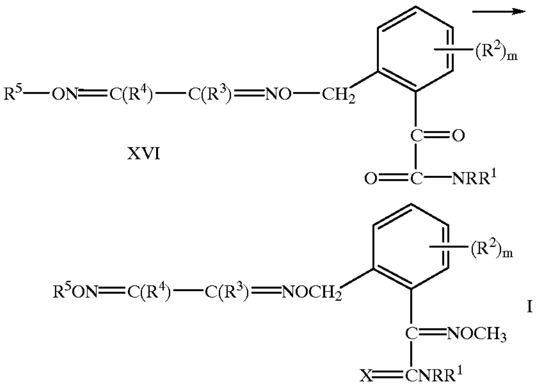

XVI

I

6. The compounds XVI in which R is hydrogen can also be obtained directly from the carbonyl halides by reaction with isocyanates and subsequent hydrolysis by modifying the process described in 5. (EP 547 825).

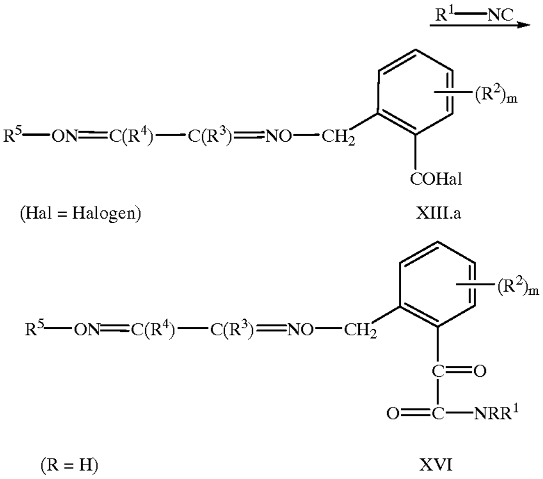

(Hal = Halogen) XIII.a (R = H) XVI

7. In another variant, compounds XVI are obtained by converting an ortho halogen compound, after metallation with oxalyl chloride, to the corresponding keto acid chloride, which is subsequently converted with an amine to the corresponding amide XVI (cf. J. Org. Chem. 46 (1981), 46, 212 ff; DE-A 40 42 280; Houben-Weyl, Vol. E5, p. 972 ff).

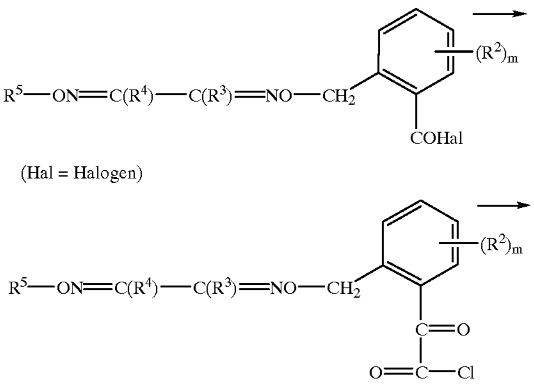

(Hal = Halogen)

-continued

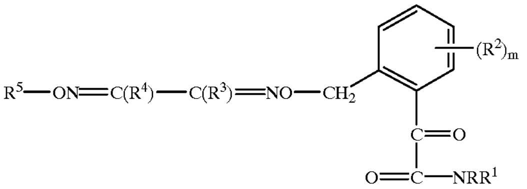

8. In another variant, the compounds I in which X is oxygen are obtained, starting from the keto esters XV, by first converting the keto function to the oxime ether and converting the oxime ester thus obtained to I using an appropriate amine (Houben-Weyl, Vol. E5, p. 941 ff).

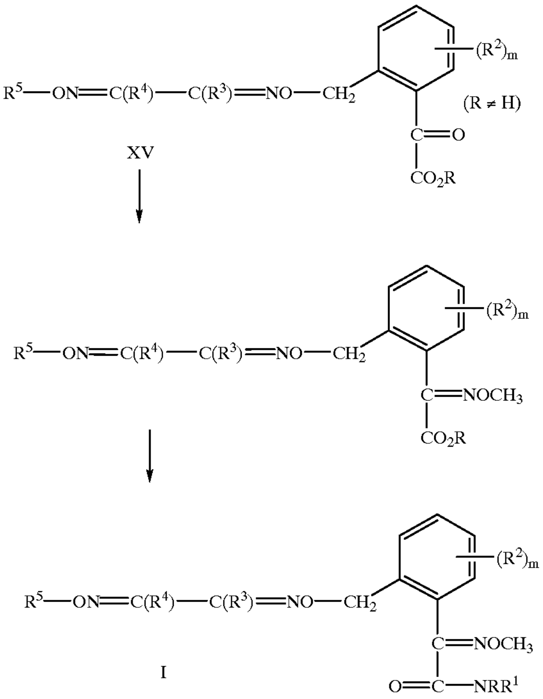

XV (R ≠ H)

I

9. The compounds I in which X is sulfur are obtained from the corresponding amides I by reaction with a sulfurizing reagent (eg. phosphorus sulfide or Zawesson's reagent; cf. Houben-Weyl, Vol. IX, 764 ff).

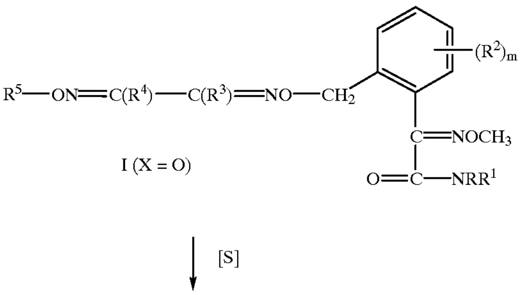

I (X = O)

-continued

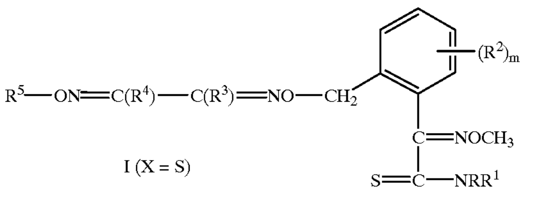

I (X = S)

The compounds II are known (EP-A 477 631, EP-A 463 488) or can be prepared by the methods described there.

On account of their C═C and C═N double bonds, the compounds I can be obtained during preparation as E/Z isomer mixtures which can be separated into the individual compounds in a customary manner, eg. by crystallization or chromatography.

If isomer mixtures are obtained during the synthesis, in general, however, a separation is not absolutely necessary, as the individual isomers can in some cases be converted to one another during preparation for application or during application (eg. under the action of light, acid or base). Corresponding conversions can also take place after application, for example during the treatment of plants in the treated plant or in the harmful fungus or animal pest to be controlled.

With reference to the C═$NOCH_3$ double bond, the cis isomers of the compounds I are preferred with respect to their activity (configuration based on the —$OCH_3$ group in relation to the —$CXNRR^1$ group).

With reference to the —$C(R^3)$═$NOCH_2$— double bond, the Z isomers of the compounds I are preferred with respect to their activity (configuration based on the radical $R^3$ in relation to the —$OCH_2$— group).

In the definitions of the compounds I given at the outset, collective terms were used which are generally representative of the following groups:

halogen: fluorine, chlorine, bromine and iodine;

alkyl: straight-chain or branched alkyl groups having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkylamino: an amino group which carries a straight-chain or branched alkyl group having 1 to 6 carbon atoms as mentioned above;

dialkylamino: an amino group which carries two straight-chain or branched alkyl groups which are independent of one another and each have 1 to 6 carbon atoms as mentioned above;

alkylcarbonyl: straight-chain or branched alkyl groups having 1 to 10 carbon atoms, which are bonded to the structure via a carbonyl group (—CO—);

alkylsulfonyl: straight-chain or branched alkyl groups having 1 to 6 or 10 carbon atoms, which are bonded to the structure via a sulfonyl group (—S(═O)$_2$—);

alkylsulfoxyl: straight-chain or branched alkyl groups having 1 to 6 carbon atoms, which are bonded to the structure via a sulfoxyl group (—S(═O)—);

alkylaminocarbonyl: alkylamino groups having 1 to 6 carbon atoms as mentioned above, which are bonded to the structure via a carbonyl group (—CO—);

dialkylaminocarbonyl: dialkylamino groups in each case having 1 to 6 carbon atoms per alkyl radical as mentioned above, which are bonded to the structure via a carbonyl group (—CO—);

alkylaminothiocarbonyl: alkylamino groups having 1 to 6 carbon atoms as mentioned above, which are bonded to the structure via a thiocarbonyl group (—CS—);

dialkylaminothiocarbonyl: dialkylamino groups in each case having 1 to 6 carbon atoms per alkyl radical as mentioned above, which are bonded to the structure via a thiocarbonyl group (—CS—);

haloalkyl: straight-chain or branched alkyl groups having 1 to 6 carbon atoms, it being possible for the hydrogen atoms in these groups to be partly or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 or 6 carbon atoms as mentioned above, which are bonded to the structure via an oxygen atom (—O—), eg. $C_1$–$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkoxycarbonyl: straight-chain or branched alkyl groups having 1 to 6 carbon atoms, which are bonded to the structure via an oxycarbonyl group (—OC(═O)—);

haloalkoxy: straight-chain or branched alkyl groups having 1 to 6 carbon atoms, it being possible for the hydrogen atoms in these groups to be partly or completely replaced by halogen atoms as mentioned above, and these groups being bonded to the structure via an oxygen atom;

alkylthio: straight-chain or branched alkyl groups having 1 to 4 or 6 carbon atoms as mentioned above, which are bonded to the structure via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, eg. cyclopropyl, cyclobutyl, cyclopentyl and cyclohexyl;

alkenyl: straight-chain or branched alkenyl groups having 2 to 6 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: straight-chain or branched alkenyl groups having 2 to 6 carbon atoms and a double bond in any desired position, which are bonded to the structure via an oxygen atom (—O—);

alkenylcarbonyl: straight-chain or branched alkenyl groups having 2 to 10 carbon atoms and a double bond in any desired position, which are bonded to the structure via a carbonyl group (—CO—);

alkenylthio or alkenylamino: straight-chain or branched alkenyl groups having 2 to 6 carbon atoms and a double bond in any desired position, which are bonded to the structure (alkenylthio) via a sulfur atom or (alkenylamino) a nitrogen atom;

alkynyl: straight-chain or branched alkynyl groups having 2 to 10 carbon atoms and a triple bond in any desired position, eg. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynylcarbonyl: straight-chain or branched alkynyl groups having 3 to 10 carbon atoms and a triple bond in any desired position, which are bonded to the structure via a carbonyl group (—CO—);

alkynyloxy or alkynylthio and alkynylamino: straight-chain or branched alkynyl groups having 2 to 6 carbon atoms and a triple bond in any desired position, which are bonded to the structure (alkynyloxy) via an oxygen atom or (alkynylthio) via a sulfur atom or (alkynylamino) via a nitrogen atom;

cycloalkenyl or cycloalkenyloxy, cycloalkenylthio and cycloalkylamino [sic]: monocyclic alkenyl groups having 3 to 6 carbon ring members, which are bonded to the structure directly or (cycloalkenyloxy) via an oxygen atom or (cycloalkenylthio) a sulfur atom or (cycloalkenylamino) via a nitrogen atom, eg. cyclopropenyl, cyclobutenyl, cyclopentenyl or cyclohexenyl;

cycloalkoxy or cycloalkylthio and cycloalkylamino: monocyclic alkenyl groups having 3 to 6 carbon ring members, which are bonded to the structure (cycloalkoxy) via an oxygen atom or (cycloalkylthio) a sulfur atom or (cycloalkylamino) via a nitrogen atom, eg. cyclopropyl, cyclobutyl, cyclopentyl or cyclohexyl;

heterocyclyl or heterocyclyloxy, heterocyclylthio and heterocyclylamino: three- to six-membered, saturated or partly unsaturated mono- or polycyclic heterocycles, which contain one to three heteroatoms selected from a group consisting of oxygen, nitrogen and sulfur, and which are bonded to the structure directly or (heterocyclyloxy) via an oxygen atom or (heterocyclylthio) via a sulfur atom or (heterocyclylamino) via a nitrogen atom, such as eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl [sic], 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5- dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl;

aryl or aryloxy, arylthio, arylcarbonyl and arylsulfonyl: aromatic mono- or polycyclic hydrocarbon radicals which are bonded to the structure directly or (aryloxy) via an oxygen atom (—O—) or (arylthio) a sulfur atom (—S—), (arylcarbonyl) via a carbonyl group (—CO—) or (arylsulfonyl) via a sulfonyl group (—$SO_2$—), eg. phenyl, naphthyl and phenanthrenyl or phenoxy, naphthyloxy and phenanthrenyloxy and the corresponding carbonyl and sulfonyl radicals;

arylamino: aromatic mono- or polycyclic hydrocarbon radicals which are bonded to the structure via a nitrogen atom;

hetaryl or hetaryloxy, hetarylthio, hetarylcarbonyl and hetarylsulfonyl: aromatic mono- or polycyclic radicals which, in addition to carbon ring members, additionally can contain one to four nitrogen atoms or one to three nitrogen atoms and an oxygen or a sulfur atom or an oxygen or a sulfur atom and which are bonded to the structure directly or (hetaryloxy) via an oxygen atom (—O—) or (hetarylthio) a sulfur atom (—S—), (hetarylcarbonyl) via a carbonyl group (—CO—) or (hetarylsulfonyl) via a sulfonyl group (—SO—), eg.

5-membered heteroaryl, containing one to three nitrogen atoms: 5-membered ring heteroaryl groups which, in addition to carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl, containing one to four nitrogen atoms or one to three nitrogen atoms and a sulfur or oxygen atom or an oxygen or a sulfur atom: 5-membered ring heteroaryl groups which, in addition to carbon atoms, can contain one to four nitrogen atoms or one to three nitrogen atoms and a sulfur or oxygen atom or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, containing one to three nitrogen atoms or one nitrogen atom and/or an oxygen or sulfur atom: 5-membered ring heteroaryl groups which, in addition to carbon atoms, can contain one to four nitrogen atoms or one to three nitrogen atoms and a sulfur or oxygen atom or an oxygen or a sulfur atom as ring members, and in which two adjacent carbon ring members or a nitrogen and an adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three nitrogen atoms: 5-membered ring heteroaryl groups which, in addition to carbon atoms, can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl, containing one to three or one to four nitrogen atoms: 6-membered ring heteroaryl groups which, in addition to carbon atoms, can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazinyl;

benzo-fused 6-membered heteroaryl, containing one to four nitrogen atoms: 6-membered ring heteroaryl groups in which two adjacent carbon ring members can be bridged by a buta-1,3-diene-1,4-diyl group, eg. quinoline, isoquinoline, quinazoline and quinoxaline, or the corresponding oxy, thio, carbonyl or sulfonyl groups;

hetarylamino: aromatic mono- or polycyclic radicals which, in addition to carbon ring members, can additionally contain one to four nitrogen atoms or one to three nitrogen atoms and an oxygen or a sulfur atom or an oxygen or a sulfur atom and which are bonded to the structure via a nitrogen atom.

The statement partly or completely halogenated is intended to express that in the groups characterized in this way the hydrogen atoms can be partly or completely replaced by identical or different halogen atoms as mentioned above.

With respect to their biological action, compounds of the formula I are preferred in which m is 0.

Equally preferred are compounds of the formula I in which R is hydrogen or methyl.

Equally preferred are compounds of the formula I in which $R^1$ is hydrogen or methyl.

Compounds of the formula I are particularly preferred in which R is hydrogen and $R^1$ is hydrogen or methyl.

Compounds of the formula I are particularly preferred in which R and $R^1$ are simultaneously hydrogen or methyl.

In addition, compounds I are preferred in which $R^3$ is hydrogen, hydroxyl, cyclopropyl, chlorine, methyl, methoxy, methylthio or phenyl.

Compounds I are additionally preferred in which $R^3$ is methyl.

In addition, compounds I are preferred in which $R^3$ is methoxy.

Compounds I are additionally preferred in which $R^3$ is hydroxyl.

In addition, compounds I are preferred in which $R^3$ is chlorine.

In addition, compounds I are preferred in which $R^4$ is hydrogen, hydroxyl, cyclopropyl, chlorine, methyl, ethyl, isopropyl, methoxy or methylthio.

Compounds I are additionally preferred in which $R^4$ is methyl.

In addition, compounds I are preferred in which $R^4$ is methoxy.

Compounds I are additionally preferred in which $R^4$ is hydroxyl.

In addition, compounds I are preferred in which $R^4$ is ethyl.

Compounds I are additionally preferred in which $R^4$ is isopropyl.

Compounds I are additionally preferred in which $R^4$ is cyclopropyl.

In addition, compounds I are preferred in which $R^4$ is unsubstituted or substituted aryl or hetaryl.

In addition, compounds I are preferred in which $R^4$ is unsubstituted or substituted pyridyl, pyrimidyl, pyrazinyl, pyridazinyl or triazinyl.

In addition, compounds I are preferred in which $R^4$ is unsubstituted or substituted furyl, thienyl or pyrrolyl.

In addition, compounds I are preferred in which $R^4$ is unsubstituted or substituted oxazolyl, thiazolyl, isoxazolyl, isothiazolyl, pyrazolyl or imidazolyl.

In addition, compounds I are preferred in which $R^4$ is unsubstituted or substituted oxdiazolyl, thiadiazolyl or triazolyl.

Compounds I are additionally preferred in which $R^4$ is phenyl, which is unsubstituted or carries one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino, $C_1$–$C_4$-alkylsulfonyl, $C_1$–$C_4$-alkoxycarbonyl, $C_1$–$C_4$-alkylaminocarbonyl or di-$C_1$–$C_4$-alkylaminocarbonyl.

Compounds I are additionally preferred in which $R^5$ is hydrogen, $C_1$–$C_6$-alkyl, arylalkyl, hetarylalkyl, aryloxyalkyl, hetaryloxyalkyl, aryl or hetaryl.

In addition, compounds I are preferred in which $R^5$ is $C_1$–$C_6$-alkyl.

Compounds I are additionally preferred in which $R^5$ is methyl or ethyl.

In addition, compounds I are preferred in which $R^5$ is arylalkyl or hetarylalkyl.

Compounds I are additionally preferred in which $R^5$ is aryloxyalkyl or hetaryloxyalkyl.

Compounds I are additionally preferred in which $R^5$ is aryl or hetaryl.

In addition, compounds of the formula I are preferred in which X is O.

In addition, compounds of the formula I are preferred in which X is S.

The compounds I compiled in the following tables are particularly preferred with respect to their use.

Table 1

Compounds of the general formula I.1 in which $(R^2)_m$ is hydrogen and the combination of the substituents $R^3$, $R^4$ and $R^5$ for a compound in each case corresponds to one line of Table A

I.1

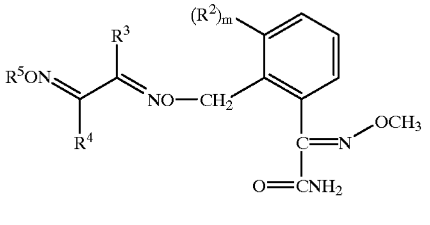

Table 2

Compounds of the general formula I.1 in which $(R^2)_m$ is chlorine and the combination of the substituents $R^3$, $R^4$ and $R^5$ for a compound in each case corresponds to one line of Table A.

Table 3

Compounds of the general formula I.2 in which $(R^2)_m$ is hydrogen and the combination of the substituents $R^3$, $R^4$ and $R^5$ for a compound in each case corresponds to one line of Table A.

I.2

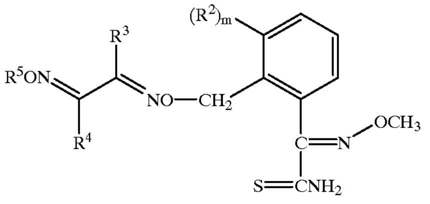

Table 4

Compounds of the general formula I.2 in which $(R^2)_m$ is chlorine and the combination of the substituents $R^3$, $R^4$ and $R^5$ for a compound in each case corresponds to one line of Table A.

Table 5

Compounds of the general formula I.3 in which $(R^2)_m$ is hydrogen and the combination of the substituents $R^3$, $R^4$ and $R^5$ for a compound in each case corresponds to one line of Table A.

I.3

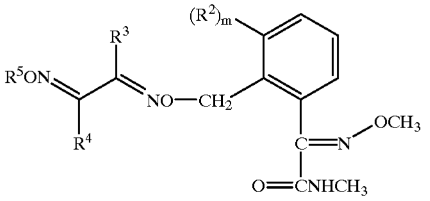

Table 6

Compounds of the general formula I.3 in which $(R^2)_m$ is chlorine and the combination of the substituents $R^3$, $R^4$ and $R^5$ for a compound in each case corresponds to one line of Table A.

Table 7

Compounds of the general formula I.4 in which $(R^2)_m$ is hydrogen and the combination of the substituents $R^3$, $R^4$ and $R^5$ for a compound in each case corresponds to one line of Table A.

I.4

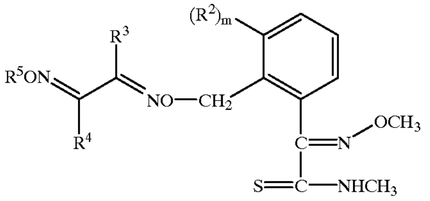

Table 8

Compounds of the general formula I.4 in which $(R^2)_m$ is chlorine and the combination of the substituents $R^3$, $R^4$ and $R^5$ for a compound in each case corresponds to one line of Table A.

Table 9

Compounds of the general formula I.5 in which $(R^2)_m$ is hydrogen and the combination of the substituents $R^3$, $R^4$ and $R^5$ for a compound in each case corresponds to one line of Table A.

I.5

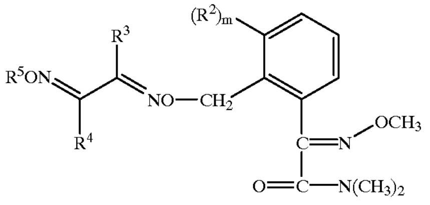

Table 10

Compounds of the general formula I.5 in which $(R^2)_m$ is chlorine and the combination of the substituents $R^3$, $R^4$ and $R^5$ for a compound in each case corresponds to one line of Table A.

Table 11

Compounds of the general formula I.6 in which $(R^2)_m$ is hydrogen and the combination of the substituents $R^3$, $R^4$ and $R^5$ for a compound in each case corresponds to one line of Table A.

I.6

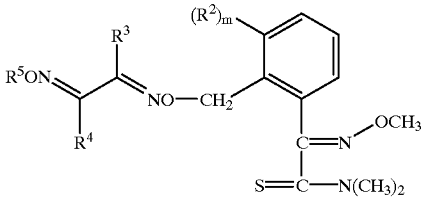

Table 12

Compounds of the general formula I.6 in which $(R^2)_m$ is chlorine and the combination of the substituents $R^3$, $R^4$ and $R^5$ for a compound in each case corresponds to one line of Table A.

TABLE A

| No. | $R^3$ | $R^4$ | $R^5$ |
|---|---|---|---|
| 1 | $CH_3$ | $CH_3$ | H |
| 2 | $CH_3$ | $CH_3$ | $CH_3$ |
| 3 | $CH_3$ | $CH_3$ | $C_2H_5$ |
| 4 | $CH_3$ | $CH_3$ | n-$C_3H_7$ |
| 5 | $CH_3$ | $CH_3$ | i-$C_3H_7$ |
| 6 | $CH_3$ | $CH_3$ | Cyclopropyl |
| 7 | $CH_3$ | $CH_3$ | n-$C_4H_9$ |
| 8 | $CH_3$ | $CH_3$ | s-$C_4H_9$ |
| 9 | $CH_3$ | $CH_3$ | i-$C_4H_9$ |
| 10 | $CH_3$ | $CH_3$ | t-$C_4H_9$ |
| 11 | $CH_3$ | $CH_3$ | n-$C_5H_{11}$ |
| 12 | $CH_3$ | $CH_3$ | i-$C_5H_{11}$ |
| 13 | $CH_3$ | $CH_3$ | neo-$C_5H_{11}$ |
| 14 | $CH_3$ | $CH_3$ | Cyclopentyl |
| 15 | $CH_3$ | $CH_3$ | n-$C_6H_{13}$ |
| 16 | $CH_3$ | $CH_3$ | Cyclohexyl |
| 17 | $CH_3$ | $CH_3$ | n-$C_8H_{17}$ |
| 18 | $CH_3$ | $CH_3$ | $CH_2CH_2Cl$ |
| 19 | $CH_3$ | $CH_3$ | $(CH_2)_4Cl$ |
| 20 | $CH_3$ | $CH_3$ | $CH_2CN$ |
| 21 | $CH_3$ | $CH_3$ | $CH_2CH_2CN$ |
| 22 | $CH_3$ | $CH_3$ | $(CH_2)_3CN$ |
| 23 | $CH_3$ | $CH_3$ | $(CH_2)_4CN$ |
| 24 | $CH_3$ | $CH_3$ | $(CH_2)_6CN$ |
| 25 | $CH_3$ | $CH_3$ | Cyclohexylmethyl |
| 26 | $CH_3$ | $CH_3$ | 2-Cyclohexyleth-1-yl |
| 27 | $CH_3$ | $CH_3$ | Cyclopropylmethyl |
| 28 | $CH_3$ | $CH_3$ | 2-Cyclopropyleth-1-yl |
| 29 | $CH_3$ | $CH_3$ | 2-Methoxyeth-1-yl |

TABLE A-continued

| No. | $R^3$ | $R^4$ | $R^5$ |
|---|---|---|---|
| 30 | $CH_3$ | $CH_3$ | 2-Ethoxyeth-1-yl |
| 31 | $CH_3$ | $CH_3$ | 2-Isopropoxyeth-1-yl |
| 32 | $CH_3$ | $CH_3$ | 3-Methoxyprop-1-yl |
| 33 | $CH_3$ | $CH_3$ | 3-Ethoxyprop-1-yl |
| 34 | $CH_3$ | $CH_3$ | 3-Isopropoxyprop-1-yl |
| 35 | $CH_3$ | $CH_3$ | 4-Methoxybut-1-yl |
| 36 | $CH_3$ | $CH_3$ | 4-Isopropoxybut-1-yl |
| 37 | $CH_3$ | $CH_3$ | Propen-3-yl |
| 38 | $CH_3$ | $CH_3$ | But-2-en-1-yl |
| 39 | $CH_3$ | $CH_3$ | 3-Methylbut-2-en-1-yl |
| 40 | $CH_3$ | $CH_3$ | 2-Vinyloxyeth-1-yl |
| 41 | $CH_3$ | $CH_3$ | Allyloxyeth-1-yl |
| 42 | $CH_3$ | $CH_3$ | 2-Trifluoromethoxyeth-1-yl |
| 43 | $CH_3$ | $CH_3$ | 3-Trifluoromethoxyprop-1-yl |
| 44 | $CH_3$ | $CH_3$ | 4-Difluoromethoxybut-1-yl |
| 45 | $CH_3$ | $CH_3$ | Hydroxycarbonylmethyl |
| 46 | $CH_3$ | $CH_3$ | Methoxycarbonylmethyl |
| 47 | $CH_3$ | $CH_3$ | Aminocarbonylmethyl |
| 48 | $CH_3$ | $CH_3$ | N-Methylaminocarbonylmethyl |
| 49 | $CH_3$ | $CH_3$ | N,N-Dimethylaminocarbonyl-methyl |
| 50 | $CH_3$ | $CH_3$ | 2-Hydroxycarbonyleth-1-yl |
| 51 | $CH_3$ | $CH_3$ | 2-Methoxycarbonyleth-1-yl |
| 52 | $CH_3$ | $CH_3$ | 2-Aminocarbonyleth-1-yl |
| 53 | $CH_3$ | $CH_3$ | 2-N-Methylaminocarbon-yleth-1-yl |
| 54 | $CH_3$ | $CH_3$ | 2-Dimethylaminocarbon-yleth-1-yl |
| 55 | $CH_3$ | $CH_3$ | 2-Aminoeth-1-yl |
| 56 | $CH_3$ | $CH_3$ | 2-Aminoprop-1-yl |
| 57 | $CH_3$ | $CH_3$ | 4-Aminobut-1-yl |
| 58 | $CH_3$ | $CH_3$ | 3-Dimethylaminoprop-1-yl |
| 59 | $CH_3$ | $CH_3$ | 4-Aminothiocarbonylbut-1-yl |
| 60 | $CH_3$ | $CH_3$ | 2-Oxopropyl |
| 61 | $CH_3$ | $CH_3$ | Cyclohexyl |
| 62 | $CH_3$ | $CH_3$ | Cyclopropyl |
| 63 | $CH_3$ | $CH_3$ | Cyclopentyl |
| 64 | $CH_3$ | $CH_3$ | 2-Methoxyiminoprop-1-yl |
| 65 | $CH_3$ | $CH_3$ | 2-Methoxyiminoeth-1-yl |
| 66 | $CH_3$ | $CH_3$ | 6-Aminocarbonylhex-1-yl |
| 67 | $CH_3$ | $CH_3$ | 3-Aminothiocarbonyl-prop-1-yl |
| 68 | $CH_3$ | $CH_3$ | 2-Aminothiocarbonyleth-1-yl |
| 69 | $CH_3$ | $CH_3$ | Aminothiocarbonylmethyl |
| 70 | $CH_3$ | $CH_3$ | 4-(N,N-Dimethylamino)-but-1-yl |
| 71 | $CH_3$ | $CH_3$ | 2-(Methylthio)eth-1-yl |
| 72 | $CH_3$ | $CH_3$ | 2-(Methylsulfonyl)eth-1-yl |
| 73 | $CH_3$ | $CH_3$ | 4-(Methylthio)prop-1-yl |
| 74 | $CH_3$ | $CH_3$ | 4-(Methylsulfonyl)prop-1-yl |
| 75 | $CH_3$ | $CH_3$ | Benyzl |
| 76 | $CH_3$ | $CH_3$ | 2-F—$C_6H_4$—$CH_2$ |
| 77 | $CH_3$ | $CH_3$ | 3-F—$C_6H_4$—$CH_2$ |
| 78 | $CH_3$ | $CH_3$ | 4-F—$C_6H_4$—$CH_2$ |
| 79 | $CH_3$ | $CH_3$ | 2,3-$F_2$—$C_6H_3$—$CH_2$ |
| 80 | $CH_3$ | $CH_3$ | 2,4-$F_2$—$C_6H_3$—$CH_2$ |
| 81 | $CH_3$ | $CH_3$ | 2,5-$F_2$—$C_6H_3$—$CH_2$ |
| 82 | $CH_3$ | $CH_3$ | 2,6-$F_2$—$C_6H_3$—$CH_2$ |
| 83 | $CH_3$ | $CH_3$ | 3,4-$F_2$—$C_6H_3$—$CH_2$ |
| 84 | $CH_3$ | $CH_3$ | 3,5-$F_2$—$C_6H_3$—$CH_2$ |
| 85 | $CH_3$ | $CH_3$ | 2-Cl—$C_6H_4$—$CH_2$ |
| 86 | $CH_3$ | $CH_3$ | 3-Cl—$C_6H_4$—$CH_2$ |
| 87 | $CH_3$ | $CH_3$ | 4-Cl—$C_6H_4$—$CH_2$ |
| 88 | $CH_3$ | $CH_3$ | 2,3-$Cl_2$—$C_6H_3$—$CH_2$ |
| 89 | $CH_3$ | $CH_3$ | 2,4-$Cl_2$—$C_6H_3$—$CH_2$ |
| 90 | $CH_3$ | $CH_3$ | 2,5-$Cl_2$—$C_6H_3$—$CH_2$ |
| 91 | $CH_3$ | $CH_3$ | 2,6-$Cl_2$—$C_6H_3$—$CH_2$ |
| 92 | $CH_3$ | $CH_3$ | 3,4-$Cl_2$—$C_6H_3$—$CH_2$ |
| 93 | $CH_3$ | $CH_3$ | 3,5-$Cl_2$—$C_6H_3$—$CH_2$ |
| 94 | $CH_3$ | $CH_3$ | 2,3,4-$Cl_3$—$C_6H_2$—$CH_2$ |
| 95 | $CH_3$ | $CH_3$ | 2,3,5-$Cl_3$—$C_6H_2$—$CH_2$ |
| 96 | $CH_3$ | $CH_3$ | 2,3,6-$Cl_3$—$C_6H_2$—$CH_2$ |
| 97 | $CH_3$ | $CH_3$ | 2,4,5-$Cl_3$—$C_6H_2$—$CH_2$ |
| 98 | $CH_3$ | $CH_3$ | 2,4,6-$Cl_3$—$C_6H_2$—$CH_2$ |
| 99 | $CH_3$ | $CH_3$ | 3,4,5-$Cl_3$—$C_6H_2$—$CH_2$ |
| 100 | $CH_3$ | $CH_3$ | 2-Br—$C_6H_4$—$CH_2$ |
| 101 | $CH_3$ | $CH_3$ | 3-Br—$C_6H_4$—$CH_2$ |

TABLE A-continued

| No. | $R^3$ | $R^4$ | $R^5$ |
|---|---|---|---|
| 102 | $CH_3$ | $CH_3$ | 4-Br—$C_6H_4$—$CH_2$ |
| 103 | $CH_3$ | $CH_3$ | 2,3-$Br_2$—$C_6H_3$—$CH_2$ |
| 104 | $CH_3$ | $CH_3$ | 2,4-$Br_2$—$C_6H_3$—$CH_2$ |
| 105 | $CH_3$ | $CH_3$ | 2,5-$Br_2$—$C_6H_3$—$CH_2$ |
| 106 | $CH_3$ | $CH_3$ | 2,6-$Br_2$—$C_6H_3$—$CH_2$ |
| 107 | $CH_3$ | $CH_3$ | 3,4-$Br_2$—$C_6H_3$—$CH_2$ |
| 108 | $CH_3$ | $CH_3$ | 3,5-$Br_2$—$C_6H_3$—$CH_2$ |
| 109 | $CH_3$ | $CH_3$ | 2-F, 3-Cl—$C_6H_3$—$CH_2$ |
| 110 | $CH_3$ | $CH_3$ | 2-F, 4-Cl—$C_6H_3$—$CH_2$ |
| 111 | $CH_3$ | $CH_3$ | 2-F, 5-Cl—$C_6H_3$—$CH_2$ |
| 112 | $CH_3$ | $CH_3$ | 2-F, 3-Br—$C_6H_3$—$CH_2$ |
| 113 | $CH_3$ | $CH_3$ | 2-F, 4-Br—$C_6H_3$—$CH_2$ |
| 114 | $CH_3$ | $CH_3$ | 2-F, 5-Br—$C_6H_3$—$CH_2$ |
| 115 | $CH_3$ | $CH_3$ | 2-Cl, 3-Br—$C_6H_3$—$CH_2$ |
| 116 | $CH_3$ | $CH_3$ | 2-Cl, 4-Br—$C_6H_3$—$CH_2$ |
| 117 | $CH_3$ | $CH_3$ | 2-Cl, 5-Br—$C_6H_3$—$CH_2$ |
| 118 | $CH_3$ | $CH_3$ | 3-F, 4-Cl—$C_6H_3$—$CH_2$ |
| 119 | $CH_3$ | $CH_3$ | 3-F, 5-Cl—$C_6H_3$—$CH_2$ |
| 120 | $CH_3$ | $CH_3$ | 3-F, 6-Cl—$C_6H_3$—$CH_2$ |
| 121 | $CH_3$ | $CH_3$ | 3-F, 4-Br—$C_6H_3$—$CH_2$ |
| 122 | $CH_3$ | $CH_3$ | 3-F, 5-Br—$C_6H_3$—$CH_2$ |
| 123 | $CH_3$ | $CH_3$ | 3-F, 6-Br—$C_6H_3$—$CH_2$ |
| 124 | $CH_3$ | $CH_3$ | 3-Cl, 4-Br—$C_6H_3$—$CH_2$ |
| 125 | $CH_3$ | $CH_3$ | 3-Cl, 5-Br—$C_6H_3$—$CH_2$ |
| 126 | $CH_3$ | $CH_3$ | 3-Cl, 6-Br—$C_6H_3$—$CH_2$ |
| 127 | $CH_3$ | $CH_3$ | 4-F, 5-Cl—$C_6H_3$—$CH_2$ |
| 128 | $CH_3$ | $CH_3$ | 4-F, 6-Cl—$C_6H_3$—$CH_2$ |
| 129 | $CH_3$ | $CH_3$ | 4-F, 5-Br—$C_6H_3$—$CH_2$ |
| 130 | $CH_3$ | $CH_3$ | 4-F, 6-Br—$C_6H_3$—$CH_2$ |
| 131 | $CH_3$ | $CH_3$ | 4-Cl, 5-Br—$C_6H_3$—$CH_2$ |
| 132 | $CH_3$ | $CH_3$ | 5-F, 6-Cl—$C_6H_3$—$CH_2$ |
| 133 | $CH_3$ | $CH_3$ | 5-F, 6-Br—$C_6H_3$—$CH_2$ |
| 134 | $CH_3$ | $CH_3$ | 5-Cl, 6-Br—$C_6H_3$—$CH_2$ |
| 135 | $CH_3$ | $CH_3$ | 3-Br, 4-Cl, 5-Br—$C_6H_2$—$CH_2$ |
| 136 | $CH_3$ | $CH_3$ | 2-CN—$C_6H_4$—$CH_2$ |
| 137 | $CH_3$ | $CH_3$ | 3-CN—$C_6H_4$—$CH_2$ |
| 138 | $CH_3$ | $CH_3$ | 4-CN—$C_6H_4$—$CH_2$ |
| 139 | $CH_3$ | $CH_3$ | 2-$NO_2$—$C_6H_4$—$CH_2$ |
| 140 | $CH_3$ | $CH_3$ | 3-$NO_2$—$C_6H_4$—$CH_2$ |
| 141 | $CH_3$ | $CH_3$ | 4-$NO_2$—$C_6H_4$—$CH_2$ |
| 142 | $CH_3$ | $CH_3$ | 2-$CH_3$—$C_6H_4$—$CH_2$ |
| 143 | $CH_3$ | $CH_3$ | 3-$CH_3$—$C_6H_4$—$CH_2$ |
| 144 | $CH_3$ | $CH_3$ | 4-$CH_3$—$C_6H_4$—$CH_2$ |
| 145 | $CH_3$ | $CH_3$ | 2,3-$(CH_3)_2$—$C_6H_3$—$CH_2$ |
| 146 | $CH_3$ | $CH_3$ | 2,4-$(CH_3)_2$—$C_6H_3$—$CH_2$ |
| 147 | $CH_3$ | $CH_3$ | 2,5-$(CH_3)_2$—$C_6H_3$—$CH_2$ |
| 148 | $CH_3$ | $CH_3$ | 2,6-$(CH_3)_2$—$C_6H_3$—$CH_2$ |
| 149 | $CH_3$ | $CH_3$ | 3,4-$(CH_3)_2$—$C_6H_3$—$CH_2$ |
| 150 | $CH_3$ | $CH_3$ | 3,5-$(CH_3)_2$—$C_6H_3$—$CH_2$ |
| 151 | $CH_3$ | $CH_3$ | 2-$C_2H_5$—$C_6H_4$—$CH_2$ |
| 152 | $CH_3$ | $CH_3$ | 3-$C_2H_5$—$C_6H_4$—$CH_2$ |
| 153 | $CH_3$ | $CH_3$ | 4-$C_2H_5$—$C_6H_4$—$CH_2$ |
| 154 | $CH_3$ | $CH_3$ | 2-i-$C_3H_7$—$C_6H_4$—$CH_2$ |
| 155 | $CH_3$ | $CH_3$ | 3-i-$C_3H_7$—$C_6H_4$—$CH_2$ |
| 156 | $CH_3$ | $CH_3$ | 4-i-$C_3H_7$—$C_6H_4$—$CH_2$ |
| 157 | $CH_3$ | $CH_3$ | 2-Cyclohexyl-$C_6H_4$—$CH_2$ |
| 158 | $CH_3$ | $CH_3$ | 3-Cyclohexyl-$C_6H_4$—$CH_2$ |
| 159 | $CH_3$ | $CH_3$ | 4-Cyclohexyl-$C_6H_4$—$CH_2$ |
| 160 | $CH_3$ | $CH_3$ | 2-Vinyl-$C_6H_4$—$CH_2$ |
| 161 | $CH_3$ | $CH_3$ | 3-Vinyl-$C_6H_4$—$CH_2$ |
| 162 | $CH_3$ | $CH_3$ | 4-Vinyl-$C_6H_4$—$CH_2$ |
| 163 | $CH_3$ | $CH_3$ | 2-Allyl-$C_6H_4$—$CH_2$ |
| 164 | $CH_3$ | $CH_3$ | 3-Allyl-$C_6H_4$—$CH_2$ |
| 165 | $CH_3$ | $CH_3$ | 4-Allyl-$C_6H_4$—$CH_2$ |
| 166 | $CH_3$ | $CH_3$ | 2-$C_6H_5$—$C_6H_4$—$CH_2$ |
| 167 | $CH_3$ | $CH_3$ | 3-$C_6H_5$—$C_6H_4$—$CH_2$ |
| 168 | $CH_3$ | $CH_3$ | 4-$C_6H_5$—$C_6H_4$—$CH_2$ |
| 169 | $CH_3$ | $CH_3$ | 3-$CH_3$, 5-t-$C_4H_9$—$C_6H_3$—$CH_2$ |
| 170 | $CH_3$ | $CH_3$ | 2-OH—$C_6H_4$—$CH_2$ |
| 171 | $CH_3$ | $CH_3$ | 3-OH—$C_6H_4$—$CH_2$ |
| 172 | $CH_3$ | $CH_3$ | 4-OH—$C_6H_4$—$CH_2$ |
| 173 | $CH_3$ | $CH_3$ | 2-$OCH_3$—$C_6H_4$—$CH_2$ |
| 174 | $CH_3$ | $CH_3$ | 3-$OCH_3$—$C_6H_4$—$CH_2$ |
| 175 | $CH_3$ | $CH_3$ | 4-$OCH_3$—$C_6H_4$—$CH_2$ |
| 176 | $CH_3$ | $CH_3$ | 2,3-$(OCH_3)_2$—$C_6H_3$—$CH_2$ |
| 177 | $CH_3$ | $CH_3$ | 2,4-$(OCH_3)_2$—$C_6H_3$—$CH_2$ |
| 178 | $CH_3$ | $CH_3$ | 2,5-$(OCH_3)_2$—$C_6H_3$—$CH_2$ |

TABLE A-continued

| No. | $R^3$ | $R^4$ | $R^5$ |
|---|---|---|---|
| 179 | $CH_3$ | $CH_3$ | 3,4-$(OCH_3)_2$—$C_6H_3$—$CH_2$ |
| 180 | $CH_3$ | $CH_3$ | 3,5-$(OCH_3)_2$—$C_6H_3$—$CH_2$ |
| 181 | $CH_3$ | $CH_3$ | 3,4,5-$(OCH_3)_3$—$C_6H_2$—$CH_2$ |
| 182 | $CH_3$ | $CH_3$ | 2-$OC_2H_5$—$C_6H_4$—$CH_2$ |
| 183 | $CH_3$ | $CH_3$ | 3-$OC_2H_5$—$C_6H_4$—$CH_2$ |
| 184 | $CH_3$ | $CH_3$ | 4-$OC_2H_5$—$C_6H_4$—$CH_2$ |
| 185 | $CH_3$ | $CH_3$ | 2-O-(n-$C_3H_7$)—$C_6H_4$—$CH_2$ |
| 186 | $CH_3$ | $CH_3$ | 3-O-(n-$C_3H_7$)—$C_6H_4$—$CH_2$ |
| 187 | $CH_3$ | $CH_3$ | 4-O-(n-$C_3H_7$)—$C_6H_4$—$CH_2$ |
| 188 | $CH_3$ | $CH_3$ | 2-O-(i-$C_3H_7$)—$C_6H_4$—$CH_2$ |
| 189 | $CH_3$ | $CH_3$ | 3-O-(i-$C_3H_7$)—$C_6H_4$—$CH_2$ |
| 190 | $CH_3$ | $CH_3$ | 4-O-(i-$C_3H_7$)—$C_6H_4$—$CH_2$ |
| 191 | $CH_3$ | $CH_3$ | 4-O-(n-$C_4H_9$)—$C_6H_4$—$CH_2$ |
| 192 | $CH_3$ | $CH_3$ | 3-O-(t-$C_4H_9$)—$C_6H_4$—$CH_2$ |
| 193 | $CH_3$ | $CH_3$ | 4-O-(n-$C_6H_{13}$)—$C_6H_4$—$CH_2$ |
| 194 | $CH_3$ | $CH_3$ | 2-O-Allyl-$C_6H_4$—$CH_2$ |
| 195 | $CH_3$ | $CH_3$ | 3-O-Allyl-$C_6H_4$—$CH_2$ |
| 196 | $CH_3$ | $CH_3$ | 4-O-Allyl-$C_6H_4$—$CH_2$ |
| 197 | $CH_3$ | $CH_3$ | 2-$CF_3$—$C_6H_4$—$CH_2$ |
| 198 | $CH_3$ | $CH_3$ | 3-$CF_3$—$C_6H_4$—$CH_2$ |
| 199 | $CH_3$ | $CH_3$ | 4-$CF_3$—$C_6H_4$—$CH_2$ |
| 200 | $CH_3$ | $CH_3$ | 2-Acetyl-$C_6H_4$—$CH_2$ |
| 201 | $CH_3$ | $CH_3$ | 3-Acetyl-$C_6H_4$—$CH_2$ |
| 202 | $CH_3$ | $CH_3$ | 4-Acetyl-$C_6H_4$—$CH_2$ |
| 203 | $CH_3$ | $CH_3$ | 2-Methoxycarbonyl-$C_6H_4$—$CH_2$ |
| 204 | $CH_3$ | $CH_3$ | 3-Methoxycarbonyl-$C_6H_4$—$CH_2$ |
| 205 | $CH_3$ | $CH_3$ | 4-Methoxycarbonyl-$C_6H_4$—$CH_2$ |
| 206 | $CH_3$ | $CH_3$ | 2-Aminocarbonyl-$C_6H_4$—$CH_2$ |
| 207 | $CH_3$ | $CH_3$ | 3-Aminocarbonyl-$C_6H_4$—$CH_2$ |
| 208 | $CH_3$ | $CH_3$ | 4-Aminocarbonyl-$C_6H_4$—$CH_2$ |
| 209 | $CH_3$ | $CH_3$ | 2-Dimethylaminocarbonyl-$C_6H_4$—$CH_2$ |
| 210 | $CH_3$ | $CH_3$ | 3-Dimethylaminocarbonyl-$C_6H_4$—$CH_2$ |
| 211 | $CH_3$ | $CH_3$ | 4-Dimethylaminocarbonyl-$C_6H_4$—$CH_2$ |
| 212 | $CH_3$ | $CH_3$ | 2-(N-Methylaminocarbonyl)-$C_6H_4$—$CH_2$ |
| 213 | $CH_3$ | $CH_3$ | 3-(N-Methylaminocarbonyl)-$C_6H_4$—$CH_2$ |
| 214 | $CH_3$ | $CH_3$ | 4-(N-Methylaminocarbonyl)-$C_6H_4$—$CH_2$ |
| 215 | $CH_3$ | $CH_3$ | 2-$H_2N$—$C_6H_4$—$CH_2$ |
| 216 | $CH_3$ | $CH_3$ | 3-$H_2N$—$C_6H_4$—$CH_2$ |
| 217 | $CH_3$ | $CH_3$ | 4-$H_2N$—$C_6H_4$—$CH_2$ |
| 218 | $CH_3$ | $CH_3$ | 2-Aminothiocarbonyl-$C_6H_4$—$CH_2$ |
| 219 | $CH_3$ | $CH_3$ | 3-Aminothiocarbonyl-$C_6H_4$—$CH_2$ |
| 220 | $CH_3$ | $CH_3$ | 4-Aminothiocarbonyl-$C_6H_4$—$CH_2$ |
| 221 | $CH_3$ | $CH_3$ | 2-Methoxyiminomethyl-$C_6H_4$—$CH_2$ |
| 222 | $CH_3$ | $CH_3$ | 3-Methoxyiminomethyl-$C_6H_4$—$CH_2$ |
| 223 | $CH_3$ | $CH_3$ | 4-Methoxyiminomethyl-$C_6H_4$—$CH_2$ |
| 224 | $CH_3$ | $CH_3$ | 2-Formyl-$C_6H_4$—$CH_2$ |
| 225 | $CH_3$ | $CH_3$ | 3-Formyl-$C_6H_4$—$CH_2$ |
| 226 | $CH_3$ | $CH_3$ | 4-Formyl-$C_6H_4$—$CH_2$ |
| 227 | $CH_3$ | $CH_3$ | 2-(1'-Methoxyiminoeth-1'-yl)-$C_6H_4$—$CH_2$ |
| 228 | $CH_3$ | $CH_3$ | 3-(1'-Methoxyiminoeth-1'-yl)-$C_6H_4$—$CH_2$ |
| 229 | $CH_3$ | $CH_3$ | 4-(1'-Methoxyiminoeth-1'-yl)-$C_6H_4$—$CH_2$ |
| 230 | $CH_3$ | $CH_3$ | 2-$SCH_3$—$C_6H_4$—$CH_2$ |
| 231 | $CH_3$ | $CH_3$ | 3-$SCH_3$—$C_6H_4$—$CH_2$ |
| 232 | $CH_3$ | $CH_3$ | 4-$SCH_3$—$C_6H_4$—$CH_2$ |
| 233 | $CH_3$ | $CH_3$ | 2-$SO_2CH_3$—$C_6H_4$—$CH_2$ |
| 234 | $CH_3$ | $CH_3$ | 3-$SO_2CH_3$—$C_6H_4$—$CH_2$ |
| 235 | $CH_3$ | $CH_3$ | 4-$SO_2CH_3$—$C_6H_4$—$CH_2$ |
| 236 | $CH_3$ | $CH_3$ | 2-$OCF_3$—$C_6H_4$—$CH_2$ |
| 237 | $CH_3$ | $CH_3$ | 3-$OCF_3$—$C_6H_4$—$CH_2$ |
| 238 | $CH_3$ | $CH_3$ | 4-$OCF_3$—$C_6H_4$—$CH_2$ |
| 239 | $CH_3$ | $CH_3$ | 2-$OCHF_2$—$C_6H_4$—$CH_2$ |
| 240 | $CH_3$ | $CH_3$ | 3-$OCHF_2$—$C_6H_4$—$CH_2$ |

TABLE A-continued

| No. | $R^3$ | $R^4$ | $R^5$ |
|---|---|---|---|
| 241 | $CH_3$ | $CH_3$ | 4-$OCHF_2$—$C_6H_4$—$CH_2$ |
| 242 | $CH_3$ | $CH_3$ | 3-$CF_3$, 4-$OCF_3$—$C_6H_3$—$CH_2$ |
| 243 | $CH_3$ | $CH_3$ | 1-Naphthyl-$CH_2$ |
| 244 | $CH_3$ | $CH_3$ | 2-Naphthyl-$CH_2$ |
| 245 | $CH_3$ | $CH_3$ | 2-Phenoxyeth-1-yl |
| 246 | $CH_3$ | $CH_3$ | 2-(2'-Chlorophenoxy)eth-1-yl |
| 247 | $CH_3$ | $CH_3$ | 2-(3'-Chlorophenoxy)eth-1-yl |
| 248 | $CH_3$ | $CH_3$ | 2-(4'-Chlorophenoxy)eth-1-yl |
| 249 | $CH_3$ | $CH_3$ | 2-(3',5'-Dichlorophenoxy)-eth-1-yl |
| 250 | $CH_3$ | $CH_3$ | 2-(2'-Cyanophenoxy)eth-1-yl |
| 251 | $CH_3$ | $CH_3$ | 2-(3'-Cyanophenoxy)eth-1-yl |
| 252 | $CH_3$ | $CH_3$ | 2-(4'-Cyanophenoxy)eth-1-yl |
| 253 | $CH_3$ | $CH_3$ | 2-(2'-Methyl-phenoxy)eth-1-yl |
| 254 | $CH_3$ | $CH_3$ | 2-(3'-Methyl-phenoxy)eth-1-yl |
| 255 | $CH_3$ | $CH_3$ | 2-(4'-Methyl-phenoxy)eth-1-yl |
| 256 | $CH_3$ | $CH_3$ | 2-(3'-t-Butylphe-noxy)eth-1-yl |
| 257 | $CH_3$ | $CH_3$ | 2-(4'-t-Butylphe-noxy)eth-1-yl |
| 258 | $CH_3$ | $CH_3$ | 2-(2'-Nitrophenoxy)eth-1-yl |
| 259 | $CH_3$ | $CH_3$ | 2-(3'-Nitrophenoxy)eth-1-yl |
| 260 | $CH_3$ | $CH_3$ | 2-(4'-Nitrophenoxy)eth-1-yl |
| 261 | $CH_3$ | $CH_3$ | 2-(2'-Methoxyphen-oxy)eth-1-yl |
| 262 | $CH_3$ | $CH_3$ | 2-(3'-Methoxyphen-oxy)eth-1-yl |
| 263 | $CH_3$ | $CH_3$ | 2-(4'-Methoxyphen-oxy)eth-1-yl |
| 264 | $CH_3$ | $CH_3$ | 2-(2'-Trifluoromethylphen-oxy)eth-1-yl |
| 265 | $CH_3$ | $CH_3$ | 2-(3'-Trifluoromethylphen-oxy)eth-1-yl |
| 266 | $CH_3$ | $CH_3$ | 2-(4'-Trifluoromethylphen-oxy)eth-1-yl |
| 267 | $CH_3$ | $CH_3$ | 2-(2'-Acetylphenoxy)-eth-1-yl |
| 268 | $CH_3$ | $CH_3$ | 2-(3'-Acetylphenoxy)-eth-1-yl |
| 269 | $CH_3$ | $CH_3$ | 2-(4'-Acetylphenoxy)-eth-1-yl |
| 270 | $CH_3$ | $CH_3$ | 2-(2'-Methoxy-carbonyl)eth-1-yl |
| 271 | $CH_3$ | $CH_3$ | 2-(3'-Methoxy-carbonyl)eth-1-yl |
| 272 | $CH_3$ | $CH_3$ | 2-(4'-Methoxy-carbonyl)eth-1-yl |
| 273 | $CH_3$ | $CH_3$ | 2-(2'-Dimethylamino-carbonyl)eth-1-yl |
| 274 | $CH_3$ | $CH_3$ | 2-(3'-Dimethylamino-carbonyl)eth-1-yl |
| 275 | $CH_3$ | $CH_3$ | 2-(4'-Dimethylamino-carbonyl)eth-1-yl |
| 276 | $CH_3$ | $CH_3$ | 2-(2'-Aminothiocarbo-nyl)eth-1-yl |
| 277 | $CH_3$ | $CH_3$ | 2-(3'-Aminothiocarbo-nyl)eth-1-yl |
| 278 | $CH_3$ | $CH_3$ | 2-(4'-Aminothiocarbo-nyl)eth-1-yl |
| 279 | $CH_3$ | $CH_3$ | 2-(2'-Methyl-sulfonyl)eth-1-yl |
| 280 | $CH_3$ | $CH_3$ | 2-(3'-Methyl-sulfonyl)eth-1-yl |
| 281 | $CH_3$ | $CH_3$ | 2-(4'-Methyl-sulfonyl)eth-1-yl |
| 282 | $CH_3$ | $CH_3$ | 3-Phenoxyprop-1-yl |
| 283 | $CH_3$ | $CH_3$ | 3-(2'-Chlorophenoxy)prop-1-yl |
| 284 | $CH_3$ | $CH_3$ | 3-(3'-Chlorophenoxy)prop-1-yl |
| 285 | $CH_3$ | $CH_3$ | 3-(4'-Chlorophenoxy)prop-1-yl |
| 286 | $CH_3$ | $CH_3$ | 3-(3',5',Dichlorophenoxy)-prop-1-yl |
| 287 | $CH_3$ | $CH_3$ | 3-(2'-Cyanophen-oxy)prop-1-yl |
| 288 | $CH_3$ | $CH_3$ | 3-(3'-Cyanophen-oxy)prop-1-yl |
| 289 | $CH_3$ | $CH_3$ | 3-(4'-Cyanophen-oxy)prop-1-yl |
| 290 | $CH_3$ | $CH_3$ | 3-(2'-Methyl-phenoxy)prop-1-yl |
| 291 | $CH_3$ | $CH_3$ | 3-(3'-Methyl-phenoxy)prop-1-yl |
| 292 | $CH_3$ | $CH_3$ | 3-(4'-Methyl-phenoxy)prop-1-yl |
| 293 | $CH_3$ | $CH_3$ | 3-(2'-Methoxyphenoxy)prop-1-yl |
| 294 | $CH_3$ | $CH_3$ | 3-(3'-Methoxyphenoxy)prop-1-yl |
| 295 | $CH_3$ | $CH_3$ | 3-(4'-Methoxyphenoxy)prop-1-yl |
| 296 | $CH_3$ | $CH_3$ | 3-(2'-Trifluoromethyl-phenoxy)prop-1-yl |
| 297 | $CH_3$ | $CH_3$ | 3-(3'-Trifluoromethyl-phenoxy)prop-1-yl |
| 298 | $CH_3$ | $CH_3$ | 3-(4'-Trifluoromethyl-phenoxy)prop-1-yl |
| 299 | $CH_3$ | $CH_3$ | 4-Phenoxybut-1-yl |
| 300 | $CH_3$ | $CH_3$ | 2-Phenyleth-1-yl |
| 301 | $CH_3$ | $CH_3$ | 2-(2'-Chlorophenyl)eth-1-yl |
| 302 | $CH_3$ | $CH_3$ | 2-(3'-Chlorophenyl)eth-1-yl |
| 303 | $CH_3$ | $CH_3$ | 2-(4'-Chlorophenyl)eth-1-yl |
| 304 | $CH_3$ | $CH_3$ | 2-(3',5'-Dichlorophenyl)eth-1-yl |
| 305 | $CH_3$ | $CH_3$ | 2-(2'-Cyanophenyl)eth-1-yl |
| 306 | $CH_3$ | $CH_3$ | 2-(3'-Cyanophenyl)eth-1-yl |
| 307 | $CH_3$ | $CH_3$ | 2-(4'-Cyanophenyl)eth-1-yl |
| 308 | $CH_3$ | $CH_3$ | 2-(2'-Methylphenyl)eth-1-yl |
| 309 | $CH_3$ | $CH_3$ | 2-(3'-Methylphenyl)eth-1-y1 |
| 310 | $CH_3$ | $CH_3$ | 2-(4'-Methylphenyl)eth-1-yl |
| 311 | $CH_3$ | $CH_3$ | 2-(2'-Methoxy-phenyl)eth-1-yl |
| 312 | $CH_3$ | $CH_3$ | 2-(3'-Methoxy-phenyl)eth-1-yl |
| 313 | $CH_3$ | $CH_3$ | 2-(4'-Methoxy-phenyl)eth-1-yl |
| 314 | $CH_3$ | $CH_3$ | 2-(2'-Trifluoromethyl-phenyl)eth-1-yl |
| 315 | $CH_3$ | $CH_3$ | 2-(3'-Trifluoromethyl-phenyl)eth-1-yl |
| 316 | $CH_3$ | $CH_3$ | 2-(4'-Trifluoromethyl-phenyl)eth-1-yl |
| 317 | $CH_3$ | $CH_3$ | 3-Phenylprop-1-yl |
| 318 | $CH_3$ | $CH_3$ | 3-(2'-Chlorophenyl)prop-1-yl |
| 319 | $CH_3$ | $CH_3$ | 3-(3'-Chlorophenyl)prop-1-yl |
| 320 | $CH_3$ | $CH_3$ | 3-(4'-Chlorophenyl)prop-1-yl |
| 321 | $CH_3$ | $CH_3$ | 3-(2'-Cyanophenyl)prop-1-yl |
| 322 | $CH_3$ | $CH_3$ | 3-(3'-Cyanophenyl)prop-1-yl |
| 323 | $CH_3$ | $CH_3$ | 3-(4'-Cyanophenyl)prop-1-yl |
| 324 | $CH_3$ | $CH_3$ | 3-(2'-Trifluoromethyl-phenyl)prop-1-yl |
| 325 | $CH_3$ | $CH_3$ | 4-Phenylbut-1-yl |
| 326 | $CH_3$ | $CH_3$ | 4-(4'-Chlorophenyl)but-1-yl |
| 327 | $CH_3$ | $CH_3$ | 6-(4'-Chlorophenyl)hex-1-yl |
| 328 | $CH_3$ | $CH_3$ | 2-Pyridylmethyl |
| 329 | $CH_3$ | $CH_3$ | 3-Pyridylmethyl |
| 330 | $CH_3$ | $CH_3$ | 4-Pyridylmethyl |
| 331 | $CH_3$ | $CH_3$ | 4-Chloropyridin-2-ylmethyl |
| 332 | $CH_3$ | $CH_3$ | 5-Chloropyridin-2-ylmethyl |
| 333 | $CH_3$ | $CH_3$ | 6-Chloropyridin-2-ylmethyl |
| 334 | $CH_3$ | $CH_3$ | 5-Chloropyridin-3-ylmethyl |
| 335 | $CH_3$ | $CH_3$ | 6-Chloropyridin-3-ylmethyl |
| 336 | $CH_3$ | $CH_3$ | 2-Chloropyridin-4-ylmethyl |
| 337 | $CH_3$ | $CH_3$ | 2-Pyrimidinylmethyl |

TABLE A-continued

| No. | $R^3$ | $R^4$ | $R^5$ |
|---|---|---|---|
| 338 | $CH_3$ | $CH_3$ | 4-Chloropyrimidin-2-yl-methyl |
| 339 | $CH_3$ | $CH_3$ | 5-Chloropyrimidin-2-yl-methyl |
| 340 | $CH_3$ | $CH_3$ | 2-Chloropyrimidin-4-yl-methyl |
| 341 | $CH_3$ | $CH_3$ | 6-Chloropyrimidin-4-yl-methyl |
| 342 | $CH_3$ | $CH_3$ | 2-Chloropyrimidin-5-yl-methyl |
| 343 | $CH_3$ | $CH_3$ | 4-Pyridazinylmethyl |
| 344 | $CH_3$ | $CH_3$ | 2-Pyrazinylmethyl |
| 345 | $CH_3$ | $CH_3$ | 5-Chloropyrazin-2-ylmethyl |
| 346 | $CH_3$ | $CH_3$ | 6-Chloropyrazin-2-ylmethyl |
| 347 | $CH_3$ | $CH_3$ | 3-Pyridazinylmethyl |
| 348 | $CH_3$ | $CH_3$ | 6-Chloropyridazin-3-yl-methyl |
| 349 | $CH_3$ | $CH_3$ | 1,3,5-Triazinylmethyl |
| 350 | $CH_3$ | $CH_3$ | 2-Furylmethyl |
| 351 | $CH_3$ | $CH_3$ | 3-Furylmethyl |
| 352 | $CH_3$ | $CH_3$ | 4-Bromofur-2-ylmethyl |
| 353 | $CH_3$ | $CH_3$ | 5-Chlorofur-2-ylmethyl |
| 354 | $CH_3$ | $CH_3$ | 2-Thienylmethyl |
| 355 | $CH_3$ | $CH_3$ | 3-Thienylmethyl |
| 356 | $CH_3$ | $CH_3$ | 5-Methylthien-3-ylmethyl |
| 357 | $CH_3$ | $CH_3$ | 5-Chlorothien-2-ylmethyl |
| 358 | $CH_3$ | $CH_3$ | 2-Chlorothien-4-ylmethyl |
| 359 | $CH_3$ | $CH_3$ | 2-Pyrrolylmethyl |
| 360 | $CH_3$ | $CH_3$ | 3-Pyrrolylmethyl |
| 361 | $CH_3$ | $CH_3$ | 2-Oxazolylmethyl |
| 362 | $CH_3$ | $CH_3$ | 4-Methyloxazol-2-ylmethyl |
| 363 | $CH_3$ | $CH_3$ | 5-Methyloxazol-2-ylmethyl |
| 364 | $CH_3$ | $CH_3$ | 4-Chlorooxazol-2-ylmethyl |
| 365 | $CH_3$ | $CH_3$ | 5-Chlorooxazol-2-ylmethyl |
| 366 | $CH_3$ | $CH_3$ | 4-Oxazolylmethyl |
| 367 | $CH_3$ | $CH_3$ | 2-Methyloxazol-4-ylmethyl |
| 368 | $CH_3$ | $CH_3$ | 5-Methyloxazol-4-ylmethyl |
| 369 | $CH_3$ | $CH_3$ | 2-Chlorooxazol-4-ylmethyl |
| 370 | $CH_3$ | $CH_3$ | 5-Chlorooxazol-4-ylmethyl |
| 371 | $CH_3$ | $CH_3$ | 5-Oxazolylmethyl |
| 372 | $CH_3$ | $CH_3$ | 2-Methyloxazol-5-ylmethyl |
| 373 | $CH_3$ | $CH_3$ | 4-Methyloxazol-5-ylmethyl |
| 374 | $CH_3$ | $CH_3$ | 2-Chlorooxazol-5-ylmethyl |
| 375 | $CH_3$ | $CH_3$ | 4-Chlorooxazol-5-ylmethyl |
| 376 | $CH_3$ | $CH_3$ | 2-Thiazolylmethyl |
| 377 | $CH_3$ | $CH_3$ | 4-Methylthiazol-2-ylmethyl |
| 378 | $CH_3$ | $CH_3$ | 5-Methylthiazol-2-ylmethyl |
| 379 | $CH_3$ | $CH_3$ | 4-Chlorothiazol-2-ylmethyl |
| 380 | $CH_3$ | $CH_3$ | 5-Chlorothiazol-2-ylmethyl |
| 381 | $CH_3$ | $CH_3$ | 4-Thiazolylmethyl |
| 382 | $CH_3$ | $CH_3$ | 2-Methylthiazol-4-ylmethyl |
| 383 | $CH_3$ | $CH_3$ | 5-Methylthiazol-4-ylmethyl |
| 384 | $CH_3$ | $CH_3$ | 2-Chlorothiazol-4-ylmethyl |
| 385 | $CH_3$ | $CH_3$ | 5-Chlorothiazol-4-ylmethyl |
| 386 | $CH_3$ | $CH_3$ | 5-Thiazolylmethyl |
| 387 | $CH_3$ | $CH_3$ | 2-Methylthiazol-5-ylmethyl |
| 388 | $CH_3$ | $CH_3$ | 4-Methylthiazol-5-ylmethyl |
| 389 | $CH_3$ | $CH_3$ | 2-Chlorothiazol-5-ylmethyl |
| 390 | $CH_3$ | $CH_3$ | 4-Chlorothiazol-5-ylmethyl |
| 391 | $CH_3$ | $CH_3$ | 3-Isoxazolylmethyl |
| 392 | $CH_3$ | $CH_3$ | 4-Methylisoxazol-3-ylmethyl |
| 393 | $CH_3$ | $CH_3$ | 5-Methylisoxazol-3-ylmethyl |
| 394 | $CH_3$ | $CH_3$ | 4-Chloroisoxazol-3-ylmethyl |
| 395 | $CH_3$ | $CH_3$ | 5-Chloroisoxazol-3-ylmethyl |
| 396 | $CH_3$ | $CH_3$ | 4-Isoxazolylmethyl |
| 397 | $CH_3$ | $CH_3$ | 3-Methylisoxazol-4-ylmethyl |
| 398 | $CH_3$ | $CH_3$ | 5-Methylisoxazol-4-ylmethyl |
| 399 | $CH_3$ | $CH_3$ | 3-Chloroisoxazol-4-ylmethyl |
| 400 | $CH_3$ | $CH_3$ | 5-Chloroisoxazol-4-ylmethyl |
| 401 | $CH_3$ | $CH_3$ | 5-Isoxazolylmethyl |
| 402 | $CH_3$ | $CH_3$ | 3-Methylisoxazol-5-ylmethyl |
| 403 | $CH_3$ | $CH_3$ | 4-Methylisoxazol-5-ylmethyl |
| 404 | $CH_3$ | $CH_3$ | 3-Chloroisoxazol-5-ylmethyl |
| 405 | $CH_3$ | $CH_3$ | 4-Chloroisoxazol-5-ylmethyl |
| 406 | $CH_3$ | $CH_3$ | 3-Isothiazolylmethyl |
| 407 | $CH_3$ | $CH_3$ | 4-Methylisothiazol-3-yl-methyl |

TABLE A-continued

| No. | $R^3$ | $R^4$ | $R^5$ |
|---|---|---|---|
| 408 | $CH_3$ | $CH_3$ | 5-Methylisothiazol-3-yl-methyl |
| 409 | $CH_3$ | $CH_3$ | 4-Chloroisothiazol-3-yl-methyl |
| 410 | $CH_3$ | $CH_3$ | 5-Chloroisothiazol-3-yl-methyl |
| 411 | $CH_3$ | $CH_3$ | 4-Isothiazolylmethyl |
| 412 | $CH_3$ | $CH_3$ | 3-Methylisothiazol-4-yl methyl |
| 413 | $CH_3$ | $CH_3$ | 5-Methylisothiazol-4-yl-methyl |
| 414 | $CH_3$ | $CH_3$ | 3-Chloroisothiazol-4-yl-methyl |
| 415 | $CH_3$ | $CH_3$ | 5-Chloroisothiazol-4-yl-methyl |
| 416 | $CH_3$ | $CH_3$ | 5-Isothiazolylmethyl |
| 417 | $CH_3$ | $CH_3$ | 3-Methylisothiazol-5-yl-methyl |
| 418 | $CH_3$ | $CH_3$ | 4-Methylisothiazol-5-yl-methyl |
| 419 | $CH_3$ | $CH_3$ | 3-Chloroisothiazol-5-yl-methyl |
| 420 | $CH_3$ | $CH_3$ | 4-Chloroisothiazol-5-yl-methyl |
| 421 | $CH_3$ | $CH_3$ | 4-Imidazolylmethyl |
| 422 | $CH_3$ | $CH_3$ | 1-Phenylpyrazol-3-ylmethyl |
| 423 | $CH_3$ | $CH_3$ | 1-Methylimidazol-4-ylmethyl |
| 424 | $CH_3$ | $CH_3$ | 1-Phenyl-1,2,4-tri-azol-3-ylmethyl |
| 425 | $CH_3$ | $CH_3$ | 1,2,4-Oxadiazol-3-ylmethyl |
| 426 | $CH_3$ | $CH_3$ | 5-Chloro-1,2,4-oxadiazol-3-ylmethyl |
| 427 | $CH_3$ | $CH_3$ | 5-Methyl-1,2,4-oxadiazol-3-ylmethyl |
| 428 | $CH_3$ | $CH_3$ | 5-Trifluoromethyl-1,2,4-oxadiazol-3-ylmethyl |
| 429 | $CH_3$ | $CH_3$ | 1,3,4-Oxadiazol-2-ylmethyl |
| 430 | $CH_3$ | $CH_3$ | 5-Chloro-1,3,4-oxadiazol-2-ylmethyl |
| 431 | $CH_3$ | $CH_3$ | 5-Methyl-1,3,4-oxadiazol-2-ylmethyl |
| 432 | $CH_3$ | $CH_3$ | 5-Methoxy-1,3,4-oxadiazol-2-ylmethyl |
| 433 | $CH_3$ | $CH_3$ | 1,2,4-Thiadiazol-3-ylmethyl |
| 434 | $CH_3$ | $CH_3$ | 5-Chloro-1,2,4-thiadiazol-3-ylmethyl |
| 435 | $CH_3$ | $CH_3$ | 5-Methyl-1,2,4-thiadiazol-3-ylmethyl |
| 436 | $CH_3$ | $CH_3$ | 1,3,4-Thiadiazol-2-ylmethyl |
| 437 | $CH_3$ | $CH_3$ | 5-Chloro-1,3,4-thiadiazol-2-ylmethyl |
| 438 | $CH_3$ | $CH_3$ | 5-Methyl-1,3,4-thiadiazol-2-ylmethyl |
| 439 | $CH_3$ | $CH_3$ | 5-Cyano-1,3,4-thiadiazol-2-ylmethyl |
| 440 | $CH_3$ | $CH_3$ | 2-(2'-Pyridinyloxy)eth-1-yl |
| 441 | $CH_3$ | $CH_3$ | 2-(3'-Pyridinyloxy)eth-1-yl |
| 442 | $CH_3$ | $CH_3$ | 2-(4'-Pyridinyloxy)eth-1-yl |
| 443 | $CH_3$ | $CH_3$ | 2-(2'-Pyrimidiny-loxy)eth-1-yl |
| 444 | $CH_3$ | $CH_3$ | 2-(4'-Pyrimidiny-loxy)eth-1-yl |
| 445 | $CH_3$ | $CH_3$ | 2-(5'-Pyrimidiny-loxy)eth-1-yl |
| 446 | $CH_3$ | $CH_3$ | 2-(2'-Pyrazinyloxy)eth-1-yl |
| 447 | $CH_3$ | $CH_3$ | 2-(2'-Pyridaziny-loxy)eth-1-yl |
| 448 | $CH_3$ | $CH_3$ | 2-(3'-Pyridaziny-loxy)eth-1-yl |
| 449 | $CH_3$ | $CH_3$ | 2-(1',3',5'-Triazin-yloxy)eth-1-yl |
| 450 | $CH_3$ | $CH_3$ | 2-(5'-Methylisoxazol-3'-yl-oxy)eth-1-yl |
| 451 | $CH_3$ | $CH_3$ | 2-(5'-Chloroisoxazol-3'-yl-oxy)eth-1-yl |
| 452 | $CH_3$ | $CH_3$ | 2-(2'-Methoxythiazol-4'-yl-oxy)eth-1-yl |

TABLE A-continued

| No. | $R^3$ | $R^4$ | $R^5$ |
|---|---|---|---|
| 453 | $CH_3$ | $CH_3$ | 2-(4'-Chlorooxazol-2'-yl-oxy)eth-1-yl |
| 454 | $CH_3$ | $CH_3$ | 2-(1'-Phenyl-1'H-1',2',4'-triazol-3'-yloxy)eth-1-yl |
| 455 | $CH_3$ | $CH_3$ | 2-(1'-Phenylpyrazol-3'-yl-oxy)eth-1-yl |
| 456 | $CH_3$ | $CH_3$ | $C_6H_5$ |
| 457 | $CH_3$ | $CH_3$ | 2-Cl—$C_6H_4$ |
| 458 | $CH_3$ | $CH_3$ | 3-Cl—$C_6H_4$ |
| 459 | $CH_3$ | $CH_3$ | 4-Cl—$C_6H_4$ |
| 460 | $CH_3$ | $CH_3$ | 2,3-$Cl_2$—$C_6H_3$ |
| 461 | $CH_3$ | $CH_3$ | 2,4-$Cl_2$—$C_6H_3$ |
| 462 | $CH_3$ | $CH_3$ | 2,5-$Cl_2$—$C_6H_3$ |
| 463 | $CH_3$ | $CH_3$ | 3,4-$Cl_2$—$C_6H_3$ |
| 464 | $CH_3$ | $CH_3$ | 3,5-$Cl_2$—$C_6H_3$ |
| 465 | $CH_3$ | $CH_3$ | 4-CN—$C_6H_4$ |
| 466 | $CH_3$ | $CH_3$ | 2-$NO_2$—$C_6H_4$ |
| 467 | $CH_3$ | $CH_3$ | 3-$NO_2$—$C_6H_4$ |
| 468 | $CH_3$ | $CH_3$ | 4-$NO_2$—$C_6H_4$ |
| 469 | $CH_3$ | $CH_3$ | 2,4-$(NO_2)_2$—$C_6H_3$ |
| 470 | $CH_3$ | $CH_3$ | 2-$CH_3$—$C_6H_4$ |
| 471 | $CH_3$ | $CH_3$ | 3-$CH_3$—$C_6H_4$ |
| 472 | $CH_3$ | $CH_3$ | 4-$CH_3$—$C_6H_4$ |
| 473 | $CH_3$ | $CH_3$ | 2,3-$(CH_3)_2$—$C_6H_3$ |
| 474 | $CH_3$ | $CH_3$ | 2,4-$(CH_3)_2$—$C_6H_3$ |
| 475 | $CH_3$ | $CH_3$ | 2,5-$(CH_3)_2$—$C_6H_3$ |
| 476 | $CH_3$ | $CH_3$ | 2,6-$(CH_3)_2$—$C_6H_3$ |
| 477 | $CH_3$ | $CH_3$ | 2-$C_6H_5$—$C_6H_4$ |
| 478 | $CH_3$ | $CH_3$ | 3-$C_6H_5$—$C_6H_4$ |
| 479 | $CH_3$ | $CH_3$ | 4-$C_6H_5$—$C_6H_4$ |
| 480 | $CH_3$ | $CH_3$ | 3-$OCH_3$—$C_6H_4$ |
| 481 | $CH_3$ | $CH_3$ | 4-$OCH_3$—$C_6H_4$ |
| 482 | $CH_3$ | $CH_3$ | 3-Acetyl-$C_6H_4$ |
| 483 | $CH_3$ | $CH_3$ | 4-Acetyl-$C_6H_4$ |
| 484 | $CH_3$ | $CH_3$ | 3-Methoxycarbonyl-$C_6H_4$ |
| 485 | $CH_3$ | $CH_3$ | 4-Methoxycarbonyl-$C_6H_4$ |
| 486 | $CH_3$ | $CH_3$ | 3-$CF_3$—$C_6H_4$ |
| 487 | $CH_3$ | $CH_3$ | 4-$CF_3$—$C_6H_4$ |
| 488 | $CH_3$ | $CH_3$ | 2-Naphthyl |
| 489 | $CH_3$ | $CH_3$ | 6-Chloropyridazin-3-yl |
| 490 | $CH_3$ | $CH_3$ | 5-Chloropyrazin-2-yl |
| 491 | $CH_3$ | $CH_3$ | Quinolin-2-yl |
| 492 | $CH_3$ | $CH_3$ | 2,5-Dimethylpyrazin-3-yl |
| 493 | $CH_3$ | $CH_3$ | Pyrazin-2-yl |
| 494 | $CH_3$ | $CH_3$ | 3-Chloropyrid-2-yl |
| 495 | $CH_3$ | $CH_3$ | 6-Chloropyrid-2-yl |
| 496 | $CH_3$ | $CH_3$ | 4-Trifluoromethy [sic], 6-Chloropyrid-2-yl |
| 497 | $CH_3$ | $CH_3$ | 4-Trifluoromethylpyrid-2-yl |
| 498 | $CH_3$ | $CH_3$ | 6-Trifluoromethylpyrid-2-yl |
| 499 | $CH_3$ | $CH_3$ | 6-Methoxypyrid-2-yl |
| 500 | $CH_3$ | $CH_3$ | 5-Chloropyrid-2-yl |
| 501 | $CH_3$ | $CH_3$ | Pyrid-2-yl |
| 502 | $CH_3$ | $CH_3$ | Benzothiazol-2-yl |
| 503 | $CH_3$ | $CH_3$ | 7-Chloroquinolin-4-yl |
| 504 | $CH_3$ | $CH_3$ | 3-Nitropyrid-2-yl |
| 505 | $CH_3$ | $CH_3$ | Pyrrol-3-yl |
| 506 | $CH_3$ | $CH_3$ | Pyrrol-2-yl |
| 507 | $CH_3$ | $CH_3$ | 2,6-Dioctylpyrid-4-yl |
| 508 | $CH_3$ | $CH_3$ | 5-Nitropyrid-2-yl |
| 509 | $CH_3$ | $CH_3$ | Pyrid-4-yl |
| 510 | $CH_3$ | $CH_3$ | Pyrid-3-yl |
| 511 | $CH_3$ | $CH_3$ | Pyrimidin-2-yl |
| 512 | $CH_3$ | $CH_3$ | Pyrimidin-4-yl |
| 513 | $CH_3$ | $CH_3$ | Quinazolin-4-yl |
| 514 | $CH_3$ | $CH_3$ | 6-Chloropyrimidin-4-yl |
| 515 | $CH_3$ | $CH_3$ | 6-Methoxypyrimidin-4-yl |
| 516 | $CH_3$ | $CH_3$ | 2,5,6-Trichloropyrimidin-4-yl |
| 517 | $CH_3$ | $CH_3$ | 2,6-Dimethylpyrimidin-4-yl |
| 518 | $CH_3$ | $CH_3$ | 2-Methyl, 6-Chloropyrimidin-4-yl |
| 519 | $CH_3$ | $CH_3$ | 2-Methyl, 6-Ethoxypyrimidin-4-yl |
| 520 | $CH_3$ | $CH_3$ | 4,5,6-Trichloropyrimidin-2-yl |
| 521 | $CH_3$ | $CH_3$ | 4,6-Dimethoxypyrimidin-2-yl |

TABLE A-continued

| No. | $R^3$ | $R^4$ | $R^5$ |
|---|---|---|---|
| 522 | $CH_3$ | $CH_3$ | 4,6-Dimethylpyrimidin-2-y1 |
| 523 | $CH_3$ | $CH_3$ | 4,6-Dichloropyrimidin-2-yl |
| 524 | $CH_3$ | $CH_3$ | 4-Methyl, 6-methoxypyrimidin-2-yl |
| 525 | $CH_3$ | $CH_3$ | 4-Chloro, 6-methoxypyrimidin-2-yl |
| 526 | $CH_3$ | $CH_3$ | 6-Chloroquinoxalin-2-yl |
| 527 | $CH_3$ | $CH_3$ | 3,6-Dichloro-1,2,4-triazin-5-yl |
| 528 | $CH_3$ | $CH_3$ | 4-Methoxy-1,3,5-triazin-2-yl |
| 529 | $CH_3$ | $CH_3$ | 4-Ethoxy-1,3,5-triazin-2-yl |
| 530 | $CH_3$ | $CH_3$ | 4,6-Dichloro-1,3,5-triazin-2-yl |
| 531 | $CH_3$ | $CH_3$ | 4-Ethoxy, 6-Chloro-1,3,5-triazin-2-yl |
| 532 | $CH_3$ | $CH_3$ | Isoxazol-3-yl |
| 533 | $CH_3$ | $CH_3$ | Thien-2-yl |
| 534 | $CH_3$ | $CH_3$ | Fur-2-yl |
| 535 | $CH_3$ | $CH_3$ | Thiatriazol-5-yl |
| 536 | $CH_3$ | $CH_3$ | (E)-1-Chloropropen-3-yl |
| 537 | $CH_3$ | $CH_3$ | (E)-4-(4'-Chlorophenyl)but-2-en-1-yl |
| 538 | $CH_3$ | $CH_3$ | Propyn-3-yl |
| 539 | $CH_3$ | $CH_3$ | Methylcarbonyl |
| 540 | $CH_3$ | $CH_3$ | Ethylcarbonyl |
| 541 | $CH_3$ | $CH_3$ | n-Propylcarbonyl |
| 542 | $CH_3$ | $CH_3$ | i-Propylcarbonyl |
| 543 | $CH_3$ | $CH_3$ | n-Butylcarbonyl |
| 544 | $CH_3$ | $CH_3$ | s-Butylcarbonyl |
| 545 | $CH_3$ | $CH_3$ | i-Butylcarbonyl |
| 546 | $CH_3$ | $CH_3$ | t-Butylcarbonyl |
| 547 | $CH_3$ | $CH_3$ | n-Pentylcarbonyl |
| 548 | $CH_3$ | $CH_3$ | i-Pentylcarbonyl |
| 549 | $CH_3$ | $CH_3$ | neo-Pentylcarbonyl |
| 550 | $CH_3$ | $CH_3$ | n-Hexylcarbonyl |
| 551 | $CH_3$ | $CH_3$ | n-Octylcarbonyl |
| 552 | $CH_3$ | $CH_3$ | 1-Propenylcarbonyl |
| 553 | $CH_3$ | $CH_3$ | 2-Penten-1-yl-carbonyl |
| 554 | $CH_3$ | $CH_3$ | 2,5-Heptadien-1-yl-carbonyl |
| 555 | $CH_3$ | $CH_3$ | Benzoyl |
| 556 | $CH_3$ | $CH_3$ | 2-Chlorobenzoyl |
| 557 | $CH_3$ | $CH_3$ | 3-Chlorobenzoyl |
| 558 | $CH_3$ | $CH_3$ | 4-Chlorobenzoyl |
| 559 | $CH_3$ | $CH_3$ | 2-Cyanobenzoyl |
| 560 | $CH_3$ | $CH_3$ | 3-Cyanobenzoyl |
| 561 | $CH_3$ | $CH_3$ | 4-Cyanobenzoyl |
| 562 | $CH_3$ | $CH_3$ | 4-Methoxybenzoyl |
| 563 | $CH_3$ | $CH_3$ | 2-Pyridylcarbonyl |
| 564 | $CH_3$ | $CH_3$ | 3-Pyridylcarbonyl |
| 565 | $CH_3$ | $CH_3$ | 4-Pyridylcarbonyl |
| 566 | $CH_3$ | $CH_3$ | 2-Pyrimidinylcarbonyl |
| 567 | $CH_3$ | $CH_3$ | 2-Oxazolylcarbonyl |
| 568 | $CH_3$ | $CH_3$ | 4-Methylisoxazol-5-yl-carbonyl |
| 569 | $CH_3$ | $CH_3$ | Methylsulfonyl |
| 570 | $CH_3$ | $CH_3$ | Ethylsulfonyl |
| 571 | $CH_3$ | $CH_3$ | n-Propylsulfonyl |
| 572 | $CH_3$ | $CH_3$ | i-Propylsulfonyl |
| 573 | $CH_3$ | $CH_3$ | n-Butylsulfonyl |
| 574 | $CH_3$ | $CH_3$ | t-Butylsulfonyl |
| 575 | $CH_3$ | $CH_3$ | n-Pentylsulfonyl |
| 576 | $CH_3$ | $CH_3$ | neo-Pentylsulfonyl |
| 577 | $CH_3$ | $CH_3$ | n-Hexylsulfonyl |
| 578 | $CH_3$ | $CH_3$ | n-Octylsulfonyl |
| 579 | $CH_3$ | $CH_3$ | Phenylsulfonyl |
| 580 | $CH_3$ | $CH_3$ | 2-Chlorophenylsulfonyl |
| 581 | $CH_3$ | $CH_3$ | 3-Chlorophenylsulfonyl |
| 582 | $CH_3$ | $CH_3$ | 4-Chlorophenylsulfonyl |
| 583 | $CH_3$ | $CH_3$ | 2-Cyanophenylsulfonyl |
| 584 | $CH_3$ | $CH_3$ | 3-Cyanophenylsulfonyl |
| 585 | $CH_3$ | $CH_3$ | 4-Cyanophenylsulfonyl |
| 586 | $CH_3$ | $CH_3$ | 2-Pyridylsulfonyl |
| 587 | $CH_3$ | $CH_3$ | 3-Pyridylsulfonyl |
| 588 | $CH_3$ | $CH_3$ | 4-Pyridylsulfonyl |
| 589 | $CH_3$ | $CH_3$ | 2-Pyrimidinylsulfonyl |
| 590 | $CH_3$ | $CH_3$ | 4-Oxazolylsulfonyl |

TABLE A-continued

| No. | $R^3$ | $R^4$ | $R^5$ |
|---|---|---|---|
| 591 | $CH_3$ | $CH_3$ | 5-Chlorothiazol-2-yl-sulfonyl |
| 592 | $CH_3$ | $CH_3$ | 2-t-$C_4H_9$—$C_6H_4$—$CH_2$ |
| 593 | $CH_3$ | $CH_3$ | 3-t-$C_4H_9$—$C_6H_4$—$CH_2$ |
| 594 | $CH_3$ | $CH_3$ | 4-t-$C_4H_9$—$C_6H_4$—$CH_2$ |
| 595 | $CH_3$ | $CH_3$ | 2-(4'-Chlorothiazol-2'-yl-oxy)eth-1-yl |
| 596 | $CH_3$ | $CH_3$ | 2-(1'-Methylpyrazol-4'-yl-oxy)eth-1-yl |
| 597 | $CH_3$ | $CH_3$ | 4-Br—$C_6H_4$ |
| 598 | $CH_3$ | $CH_3$ | 3,5-$(CH_3)_2$—$C_6H_3$ |
| 599 | $CH_3$ | $CH_3$ | 4-$C_2H_5$—$C_6H_4$ |
| 600 | $CH_3$ | $CH_3$ | 3-Dimethylaminocarbonyl-$C_6H_4$ |
| 601 | $CH_3$ | $CH_3$ | 4-Dimethylaminocarbonyl-$C_6H_4$ |
| 602 | $CH_3$ | $CH_3$ | 2-Hydroxyprop-1-yl |
| 603 | $CH_3$ | $CH_3$ | 6-Hydroxy-2-methyl-pyrimidin-4-ylmethyl |
| 604 | $CH_3$ | $CH_3$ | [6-OH, 2-$CH(CH_3)_2$-pyrimidin 4-yl]-$CH_2$ |
| 605 | $CH_3$ | $CH_3$ | [6-OH, 2-$CH(CH_2)_2$-pyrimidin-4-yl]-$CH_2$ |
| 606 | $CH_3$ | $CH_3$ | 5-(2'-Furan)-pent-1-yl |
| 607 | $CH_3$ | $CH_3$ | 5-(2'-N-Methylpyr-rol)-pent-1-yl |
| 608 | $CH_3$ | $CH_3$ | [2-(4-Cl—$C_6H_4$)-oxazol-4-yl]-$CH_2$ |
| 609 | $CH_3$ | $CH_3$ | 3-$CF_3$-pyridin-2-yl |
| 610 | $CH_3$ | $CH_3$ | 5-$CF_3$-pyridin-2-yl |
| 611 | $CH_3$ | $CH_3$ | 6-(2'-Thienyl)hex-1-yl |
| 612 | $CH_3$ | t-$C_4H_9$ | H |
| 613 | $CH_3$ | t-$C_4H_9$ | $CH_3$ |
| 614 | $CH_3$ | t-$C_4H_9$ | $C_2H_5$ |
| 615 | $CH_3$ | t-$C_4H_9$ | n-$C_3H_7$ |
| 616 | $CH_3$ | t-$C_4H_9$ | i-$C_3H_7$ |
| 617 | $CH_3$ | t-$C_4H_9$ | Cyclopropyl |
| 618 | $CH_3$ | t-$C_4H_9$ | n-$C_4H_9$ |
| 619 | $CH_3$ | t-$C_4H_9$ | t-$C_4H_9$ |
| 620 | $CH_3$ | t-$C_4H_9$ | n-$C_6H_{13}$ |
| 621 | $CH_3$ | t-$C_4H_9$ | (E)-1-Chloropropen-3-yl |
| 622 | $CH_3$ | t-$C_4H_9$ | Propyn-3-yl |
| 623 | $CH_3$ | t-$C_4H_9$ | 3-Methylbut-2-en-1-yl |
| 624 | $CH_3$ | t-$C_4H_9$ | 2-Naphthyl-$CH_2$ |
| 625 | $CH_3$ | t-$C_4H_9$ | 4-Cl—$C_6H_4$—$CH_2$ |
| 626 | $CH_3$ | t-$C_4H_9$ | (E)-4-(4'-Chlorophenyl)but-2-en-1-yl |
| 627 | $CH_3$ | t-$C_4H_9$ | 6-(4'-Chlorophenyl)hex-1-yl |
| 628 | $CH_3$ | t-$C_4H_9$ | 3-$CF_3$—$C_6H_4$ |
| 629 | $CH_3$ | $C_6H_5$ | H |
| 630 | $CH_3$ | $C_6H_5$ | $CH_3$ |
| 631 | $CH_3$ | $C_6H_5$ | $C_2H_5$ |
| 632 | $CH_3$ | $C_6H_5$ | n-$C_3H_7$ |
| 633 | $CH_3$ | $C_6H_5$ | i-$C_3H_7$ |
| 634 | $CH_3$ | $C_6H_5$ | Cyclopropyl |
| 635 | $CH_3$ | $C_6H_5$ | n-$C_4H_9$ |
| 636 | $CH_3$ | $C_6H_5$ | t-$C_4H_9$ |
| 637 | $CH_3$ | $C_6H_5$ | n-$C_6H_{13}$ |
| 638 | $CH_3$ | $C_6H_5$ | 4-Cl—$C_6H_4$—$CH_2$ |
| 639 | $CH_3$ | $C_6H_5$ | 3-$CF_3$—$C_6H_4$ |
| 640 | $CH_3$ | $C_6H_5$ | 6-(4'-Chlorophenyl)hex-1-yl |
| 641 | $CH_3$ | $C_6H_5$ | (E)-4-(4'-Chlorophenyl)but-2-en-1-yl |
| 642 | $CH_3$ | H | H |
| 643 | $CH_3$ | H | $CH_3$ |
| 644 | $CH_3$ | H | $C_2H_5$ |
| 645 | $CH_3$ | H | n-$C_3H_7$ |
| 646 | $CH_3$ | H | i-$C_3H_7$ |
| 647 | $CH_3$ | OH | H |
| 648 | $CH_3$ | OH | $CH_3$ |
| 649 | $CH_3$ | OH | $C_2H_5$ |
| 650 | $CH_3$ | OH | n-$C_3H_7$ |
| 651 | $CH_3$ | OH | i-$C_3H_7$ |
| 652 | $CH_3$ | Cl | $CH_3$ |
| 653 | $CH_3$ | Cl | $C_2H_5$ |
| 654 | $CH_3$ | Cl | n-$C_3H_7$ |
| 655 | $CH_3$ | Cl | i-$C_3H_7$ |
| 656 | $CH_3$ | $OCH_3$ | H |
| 657 | $CH_3$ | $OCH_3$ | $CH_3$ |

TABLE A-continued

| No. | $R^3$ | $R^4$ | $R^5$ |
|---|---|---|---|
| 658 | $CH_3$ | $OCH_3$ | $C_2H_5$ |
| 659 | $CH_3$ | $OCH_3$ | n-$C_3H_7$ |
| 660 | $CH_3$ | $OCH_3$ | i-$C_3H_7$ |
| 661 | $CH_3$ | $SCH_3$ | H |
| 662 | $CH_3$ | $SCH_3$ | $CH_3$ |
| 663 | $CH_3$ | $SCH_3$ | $C_2H_5$ |
| 664 | $CH_3$ | $SCH_3$ | n-$C_3H_7$ |
| 665 | $CH_3$ | $SCH_3$ | i-$C_3H_7$ |
| 666 | $CH_3$ | Cyclopropyl | H |
| 667 | $CH_3$ | Cyclopropyl | $CH_3$ |
| 668 | $CH_3$ | Cyclopropyl | $C_2H_5$ |
| 669 | $CH_3$ | Cyclopropyl | n-$C_3H_7$ |
| 670 | $CH_3$ | Cyclopropyl | i-$C_3H_7$ |
| 671 | $CH_3$ | 2-Pyridyl | H |
| 672 | $CH_3$ | 2-Pyridyl | $CH_3$ |
| 673 | $CH_3$ | 2-Pyridyl | $C_2H_5$ |
| 674 | $CH_3$ | 2-Pyridyl | n-$C_3H_7$ |
| 675 | $CH_3$ | 2-Pyridyl | i-$C_3H_7$ |
| 676 | $CH_3$ | 3-Pyridyl | H |
| 677 | $CH_3$ | 3-Pyridyl | $CH_3$ |
| 678 | $CH_3$ | 3-Pyridyl | $C_2H_5$ |
| 679 | $CH_3$ | 3-Pyridyl | n-$C_3H_7$ |
| 680 | $CH_3$ | 3-Pyridyl | i-$C_3H_7$ |
| 681 | $CH_3$ | 4-Pyridyl | H |
| 682 | $CH_3$ | 4-Pyridyl | $CH_3$ |
| 683 | $CH_3$ | 4-Pyridyl | $C_2H_5$ |
| 684 | $CH_3$ | 4-Pyridyl | n-$C_3H_7$ |
| 685 | $CH_3$ | 4-Pyridyl | i-$C_3H_7$ |
| 686 | $CH_3$ | 2-Pyridimidyl | H |
| 687 | $CH_3$ | 2-Pyridimidyl | $CH_3$ |
| 688 | $CH_3$ | 2-Pyridimidyl | $C_2H_5$ |
| 689 | $CH_3$ | 2-Pyridimidyl | n-$C_3H_7$ |
| 690 | $CH_3$ | 2-Pyridimidyl | i-$C_3H_7$ |
| 691 | $CH_3$ | 4-Pyridimidy | H |
| 692 | $CH_3$ | 4-Pyridimidyl | $CH_3$ |
| 693 | $CH_3$ | 4-Pyridimidyl | $C_2H_5$ |
| 694 | $CH_3$ | 4-Pyridimidyl | n-$C_3H_7$ |
| 695 | $CH_3$ | 4-Pyridimidyl | i-$C_3H_7$ |
| 696 | $CH_3$ | 5-Pyridimidyl | H |
| 697 | $CH_3$ | 5-Pyridimidyl | $CH_3$ |
| 698 | $CH_3$ | 5-Pyridimidyl | $C_2H_5$ |
| 699 | $CH_3$ | 5-Pyridimidyl | n-$C_3H_7$ |
| 700 | $CH_3$ | 5-Pyridimidyl | i-$C_3H_7$ |
| 701 | $CH_3$ | 1,3,5-Triazinyl | H |
| 702 | $CH_3$ | 1,3,5-Triazinyl | $CH_3$ |
| 703 | $CH_3$ | 1,3,5-Triazinyl | $C_2H_5$ |
| 704 | $CH_3$ | 1,3,5-Triazinyl | n-$C_3H_7$ |
| 705 | $CH_3$ | 1,3,5-Triazinyl | i-$C_3H_7$ |
| 706 | $CH_3$ | 2-Furyl | H |
| 707 | $CH_3$ | 2-Furyl | $CH_3$ |
| 708 | $CH_3$ | 2-Furyl | $C_2H_5$ |
| 709 | $CH_3$ | 2-Furyl | n-$C_3H_7$ |
| 710 | $CH_3$ | 2-Furyl | i-$C_3H_7$ |
| 711 | $CH_3$ | 3-Furyl | H |
| 712 | $CH_3$ | 3-Furyl | $CH_3$ |
| 713 | $CH_3$ | 3-Furyl | $C_2H_5$ |
| 714 | $CH_3$ | 3-Furyl | n-$C_3H_7$ |
| 715 | $CH_3$ | 3-Furyl | i-$C_3H_7$ |
| 716 | $CH_3$ | 2-Thienyl | H |
| 717 | $CH_3$ | 2-Thienyl | $CH_3$ |
| 718 | $CH_3$ | 2-Thienyl | $C_2H_5$ |
| 719 | $CH_3$ | 2-Thienyl | n-$C_3H_7$ |
| 720 | $CH_3$ | 2-Thienyl | i-$C_3H_7$ |
| 721 | $CH_3$ | 3-Thienyl | H |
| 722 | $CH_3$ | 3-Thienyl | $CH_3$ |
| 723 | $CH_3$ | 3-Thienyl | $C_2H_5$ |
| 724 | $CH_3$ | 3-Thienyl | n-$C_3H_7$ |
| 725 | $CH_3$ | 3-Thienyl | i-$C_3H_7$ |
| 726 | $CH_3$ | 2-Oxazolyl | H |
| 727 | $CH_3$ | 2-Oxazolyl | $CH_3$ |
| 728 | $CH_3$ | 2-Oxazolyl | $C_2H_5$ |
| 729 | $CH_3$ | 2-Oxazolyl | n-$C_3H_7$ |
| 730 | $CH_3$ | 2-Oxazolyl | i-$C_3H_7$ |
| 731 | $CH_3$ | 4-Oxazolyl | H |
| 732 | $CH_3$ | 4-Oxazolyl | $CH_3$ |
| 733 | $CH_3$ | 4-Oxazolyl | $C_2H_5$ |
| 734 | $CH_3$ | 4-Oxazolyl | n-$C_3H_7$ |

TABLE A-continued

| No. | $R^3$ | $R^4$ | $R^5$ |
|---|---|---|---|
| 735 | $CH_3$ | 4-Oxazolyl | $i-C_3H_7$ |
| 736 | $CH_3$ | 2-Thiazolyl | H |
| 737 | $CH_3$ | 2-Thiazolyl | $CH_3$ |
| 738 | $CH_3$ | 2-Thiazolyl | $C_2H_5$ |
| 739 | $CH_3$ | 2-Thiazolyl | $n-C_3H_7$ |
| 740 | $CH_3$ | 2-Thiazolyl | $i-C_3H_7$ |
| 741 | $CH_3$ | 4-Thiazolyl | H |
| 742 | $CH_3$ | 4-Thiazolyl | $CH_3$ |
| 743 | $CH_3$ | 4-Thiazolyl | $C_2H_5$ |
| 744 | $CH_3$ | 4-Thiazolyl | $n-C_3H_7$ |
| 745 | $CH_3$ | 4-Thiazolyl | $i-C_3H_7$ |
| 746 | $CH_3$ | 3-Isoxazolyl | H |
| 747 | $CH_3$ | 3-Isoxazolyl | $CH_3$ |
| 748 | $CH_3$ | 3-Isoxazolyl | $C_2H_5$ |
| 749 | $CH_3$ | 3-Isoxazolyl | $n-C_3H_7$ |
| 750 | $CH_3$ | 3-Isoxazolyl | $i-C_3H_7$ |
| 751 | $CH_3$ | 5-Isoxazolyl | H |
| 752 | $CH_3$ | 5-Isoxazolyl | $CH_3$ |
| 753 | $CH_3$ | 5-Isoxazolyl | $C_2H_5$ |
| 754 | $CH_3$ | 5-Isoxazolyl | $n-C_3H_7$ |
| 755 | $CH_3$ | 5-Isoxazolyl | $i-C_3H_7$ |
| 756 | $CH_3$ | 2-Imidazolyl | H |
| 757 | $CH_3$ | 2-Imidazolyl | $CH_3$ |
| 758 | $CH_3$ | 2-Imidazolyl | $C_2H_5$ |
| 759 | $CH_3$ | 2-Imidazolyl | $n-C_3H_7$ |
| 760 | $CH_3$ | 2-Imidazolyl | $i-C_3H_7$ |
| 761 | $CH_3$ | 3-Pyrazolyl | H |
| 762 | $CH_3$ | 3-Pyrazolyl | $CH_3$ |
| 763 | $CH_3$ | 3-Pyrazolyl | $C_2H_5$ |
| 764 | $CH_3$ | 3-Pyrazolyl | $n-C_3H_7$ |
| 765 | $CH_3$ | 3-Pyrazolyl | $i-C_3H_7$ |
| 766 | $CH_3$ | 4-Pyrazolyl | H |
| 767 | $CH_3$ | 4-Pyrazolyl | $CH_3$ |
| 768 | $CH_3$ | 4-Pyrazolyl | $C_2H_5$ |
| 769 | $CH_3$ | 4-Pyrazolyl | $n-C_3H_7$ |
| 770 | $CH_3$ | 4-Pyrazolyl | $i-C_3H_7$ |
| 771 | $OCH_3$ | H | H |
| 772 | $OCH_3$ | H | $CH_3$ |
| 773 | $OCH_3$ | H | $C_2H_5$ |
| 774 | $OCH_3$ | H | $n-C_3H_7$ |
| 775 | $OCH_3$ | H | $i-C_3H_7$ |
| 776 | $OCH_3$ | OH | H |
| 777 | $OCH_3$ | OH | $CH_3$ |
| 778 | $OCH_3$ | OH | $C_2H_5$ |
| 779 | $OCH_3$ | OH | $n-C_3H_7$ |
| 780 | $OCH_3$ | OH | $i-C_3H_7$ |
| 781 | $OCH_3$ | Cl | $n-C_4H_9$ |
| 782 | $OCH_3$ | Cl | $CH_3$ |
| 783 | $OCH_3$ | Cl | $C_2H_5$ |
| 784 | $OCH_3$ | Cl | $n-C_3H_7$ |
| 785 | $OCH_3$ | Cl | $i-C_3H_7$ |
| 786 | $OCH_3$ | $OCH_3$ | H |
| 787 | $OCH_3$ | $OCH_3$ | $CH_3$ |
| 788 | $OCH_3$ | $OCH_3$ | $C_2H_5$ |
| 789 | $OCH_3$ | $OCH_3$ | $n-C_3H_7$ |
| 790 | $OCH_3$ | $OCH_3$ | $i-C_3H_7$ |
| 791 | $OCH_3$ | $SCH_3$ | H |
| 792 | $OCH_3$ | $SCH_3$ | $CH_3$ |
| 793 | $OCH_3$ | $SCH_3$ | $C_2H_5$ |
| 794 | $OCH_3$ | $SCH_3$ | $n-C_3H_7$ |
| 795 | $OCH_3$ | $SCH_3$ | $i-C_3H_7$ |
| 796 | $OCH_3$ | $CH_3$ | H |
| 797 | $OCH_3$ | $CH_3$ | $CH_3$ |
| 798 | $OCH_3$ | $CH_3$ | $C_2H_5$ |
| 799 | $OCH_3$ | $CH_3$ | $n-C_3H_7$ |
| 800 | $OCH_3$ | $CH_3$ | $i-C_3H_7$ |
| 801 | $OCH_3$ | Cyclopropyl | H |
| 802 | $OCH_3$ | Cyclopropyl | $CH_3$ |
| 803 | $OCH_3$ | Cyclopropyl | $C_2H_5$ |
| 804 | $OCH_3$ | Cyclopropyl | $n-C_3H_7$ |
| 805 | $OCH_3$ | Cyclopropyl | $i-C_3H_7$ |
| 806 | $OCH_3$ | 2-Pyridyl | H |
| 807 | $OCH_3$ | 2-Pyridyl | $CH_3$ |
| 808 | $OCH_3$ | 2-Pyridyl | $C_2H_5$ |
| 809 | $OCH_3$ | 2-Pyridyl | $n-C_3H_7$ |
| 810 | $OCH_3$ | 2-Pyridyl | $i-C_3H_7$ |
| 811 | $OCH_3$ | 3-Pyridyl | H |

TABLE A-continued

| No. | $R^3$ | $R^4$ | $R^5$ |
|---|---|---|---|
| 812 | $OCH_3$ | 3-Pyridyl | $CH_3$ |
| 813 | $OCH_3$ | 3-Pyridyl | $C_2H_5$ |
| 814 | $OCH_3$ | 3-Pyridyl | $n-C_3H_7$ |
| 815 | $OCH_3$ | 3-Pyridyl | $i-C_3H_7$ |
| 816 | $OCH_3$ | 4-Pyridyl | H |
| 817 | $OCH_3$ | 4-Pyridyl | $CH_3$ |
| 818 | $OCH_3$ | 4-Pyridyl | $C_2H_5$ |
| 819 | $OCH_3$ | 4-Pyridyl | $n-C_3H_7$ |
| 820 | $OCH_3$ | 4-Pyrimidyl | $i-C_3H_7$ |
| 821 | $OCH_3$ | 2-Pyrimidyl | H |
| 822 | $OCH_3$ | 2-Pyrimidyl | $CH_3$ |
| 823 | $OCH_3$ | 2-Pyrimidyl | $C_2H_5$ |
| 824 | $OCH_3$ | 2-Pyrimidyl | $n-C_3H_7$ |
| 825 | $OCH_3$ | 2-Pyrimidyl | $i-C_3H_7$ |
| 826 | $OCH_3$ | 4-Pyrimidyl | H |
| 827 | $OCH_3$ | 4-Pyrimidyl | $CH_3$ |
| 828 | $OCH_3$ | 4-Pyrimidyl | $C_2H_5$ |
| 829 | $OCH_3$ | 4-Pyrimidyl | $n-C_3H_7$ |
| 830 | $OCH_3$ | 4-Pyrimidyl | $i-C_3H_7$ |
| 831 | $OCH_3$ | 5-Pyrimidyl | H |
| 832 | $OCH_3$ | 5-Pyrimidyl | $CH_3$ |
| 833 | $OCH_3$ | 5-Pyrimidyl | $C_2H_5$ |
| 834 | $OCH_3$ | 5-Pyrimidyl | $n-C_3H_7$ |
| 835 | $OCH_3$ | 5-Pyrimidyl | $i-C_3H_7$ |
| 836 | $OCH_3$ | 1,3,5-Triazinyl | H |
| 837 | $OCH_3$ | 1,3,5-Triazinyl | $CH_3$ |
| 838 | $OCH_3$ | 1,3,5-Triazinyl | $C_2H_5$ |
| 839 | $OCH_3$ | 1,3,5-Triazinyl | $n-C_3H_7$ |
| 840 | $OCH_3$ | 1,3,5-Triazinyl | $i-C_3H_7$ |
| 841 | $OCH_3$ | 2-Furyl | H |
| 842 | $OCH_3$ | 2-Furyl | $CH_3$ |
| 843 | $OCH_3$ | 2-Furyl | $C_2H_5$ |
| 844 | $OCH_3$ | 2-Furyl | $n-C_3H_7$ |
| 845 | $OCH_3$ | 2-Furyl | $i-C_3H_7$ |
| 846 | $OCH_3$ | 3-Furyl | H |
| 847 | $OCH_3$ | 3-Furyl | $CH_3$ |
| 848 | $OCH_3$ | 3-Furyl | $C_2H_5$ |
| 849 | $OCH_3$ | 3-Furyl | $n-C_3H_7$ |
| 850 | $OCH_3$ | 3-Furyl | $i-C_3H_7$ |
| 851 | $OCH_3$ | 2-Thienyl | H |
| 852 | $OCH_3$ | 2-Thienyl | $CH_3$ |
| 853 | $OCH_3$ | 2-Thienyl | $C_2H_5$ |
| 854 | $OCH_3$ | 2-Thienyl | $n-C_3H_7$ |
| 855 | $OCH_3$ | 2-Thienyl | $i-C_3H_7$ |
| 856 | $OCH_3$ | 3-Thienyl | H |
| 857 | $OCH_3$ | 3-Thienyl | $CH_3$ |
| 858 | $OCH_3$ | 3-Thienyl | $C_2H_5$ |
| 859 | $OCH_3$ | 3-Thienyl | $n-C_3H_7$ |
| 860 | $OCH_3$ | 3-Thienyl | $i-C_3H_7$ |
| 861 | $OCH_3$ | 2-Oxazolyl | H |
| 862 | $OCH_3$ | 2-Oxazolyl | $CH_3$ |
| 863 | $OCH_3$ | 2-Oxazolyl | $C_2H_5$ |
| 864 | $OCH_3$ | 2-Oxazolyl | $n-C_3H_7$ |
| 865 | $OCH_3$ | 2-Oxazolyl | $i-C_3H_7$ |
| 866 | $OCH_3$ | 4-Oxazolyl | H |
| 867 | $OCH_3$ | 4-Oxazolyl | $CH_3$ |
| 868 | $OCH_3$ | 4-Oxazolyl | $C_2H_5$ |
| 869 | $OCH_3$ | 4-Oxazolyl | $n-C_3H_7$ |
| 870 | $OCH_3$ | 4-Oxazolyl | $i-C_3H_7$ |
| 871 | $OCH_3$ | 2-Thiazolyl | H |
| 872 | $OCH_3$ | 2-Thiazolyl | $CH_3$ |
| 873 | $OCH_3$ | 2-Thiazolyl | $C_2H_5$ |
| 874 | $OCH_3$ | 2-Thiazolyl | $n-C_3H_7$ |
| 875 | $OCH_3$ | 2-Thiazolyl | $i-C_3H_7$ |
| 876 | $OCH_3$ | 4-Thiazolyl | H |
| 877 | $OCH_3$ | 4-Thiazolyl | $CH_3$ |
| 878 | $OCH_3$ | 4-Thiazolyl | $C_2H_5$ |
| 879 | $OCH_3$ | 4-Thiazolyl | $n-C_3H_7$ |
| 880 | $OCH_3$ | 4-Thiazolyl | $i-C_3H_7$ |
| 881 | $OCH_3$ | 3-Isoxazolyl | H |
| 882 | $OCH_3$ | 3-Isoxazolyl | $CH_3$ |
| 883 | $OCH_3$ | 3-Isoxazolyl | $C_2H_5$ |
| 884 | $OCH_3$ | 3-Isoxazolyl | $n-C_3H_7$ |
| 885 | $OCH_3$ | 3-Isoxazolyl | $i-C_3H_7$ |
| 886 | $OCH_3$ | 5-Isoxazolyl | H |
| 887 | $OCH_3$ | 5-Isoxazolyl | $CH_3$ |
| 888 | $OCH_3$ | 5-Isoxazolyl | $C_2H_5$ |

TABLE A-continued

| No. | $R^3$ | $R^4$ | $R^5$ |
|---|---|---|---|
| 889 | $OCH_3$ | 5-Isoxazolyl | n-$C_3H_7$ |
| 890 | $OCH_3$ | 5-Isoxazolyl | i-$C_3H_7$ |
| 891 | $OCH_3$ | 2-Imidazolyl | H |
| 892 | $OCH_3$ | 2-Imidazolyl | $CH_3$ |
| 893 | $OCH_3$ | 2-Imidazolyl | $C_2H_5$ |
| 894 | $OCH_3$ | 2-Imidazolyl | n-$C_3H_7$ |
| 895 | $OCH_3$ | 2-Imidazolyl | i-$C_3H_7$ |
| 896 | $OCH_3$ | 3-Pyrazolyl | H |
| 897 | $OCH_3$ | 3-Pyrazoly1 | $CH_3$ |
| 898 | $OCH_3$ | 3-Pyrazolyl | $C_2H_5$ |
| 899 | $OCH_3$ | 3-Pyrazolyl | n-$C_3H_7$ |
| 900 | $OCH_3$ | 3-Pyrazolyl | i-$C_3H_7$ |
| 901 | $OCH_3$ | 4-Pyrazolyl | H |
| 902 | $OCH_3$ | 4-Pyrazolyl | $CH_3$ |
| 903 | $OCH_3$ | 4-Pyrazolyl | $C_2H_5$ |
| 904 | $OCH_3$ | 4-Pyrazolyl | n-$C_3H_7$ |
| 905 | $OCH_3$ | 4-Pyrazolyl | i-$C_3H_7$ |
| 906 | OH | H | H |
| 907 | OH | H | $CH_3$ |
| 908 | OH | H | $C_2H_5$ |
| 909 | OH | H | n-$C_3H_7$ |
| 910 | OH | H | i-$C_3H_7$ |
| 911 | OH | OH | H |
| 912 | OH | OH | $CH_3$ |
| 913 | OH | OH | $C_2H_5$ |
| 914 | OH | OH | n-$C_3H_7$ |
| 915 | OH | OH | i-$C_3H_7$ |
| 916 | OH | Cl | n-$C_4H_9$ |
| 917 | OH | Cl | $CH_3$ |
| 918 | OH | Cl | $C_2H_5$ |
| 919 | OH | Cl | n-$C_3H_7$ |
| 920 | OH | Cl | i-$C_3H_7$ |
| 921 | OH | $OCH_3$ | H |
| 922 | OH | $OCH_3$ | $CH_3$ |
| 923 | OH | $OCH_3$ | $C_2H_5$ |
| 924 | OH | $OCH_3$ | n-$C_3H_7$ |
| 925 | OH | $OCH_3$ | i-$C_3H_7$ |
| 926 | OH | $SCH_3$ | H |
| 927 | OH | $SCH_3$ | $CH_3$ |
| 928 | OH | $SCH_3$ | $C_2H_5$ |
| 929 | OH | $SCH_3$ | n-$C_3H_7$ |
| 930 | OH | $SCH_3$ | i-$C_3H_7$ |
| 931 | OH | $CH_3$ | H |
| 932 | OH | $CH_3$ | $CH_3$ |
| 933 | OH | $CH_3$ | $C_2H_5$ |
| 934 | OH | $CH_3$ | n-$C_3H_7$ |
| 935 | OH | $CH_3$ | i-$C_3H_7$ |
| 936 | OH | Cyclopropyl | H |
| 937 | OH | Cyclopropyl | $CH_3$ |
| 938 | OH | Cyclopropyl | $C_2H_5$ |
| 939 | OH | Cyclopropyl | n-$C_3H_7$ |
| 940 | OH | Cyclopropyl | i-$C_3H_7$ |
| 941 | OH | 2-Pyridyl | H |
| 942 | OH | 2-Pyridyl | $CH_3$ |
| 943 | OH | 2-Pyridyl | $C_2H_5$ |
| 944 | OH | 2-Pyridyl | n-$C_3H_7$ |
| 945 | OH | 2-Pyridyl | i-$C_3H_7$ |
| 946 | OH | 3-Pyridyl | H |
| 947 | OH | 3-Pyridyl | $CH_3$ |
| 948 | OH | 3-Pyridyl | $C_2H_5$ |
| 949 | OH | 3-Pyridyl | n-$C_3H_7$ |
| 950 | OH | 3-Pyridyl | i-$C_3H_7$ |
| 951 | OH | 4-Pyridyl | H |
| 952 | OH | 4-Pyridyl | $CH_3$ |
| 953 | OH | 4-Pyridyl | $C_2H_5$ |
| 954 | OH | 4-Pyridyl | n-$C_3H_7$ |
| 955 | OH | 4-Pyridyl | i-$C_3H_7$ |
| 956 | OH | 2-Pyrimidyl | H |
| 957 | OH | 2-Pyrimidyl | $CH_3$ |
| 958 | OH | 2-Pyrimidyl | $C_2H_5$ |
| 959 | OH | 2-Pyrimidyl | n-$C_3H_7$ |
| 960 | OH | 2-Pyrimidyl | i-$C_3H_7$ |
| 961 | OH | 4-Pyrimidyl | H |
| 962 | OH | 4-Pyrimidyl | $CH_3$ |
| 963 | OH | 4-Pyrimidyl | $C_2H_5$ |
| 964 | OH | 4-Pyrimidyl | n-$C_3H_7$ |
| 965 | OH | 4-Pyrimidyl | i-$C_3H_7$ |

TABLE A-continued

| No. | $R^3$ | $R^4$ | $R^5$ |
|---|---|---|---|
| 966 | OH | 5-Pyrimidyl | H |
| 967 | OH | 5-Pyrimidyl | $CH_3$ |
| 968 | OH | 5-Pyrimidyl | $C_2H_5$ |
| 969 | OH | 5-Pyrimidyl | n-$C_3H_7$ |
| 970 | OH | 5-Pyrimidyl | i-$C_3H_7$ |
| 971 | OH | 1,3,5-Triazinyl | H |
| 972 | OH | 1,3,5-Triazinyl | $CH_3$ |
| 973 | OH | 1,3,5-Triazinyl | $C_2H_5$ |
| 974 | OH | 1,3,5-Triazinyl | n-$C_3H_7$ |
| 975 | OH | 1,3,5-Triazinyl | i-$C_3H_7$ |
| 976 | OH | 2-Furyl | H |
| 977 | OH | 2-Furyl | $CH_3$ |
| 978 | OH | 2-Furyl | $C_2H_5$ |
| 979 | OH | 2-Furyl | n-$C_3H_7$ |
| 980 | OH | 2-Furyl | i-$C_3H_7$ |
| 981 | OH | 3-Furyl | H |
| 982 | OH | 3-Furyl | $CH_3$ |
| 983 | OH | 3-Furyl | $C_2H_5$ |
| 984 | OH | 3-Furyl | n-$C_3H_7$ |
| 985 | OH | 3-Furyl | i-$C_3H_7$ |
| 986 | OH | 2-Thienyl | H |
| 987 | OH | 2-Thienyl | $CH_3$ |
| 998 | OH | 2-Thienyl | $C_2H_5$ |
| 989 | OH | 2-Thienyl | n-$C_3H_7$ |
| 990 | OH | 2-Thienyl | i-$C_3H_7$ |
| 991 | OH | 3-Thienyl | H |
| 992 | OH | 3-Thienyl | $CH_3$ |
| 993 | OH | 3-Thienyl | $C_2H_5$ |
| 994 | OH | 3-Thienyl | n-$C_3H_7$ |
| 995 | OH | 3-Thienyl | i-$C_3H_7$ |
| 996 | OH | 2-Oxazolyl | H |
| 997 | OH | 2-Oxazolyl | $CH_3$ |
| 998 | OH | 2-Oxazolyl | $C_2H_5$ |
| 999 | OH | 2-Oxazolyl | n-$C_3H_7$ |
| 1000 | OH | 2-Oxazolyl | i-$C_3H_7$ |
| 1001 | OH | 4-Oxazolyl | H |
| 1002 | OH | 4-Oxazolyl | $CH_3$ |
| 1003 | OH | 4-Oxazolyl | $C_2H_5$ |
| 1004 | OH | 4-Oxazolyl | n-$C_3H_7$ |
| 1005 | OH | 2-Thiazolyl | i-$C_3H_7$ |
| 1006 | OH | 2-Thiazolyl | H |
| 1007 | OH | 2-Thiazolyl | $CH_3$ |
| 1008 | OH | 2-Thiazolyl | $C_2H_5$ |
| 1009 | OH | 2-Thiazolyl | n-$C_3H_7$ |
| 1010 | OH | 2-Thiazolyl | i-$C_3H_7$ |
| 1011 | OH | 4-Thiazolyl | H |
| 1012 | OH | 4-Thiazolyl | $CH_3$ |
| 1013 | OH | 4-Thiazolyl | $C_2H_5$ |
| 1014 | OH | 4-Isoxazolyl | n-$C_3H_7$ |
| 1015 | OH | 4-Isoxazolyl | i-$C_3H_7$ |
| 1016 | OH | 3-Isoxazolyl | H |
| 1017 | OH | 3-Isoxazolyl | $CH_3$ |
| 1018 | OH | 3-Isoxazolyl | $C_2H_5$ |
| 1019 | OH | 3-Isoxazolyl | n-$C_3H_7$ |
| 1020 | OH | 3-Isoxazolyl | i-$C_3H_7$ |
| 1021 | OH | 5-Isoxazolyl | H |
| 1022 | OH | 5-Isoxazolyl | $CH_3$ |
| 1023 | OH | 5-Isoxazolyl | $C_2H_5$ |
| 1024 | OH | 5-Isoxazolyl | n-$C_3H_7$ |
| 1025 | OH | 5-Isoxazolyl | i-$C_3H_7$ |
| 1026 | OH | 2-Imidazolyl | H |
| 1027 | OH | 2-Imidazolyl | $CH_3$ |
| 1028 | OH | 2-Imidazolyl | $C_2H_5$ |
| 1029 | OH | 2-Imidazolyl | n-$C_3H_7$ |
| 1030 | OH | 2-Imidazolyl | i-$C_3H_7$ |
| 1031 | OH | 3-Pyrazolyl | H |
| 1032 | OH | 3-Pyrazolyl | $CH_3$ |
| 1033 | OH | 3-Pyrazolyl | $C_2H_5$ |
| 1034 | OH | 3-Pyrazolyl | n-$C_3H_7$ |
| 1035 | OH | 3-Pyrazolyl | i-$C_3H_7$ |
| 1036 | OH | 4-Pyrazolyl | H |
| 1037 | OH | 4-Pyrazolyl | $CH_3$ |
| 1038 | OH | 4-Pyrazolyl | $C_2H_5$ |
| 1039 | OH | 4-Pyrazolyl | n-$C_3H_7$ |
| 1040 | OH | 4-Pyrazolyl | i-$C_3H_7$ |
| 1041 | H | H | H |
| 1042 | H | H | $CH_3$ |

TABLE A-continued

| No. | $R^3$ | $R^4$ | $R^5$ |
|---|---|---|---|
| 1043 | H | H | $C_2H_5$ |
| 1044 | H | H | n-$C_3H_7$ |
| 1045 | H | H | i-$C_3H_7$ |
| 1046 | H | OH | H |
| 1047 | H | OH | $CH_3$ |
| 1048 | H | OH | $C_2H_5$ |
| 1049 | H | OH | n-$C_3H_7$ |
| 1050 | H | OH | i-$C_3H_7$ |
| 1051 | H | Cl | n-$C_4H_9$ |
| 1052 | H | Cl | $CH_3$ |
| 1053 | H | Cl | $C_2H_5$ |
| 1054 | H | Cl | n-$C_3H_7$ |
| 1055 | H | Cl | i-$C_3H_7$ |
| 1056 | H | $OCH_3$ | H |
| 1057 | H | $OCH_3$ | $CH_3$ |
| 1058 | H | $OCH_3$ | $C_2H_5$ |
| 1059 | H | $OCH_3$ | n-$C_3H_7$ |
| 1060 | H | $OCH_3$ | i-$C_3H_7$ |
| 1061 | H | $CH_3$ | H |
| 1062 | H | $CH_3$ | $CH_3$ |
| 1063 | H | $CH_3$ | $C_2H_5$ |
| 1064 | H | $CH_3$ | n-$C_3H_7$ |
| 1065 | H | $CH_3$ | i-$C_3H_7$ |
| 1066 | H | Cyclopropyl | H |
| 1067 | H | Cyclopropyl | $CH_3$ |
| 1068 | H | Cyclopropyl | $C_2H_5$ |
| 1069 | H | Cyclopropyl | n-$C_3H_7$ |
| 1070 | H | Cyclopropyl | i-$C_3H_7$ |
| 1071 | Cl | H | H |
| 1072 | Cl | H | $CH_3$ |
| 1073 | Cl | H | $C_2H_5$ |
| 1074 | Cl | H | n-$C_3H_7$ |
| 1075 | Cl | H | i-$C_3H_7$ |
| 1076 | Cl | OH | H |
| 1077 | Cl | OH | $CH_3$ |
| 1078 | Cl | OH | $C_2H_5$ |
| 1079 | Cl | OH | n-$C_3H_7$ |
| 1080 | Cl | OH | i-$C_3H_7$ |
| 1081 | Cl | Cl | n-$C_4H_9$ |
| 1082 | Cl | Cl | $CH_3$ |
| 1083 | Cl | Cl | $C_2H_5$ |
| 1084 | Cl | Cl | n-$C_3H_7$ |
| 1085 | Cl | Cl | i-$C_3H_7$ |
| 1086 | Cl | $OCH_3$ | H |
| 1087 | Cl | $OCH_3$ | $CH_3$ |
| 1088 | Cl | $OCH_3$ | $C_2H_5$ |
| 1089 | Cl | $OCH_3$ | n-$C_3H_7$ |
| 1090 | Cl | $OCH_3$ | i-$C_3H_7$ |
| 1091 | Cl | $CH_3$ | H |
| 1092 | Cl | $CH_3$ | $CH_3$ |
| 1093 | Cl | $CH_3$ | $C_2H_5$ |
| 1094 | Cl | $CH_3$ | n-$C_3H_7$ |
| 1095 | Cl | $CH_3$ | i-$C_3H_7$ |
| 1096 | Cl | Cyclopropyl | H |
| 1097 | Cl | Cyclopropyl | $CH_3$ |
| 1098 | Cl | Cyclopropyl | $C_2H_5$ |
| 1099 | Cl | Cyclopropyl | n-$C_3H_7$ |
| 1100 | Cl | Cyclopropyl | i-$C_3H_7$ |
| 1101 | $SCH_3$ | H | H |
| 1102 | $SCH_3$ | H | $CH_3$ |
| 1103 | $SCH_3$ | H | $C_2H_5$ |
| 1104 | $SCH_3$ | H | n-$C_3H_7$ |
| 1105 | $SCH_3$ | H | i-$C_3H_7$ |
| 1106 | $SCH_3$ | OH | H |
| 1107 | $SCH_3$ | OH | $CH_3$ |
| 1108 | $SCH_3$ | OH | $C_2H_5$ |
| 1109 | $SCH_3$ | OH | n-$C_3H_7$ |
| 1110 | $SCH_3$ | OH | i-$C_3H_7$ |
| 1111 | $SCH_3$ | $CH_3$ | H |
| 1112 | $SCH_3$ | $CH_3$ | $CH_3$ |
| 1113 | $SCH_3$ | $CH_3$ | $C_2H_5$ |
| 1114 | $SCH_3$ | $CH_3$ | n-$C_3H_7$ |
| 1115 | $SCH_3$ | $CH_3$ | i-$C_3H_7$ |
| 1116 | $SCH_3$ | $SCH_3$ | H |
| 1117 | $SCH_3$ | $SCH_3$ | $CH_3$ |
| 1118 | $SCH_3$ | $SCH_3$ | $C_2H_5$ |
| 1119 | $SCH_3$ | $SCH_3$ | n-$C_3H_7$ |

TABLE A-continued

| No. | $R^3$ | $R^4$ | $R^5$ |
|---|---|---|---|
| 1120 | $SCH_3$ | $SCH_3$ | i-$C_3H_7$ |
| 1121 | $SCH_3$ | Cyclopropyl | H |
| 1122 | $SCH_3$ | Cyclopropyl | $CH_3$ |
| 1123 | $SCH_3$ | Cyclopropyl | $C_2H_5$ |
| 1124 | $SCH_3$ | Cyclopropyl | n-$C_3H_7$ |
| 1125 | $SCH_3$ | Cyclopropyl | i-$C_3H_7$ |
| 1126 | Cyclopropyl | H | H |
| 1127 | Cyclopropyl | H | $CH_3$ |
| 1128 | Cyclopropyl | H | $C_2H_5$ |
| 1129 | Cyclopropyl | H | n-$C_3H_7$ |
| 1130 | Cyclopropyl | H | i-$C_3H_7$ |
| 1131 | Cyclopropyl | OH | H |
| 1132 | Cyclopropyl | OH | $CH_3$ |
| 1133 | Cyclopropyl | OH | $C_2H_5$ |
| 1134 | Cyclopropyl | OH | n-$C_3H_7$ |
| 1135 | Cyclopropyl | OH | i-$C_3H_7$ |
| 1136 | Cyclopropyl | Cl | n-$C_4H_9$ |
| 1137 | Cyclopropyl | Cl | $CH_3$ |
| 1138 | Cyclopropyl | Cl | $C_2H_5$ |
| 1139 | Cyclopropyl | Cl | n-$C_3H_7$ |
| 1140 | Cyclopropyl | Cl | i-$C_3H_7$ |
| 1141 | Cyclopropyl | $OCH_3$ | H |
| 1142 | Cyclopropyl | $OCH_3$ | $CH_3$ |
| 1143 | Cyclopropyl | $OCH_3$ | $C_2H_5$ |
| 1144 | Cyclopropyl | $OCH_3$ | n-$C_3H_7$ |
| 1145 | Cyclopropyl | $OCH_3$ | i-$C_3H_7$ |
| 1146 | Cyclopropyl | $SCH_3$ | H |
| 1147 | Cyclopropyl | $SCH_3$ | $CH_3$ |
| 1148 | Cyclopropyl | $SCH_3$ | $C_2H_5$ |
| 1149 | Cyclopropyl | $SCH_3$ | n-$C_3H_7$ |
| 1150 | Cyclopropyl | $SCH_3$ | i-$C_3H_7$ |
| 1151 | Cyclopropyl | $CH_3$ | H |
| 1152 | Cyclopropyl | $CH_3$ | $CH_3$ |
| 1153 | Cyclopropyl | $CH_3$ | $C_2H_5$ |
| 1154 | Cyclopropyl | $CH_3$ | n-$C_3H_7$ |
| 1155 | Cyclopropyl | $CH_3$ | i-$C_3H_7$ |
| 1156 | $CH_3$ | 2-F—$C_6H_4$ | $CH_3$ |
| 1157 | $CH_3$ | 2-F—$C_6H_4$ | $C_2H_5$ |
| 1158 | $CH_3$ | 2-F—$C_6H_4$ | n-$C_3H_7$ |
| 1159 | $CH_3$ | 2-F—$C_6H_4$ | i-$C_3H_7$ |
| 1160 | $CH_3$ | 2-F—$C_6H_4$ | n-$C_4H_9$ |
| 1161 | $CH_3$ | 2-F—$C_6H_4$ | t-$C_4H_9$ |
| 1162 | $CH_3$ | 2-F—$C_6H_4$ | n-$C_6H_{13}$ |
| 1163 | $CH_3$ | 2-F—$C_6H_4$ | Prop-1-en-3-yl |
| 1164 | $CH_3$ | 2-F—$C_6H_4$ | (E)-1-Chloroprop-1-en-3-yl |
| 1165 | $CH_3$ | 2-F—$C_6H_4$ | Propyn-3-yl |
| 1166 | $CH_3$ | 2-F—$C_6H_4$ | 3-Methyl-but-2-en-1-yl |

TABLE A-continued

| No. | $R^3$ | $R^4$ | $R^5$ |
|---|---|---|---|
| 1167 | $CH_3$ | 3-F—$C_6H_4$ | H |
| 1168 | $CH_3$ | 3-F—$C_6H_4$ | $CH_3$ |
| 1169 | $CH_3$ | 3-F—$C_6H_4$ | $C_2H_5$ |
| 1170 | $CH_3$ | 3-F—$C_6H_4$ | n-$C_3H_7$ |
| 1171 | $CH_3$ | 3-F—$C_6H_4$ | i-$C_3H_7$ |
| 1172 | $CH_3$ | 3-F—$C_6H_4$ | n-$C_4H_9$ |
| 1173 | $CH_3$ | 3-F—$C_6H_4$ | t-$C_4H_9$ |
| 1174 | $CH_3$ | 3-F—$C_6H_4$ | n-$C_6H_{13}$ |
| 1175 | $CH_3$ | 3-F—$C_6H_4$ | Prop-1-en-3-yl |
| 1176 | $CH_3$ | 3-F—$C_6H_4$ | (E)-1-Chloroprop-1-en-3-yl |
| 1177 | $CH_3$ | 3-F—$C_6H_4$ | Propyn-3-yl |
| 1178 | $CH_3$ | 3-F—$C_6H_4$ | 3-Methyl-but-2-en-1-yl |
| 1179 | $CH_3$ | 4-F—$C_6H_4$ | H |
| 1180 | $CH_3$ | 4-F—$C_6H_4$ | $CH_3$ |
| 1181 | $CH_3$ | 4-F—$C_6H_4$ | $C_2H_5$ |
| 1182 | $CH_3$ | 4-F—$C_6H_4$ | n-$C_3H_7$ |
| 1183 | $CH_3$ | 4-F—$C_6H_4$ | i-$C_3H_7$ |
| 1184 | $CH_3$ | 4-F—$C_6H_4$ | n-$C_4H_9$ |
| 1185 | $CH_3$ | 4-F—$C_6H_4$ | t-$C_4H_9$ |
| 1186 | $CH_3$ | 4-F—$C_6H_4$ | n-$C_6H_{13}$ |
| 1187 | $CH_3$ | 4-F—$C_6H_4$ | Prop-1-en-3-yl |
| 1188 | $CH_3$ | 4-F—$C_6H_4$ | (E)-1-Chloroprop-1-en-3-yl |
| 1189 | $CH_3$ | 4-F—$C_6H_4$ | Propyn-3-yl |
| 1190 | $CH_3$ | 4-F—$C_6H_4$ | 3-Methyl-but-2-en-1-yl |
| 1191 | $CH_3$ | 2-Cl—$C_6H_4$ | H |
| 1192 | $CH_3$ | 2-Cl—$C_6H_4$ | $CH_3$ |
| 1193 | $CH_3$ | 2-Cl—$C_6H_4$ | $C_2H_5$ |
| 1194 | $CH_3$ | 2-Cl—$C_6H_4$ | n-$C_3H_7$ |
| 1195 | $CH_3$ | 2-Cl—$C_6H_4$ | i-$C_3H_7$ |
| 1196 | $CH_3$ | 2-Cl—$C_6H_4$ | n-$C_4H_9$ |
| 1197 | $CH_3$ | 2-Cl—$C_6H_4$ | t-$C_4H_9$ |
| 1198 | $CH_3$ | 2-Cl—$C_6H_4$ | n-$C_6H_{13}$ |
| 1199 | $CH_3$ | 2-Cl—$C_6H_4$ | Prop-1-en-3-yl |
| 1200 | $CH_3$ | 2-Cl—$C_6H_4$ | (E)-1-Chloroprop-1-en-3-yl |
| 1201 | $CH_3$ | 2-Cl—$C_6H_4$ | Propyn-3-yl |
| 1202 | $CH_3$ | 2-Cl—$C_6H_4$ | 3-Methyl-but-2-en-1-yl |
| 1203 | $CH_3$ | 3-Cl—$C_6H_4$ | H |
| 1204 | $CH_3$ | 3-Cl—$C_6H_4$ | $CH_3$ |
| 1205 | $CH_3$ | 3-Cl—$C_6H_4$ | $C_2H_5$ |
| 1206 | $CH_3$ | 3-Cl—$C_6H_4$ | n-$C_3H_7$ |
| 1207 | $CH_3$ | 3-Cl—$C_6H_4$ | i-$C_3H_7$ |
| 1208 | $CH_3$ | 3-Cl—$C_6H_4$ | n-$C_4H_9$ |
| 1209 | $CH_3$ | 3-Cl—$C_6H_4$ | t-$C_4H_9$ |
| 1210 | $CH_3$ | 3-Cl—$C_6H_4$ | n-$C_6H_{13}$ |
| 1211 | $CH_3$ | 3-Cl—$C_6H_4$ | Prop-1-en-3-yl |
| 1212 | $CH_3$ | 3-Cl—$C_6H_4$ | (E)-1-Chloroprop-1-en-3-yl |
| 1213 | $CH_3$ | 3-Cl—$C_6H_4$ | Propyn-3-yl |
| 1214 | $CH_3$ | 3-Cl—$C_6H_4$ | 3-Methyl-but-2-en-1-yl |
| 1215 | $CH_3$ | 4-Cl—$C_6H_4$ | H |
| 1216 | $CH_3$ | 4-Cl—$C_6H_4$ | $CH_3$ |
| 1217 | $CH_3$ | 4-Cl—$C_6H_4$ | $C_2H_5$ |
| 1218 | $CH_3$ | 4-Cl—$C_6H_4$ | n-$C_3H_7$ |
| 1219 | $CH_3$ | 4-Cl—$C_6H_4$ | i-$C_3H_7$ |
| 1220 | $CH_3$ | 4-Cl—$C_6H_4$ | n-$C_4H_9$ |
| 1221 | $CH_3$ | 4-Cl—$C_6H_4$ | t-$C_4H_9$ |
| 1222 | $CH_3$ | 4-Cl—$C_6H_4$ | n-$C_6H_{13}$ |
| 1223 | $CH_3$ | 4-Cl—$C_6H_4$ | Prop-1-en-3-yl |
| 1224 | $CH_3$ | 4-Cl—$C_6H_4$ | (E)-1-Chloroprop-1-en-3-yl |
| 1225 | $CH_3$ | 4-Cl—$C_6H_4$ | Propyn-3-yl |
| 1226 | $CH_3$ | 4-Cl—$C_6H_4$ | 3-Methyl-but-2-en-1-yl |
| 1227 | $CH_3$ | 2,3-$Cl_2$—$C_6H_3$ | H |
| 1228 | $CH_3$ | 2,3-$Cl_2$—$C_6H_3$ | $CH_3$ |
| 1229 | $CH_3$ | 2,3-$Cl_2$—$C_6H_3$ | $C_2H_5$ |
| 1230 | $CH_3$ | 2,3-$Cl_2$—$C_6H_3$ | n-$C_3H_7$ |
| 1231 | $CH_3$ | 2,3-$Cl_2$—$C_6H_3$ | i-$C_3H_7$ |
| 1232 | $CH_3$ | 2,3-$Cl_2$—$C_6H_3$ | n-$C_4H_9$ |
| 1233 | $CH_3$ | 2,3-$Cl_2$—$C_6H_3$ | t-$C_4H_9$ |
| 1234 | $CH_3$ | 2,3-$Cl_2$—$C_6H_3$ | n-$C_6H_{13}$ |
| 1235 | $CH_3$ | 2,3-$Cl_2$—$C_6H_3$ | Prop-1-en-3-yl |
| 1236 | $CH_3$ | 2,3-$Cl_2$—$C_6H_3$ | (E)-1-Chloroprop-1-en-3-yl |
| 1237 | $CH_3$ | 2,3-$Cl_2$—$C_6H_3$ | Propyn-3-yl |
| 1238 | $CH_3$ | 2,3-$Cl_2$—$C_6H_3$ | 3-Methyl-but-2-en-1-yl |
| 1239 | $CH_3$ | 2,4-$Cl_2$—$C_6H_3$ | H |
| 1240 | $CH_3$ | 2,4-$Cl_2$—$C_6H_3$ | $CH_3$ |
| 1241 | $CH_3$ | 2,4-$Cl_2$—$C_6H_3$ | $C_2H_5$ |
| 1242 | $CH_3$ | 2,4-$Cl_2$—$C_6H_3$ | n-$C_3H_7$ |
| 1243 | $CH_3$ | 2,4-$Cl_2$—$C_6H_3$ | i-$C_3H_7$ |
| 1244 | $CH_3$ | 2,4-$Cl_2$—$C_6H_3$ | n-$C_4H_9$ |
| 1245 | $CH_3$ | 2,4-$Cl_2$—$C_6H_3$ | t-$C_4H_9$ |
| 1246 | $CH_3$ | 2,4-$Cl_2$—$C_6H_3$ | n-$C_6H_{13}$ |
| 1247 | $CH_3$ | 2,4-$Cl_2$—$C_6H_3$ | Prop-1-en-3-yl |
| 1248 | $CH_3$ | 2,4-$Cl_2$—$C_6H_3$ | (E)-1-Chloroprop-1-en-3-yl |
| 1249 | $CH_3$ | 2,4-$Cl_2$—$C_6H_3$ | Propyn-3-yl |
| 1250 | $CH_3$ | 2,4-$Cl_2$—$C_6H_3$ | 3-Methyl-but-2-en-1-yl |
| 1251 | $CH_3$ | 2,5-$Cl_2$—$C_6H_3$ | H |
| 1252 | $CH_3$ | 2,5-$Cl_2$—$C_6H_3$ | $CH_3$ |
| 1253 | $CH_3$ | 2,5-$Cl_2$—$C_6H_3$ | $C_2H_5$ |
| 1254 | $CH_3$ | 2,5-$Cl_2$—$C_6H_3$ | n-$C_3H_7$ |
| 1255 | $CH_3$ | 2,5-$Cl_2$—$C_6H_3$ | i-$C_3H_7$ |
| 1256 | $CH_3$ | 2,5-$Cl_2$—$C_6H_3$ | n-$C_4H_9$ |
| 1257 | $CH_3$ | 2,5-$Cl_2$—$C_6H_3$ | t-$C_4H_9$ |
| 1258 | $CH_3$ | 2,5-$Cl_2$—$C_6H_3$ | n-$C_6H_{13}$ |
| 1259 | $CH_3$ | 2,5-$Cl_2$—$C_6H_3$ | Prop-1-en-3-yl |
| 1260 | $CH_3$ | 2,5-$Cl_2$—$C_6H_3$ | (E)-1-Chloroprop-1-en-3-yl |
| 1261 | $CH_3$ | 2,5-$Cl_2$—$C_6H_3$ | Propyn-3-yl |
| 1262 | $CH_3$ | 2,5-$Cl_2$—$C_6H_3$ | 3-Methyl-but-2-en-1-yl |
| 1263 | $CH_3$ | 2,6-$Cl_2$—$C_6H_3$ | H |
| 1264 | $CH_3$ | 2,6-$Cl_2$—$C_6H_3$ | $CH_3$ |
| 1265 | $CH_3$ | 2,6-$Cl_2$—$C_6H_3$ | $C_2H_5$ |
| 1266 | $CH_3$ | 2,6-$Cl_2$—$C_6H_3$ | n-$C_3H_7$ |
| 1267 | $CH_3$ | 2,6-$Cl_2$—$C_6H_3$ | i-$C_3H_7$ |
| 1268 | $CH_3$ | 2,6-$Cl_2$—$C_6H_3$ | n-$C_4H_9$ |
| 1269 | $CH_3$ | 2,6-$Cl_2$—$C_6H_3$ | t-$C_4H_9$ |
| 1270 | $CH_3$ | 2,6-$Cl_2$—$C_6H_3$ | n-$C_6H_{13}$ |
| 1271 | $CH_3$ | 2,6-$Cl_2$—$C_6H_3$ | Prop-1-en-3-yl |
| 1272 | $CH_3$ | 2,6-$Cl_2$—$C_6H_3$ | (E)-1-Chloroprop-1-en-3-yl |
| 1273 | $CH_3$ | 2,6-$Cl_2$—$C_6H_3$ | Propyn-3-yl |
| 1274 | $CH_3$ | 2,6-$Cl_2$—$C_6H_3$ | 3-Methyl-but-2-en-1-yl |
| 1275 | $CH_3$ | 3,4-$Cl_2$—$C_6H_3$ | H |
| 1276 | $CH_3$ | 3,4-$Cl_2$—$C_6H_3$ | $CH_3$ |
| 1277 | $CH_3$ | 3,4-$Cl_2$—$C_6H_3$ | $C_2H_5$ |
| 1278 | $CH_3$ | 3,4-$Cl_2$—$C_6H_3$ | n-$C_3H_7$ |
| 1279 | $CH_3$ | 3,4-$Cl_2$—$C_6H_3$ | i-$C_3H_7$ |
| 1280 | $CH_3$ | 3,4-$Cl_2$—$C_6H_3$ | n-$C_4H_9$ |
| 1281 | $CH_3$ | 3,4-$Cl_2$—$C_6H_3$ | t-$C_4H_9$ |
| 1282 | $CH_3$ | 3,4-$Cl_2$—$C_6H_3$ | n-$C_6H_{13}$ |
| 1283 | $CH_3$ | 3,4-$Cl_2$—$C_6H_3$ | Prop-1-en-3-yl |
| 1284 | $CH_3$ | 3,4-$Cl_2$—$C_6H_3$ | (E)-1-Chloroprop-1-en-3-yl |
| 1285 | $CH_3$ | 3,4-$Cl_2$—$C_6H_3$ | Propyn-3-yl |
| 1286 | $CH_3$ | 3,4-$Cl_2$—$C_6H_3$ | 3-Methyl-but-2-en-1-yl |
| 1287 | $CH_3$ | 3,5-$Cl_2$—$C_6H_3$ | H |
| 1288 | $CH_3$ | 3,5-$Cl_2$—$C_6H_3$ | $CH_3$ |
| 1289 | $CH_3$ | 3,5-$Cl_2$—$C_6H_3$ | $C_2H_5$ |
| 1290 | $CH_3$ | 3,5-$Cl_2$—$C_6H_3$ | n-$C_3H_7$ |
| 1291 | $CH_3$ | 3,5-$Cl_2$—$C_6H_3$ | i-$C_3H_7$ |
| 1292 | $CH_3$ | 3,5-$Cl_2$—$C_6H_3$ | n-$C_4H_9$ |
| 1293 | $CH_3$ | 3,5-$Cl_2$—$C_6H_3$ | t-$C_4H_9$ |
| 1294 | $CH_3$ | 3,5-$Cl_2$—$C_6H_3$ | n-$C_6H_{13}$ |
| 1295 | $CH_3$ | 3,5-$Cl_2$—$C_6H_3$ | Prop-1-en-3-yl |
| 1296 | $CH_3$ | 3,5-$Cl_2$—$C_6H_3$ | (E)-1-Chloroprop-1-en-3-yl |
| 1297 | $CH_3$ | 3,5-$Cl_2$—$C_6H_3$ | Propyn-3-yl |
| 1298 | $CH_3$ | 3,5-$Cl_2$—$C_6H_3$ | 3-Methyl-but-2-en-1-yl |
| 1299 | $CH_3$ | 2-Br—$C_6H_4$ | H |
| 1300 | $CH_3$ | 2-Br—$C_6H_4$ | $CH_3$ |
| 1301 | $CH_3$ | 2-Br—$C_6H_4$ | $C_2H_5$ |
| 1302 | $CH_3$ | 2-Br—$C_6H_4$ | n-$C_3H_7$ |
| 1303 | $CH_3$ | 2-Br—$C_6H_4$ | i-$C_3H_7$ |
| 1304 | $CH_3$ | 2-Br—$C_6H_4$ | n-$C_4H_9$ |
| 1305 | $CH_3$ | 2-Br—$C_6H_4$ | t-$C_4H_9$ |
| 1306 | $CH_3$ | 2-Br—$C_6H_4$ | n-$C_6H_{13}$ |
| 1307 | $CH_3$ | 2-Br—$C_6H_4$ | Prop-1-en-3-yl |
| 1308 | $CH_3$ | 2-Br—$C_6H_4$ | (E)-1-Chloroprop-1-en-3-yl |
| 1309 | $CH_3$ | 2-Br—$C_6H_4$ | Propyn-3-yl |
| 1310 | $CH_3$ | 2-Br—$C_6H_4$ | 3-Methyl-but-2-en-1-yl |
| 1311 | $CH_3$ | 3-Br—$C_6H_4$ | H |
| 1312 | $CH_3$ | 3-Br—$C_6H_4$ | $CH_3$ |
| 1313 | $CH_3$ | 3-Br—$C_6H_4$ | $C_2H_5$ |
| 1314 | $CH_3$ | 3-Br—$C_6H_4$ | n-$C_3H_7$ |
| 1315 | $CH_3$ | 3-Br—$C_6H_4$ | i-$C_3H_7$ |
| 1316 | $CH_3$ | 3-Br—$C_6H_4$ | n-$C_4H_9$ |
| 1317 | $CH_3$ | 3-Br—$C_6H_4$ | t-$C_4H_9$ |
| 1318 | $CH_3$ | 3-Br—$C_6H_4$ | n-$C_6H_{13}$ |
| 1319 | $CH_3$ | 3-Br—$C_6H_4$ | Prop-1-en-3-yl |
| 1320 | $CH_3$ | 3-Br—$C_6H_4$ | (E)-1-Chloroprop-1-en-3-yl |

TABLE A-continued

| No. | $R^3$ | $R^4$ | $R^5$ |
|---|---|---|---|
| 1321 | $CH_3$ | 3-Br—$C_6H_4$ | Propyn-3-yl |
| 1322 | $CH_3$ | 3-Br—$C_6H_4$ | 3-Methyl-but-2-en-1-yl |
| 1323 | $CH_3$ | 4-Br—$C_6H_4$ | H |
| 1324 | $CH_3$ | 4-Br—$C_6H_4$ | $CH_3$ |
| 1325 | $CH_3$ | 4-Br—$C_6H_4$ | $C_2H_5$ |
| 1326 | $CH_3$ | 4-Br—$C_6H_4$ | n-$C_3H_7$ |
| 1327 | $CH_3$ | 4-Br—$C_6H_4$ | i-$C_3H_7$ |
| 1328 | $CH_3$ | 4-Br—$C_6H_4$ | n-$C_4H_9$ |
| 1329 | $CH_3$ | 4-Br—$C_6H_4$ | t-$C_4H_9$ |
| 1330 | $CH_3$ | 4-Br—$C_6H_4$ | n-$C_6H_{13}$ |
| 1331 | $CH_3$ | 4-Br—$C_6H_4$ | Prop-1-en-3-yl |
| 1332 | $CH_3$ | 4-Br—$C_6H_4$ | (E)-1-Chloroprop-1-en-3-yl |
| 1333 | $CH_3$ | 4-Br—$C_6H_4$ | Propyn-3-yl |
| 1334 | $CH_3$ | 4-Br—$C_6H_4$ | 3-Methyl-but-2-en-1-yl |
| 1335 | $CH_3$ | 2-I—$C_6H_4$ | H |
| 1336 | $CH_3$ | 2-I—$C_6H_4$ | $CH_3$ |
| 1337 | $CH_3$ | 2-I—$C_6H_4$ | $C_2H_5$ |
| 1338 | $CH_3$ | 2-I—$C_6H_4$ | n-$C_3H_7$ |
| 1339 | $CH_3$ | 2-I—$C_6H_4$ | i-$C_3H_7$ |
| 1340 | $CH_3$ | 2-I—$C_6H_4$ | n-$C_4H_9$ |
| 1341 | $CH_3$ | 2-I—$C_6H_4$ | t-$C_4H_9$ |
| 1342 | $CH_3$ | 2-I—$C_6H_4$ | n-$C_6H_{13}$ |
| 1343 | $CH_3$ | 2-I—$C_6H_4$ | Prop-1-en-3-yl |
| 1344 | $CH_3$ | 2-I—$C_6H_4$ | (E)-1-Chloroprop-1-en-3-yl |
| 1345 | $CH_3$ | 2-I—$C_6H_4$ | Propyn-3-yl |
| 1346 | $CH_3$ | 2-I—$C_6H_4$ | 3-Methyl-but-2-en-1-yl |
| 1347 | $CH_3$ | 3-I—$C_6H_4$ | H |
| 1348 | $CH_3$ | 3-I—$C_6H_4$ | $CH_3$ |
| 1349 | $CH_3$ | 3-I—$C_6H_4$ | $C_2H_5$ |
| 1350 | $CH_3$ | 3-I—$C_6H_4$ | n-$C_3H_7$ |
| 1351 | $CH_3$ | 3-I—$C_6H_4$ | i-$C_3H_7$ |
| 1352 | $CH_3$ | 3-I—$C_6H_4$ | n-$C_4H_9$ |
| 1353 | $CH_3$ | 3-I—$C_6H_4$ | t-$C_4H_9$ |
| 1354 | $CH_3$ | 3-I—$C_6H_4$ | n-$C_6H_{13}$ |
| 1355 | $CH_3$ | 3-I—$C_6H_4$ | Prop-1-en-3-yl |
| 1356 | $CH_3$ | 3-I—$C_6H_4$ | (E)-1-Chloroprop-1-en-3-yl |
| 1357 | $CH_3$ | 3-I—$C_6H_4$ | Propyn-3-yl |
| 1358 | $CH_3$ | 3-I—$C_6H_4$ | 3-Methyl-but-2-en-1-yl |
| 1359 | $CH_3$ | 4-I—$C_6H_4$ | H |
| 1360 | $CH_3$ | 4-I—$C_6H_4$ | $CH_3$ |
| 1361 | $CH_3$ | 4-I—$C_6H_4$ | $C_2H_5$ |
| 1362 | $CH_3$ | 4-I—$C_6H_4$ | n-$C_3H_7$ |
| 1363 | $CH_3$ | 4-I—$C_6H_4$ | i-$C_3H_7$ |
| 1364 | $CH_3$ | 4-I—$C_6H_4$ | n-$C_4H_9$ |
| 1365 | $CH_3$ | 4-I—$C_6H_4$ | t-$C_4H_9$ |
| 1366 | $CH_3$ | 4-I—$C_6H_4$ | n-$C_6H_{13}$ |
| 1367 | $CH_3$ | 4-I—$C_6H_4$ | Prop-1-en-3-yl |
| 1368 | $CH_3$ | 4-I—$C_6H_4$ | (E)-1-Chloroprop-1-en-3-yl |
| 1369 | $CH_3$ | 4-I—$C_6H_4$ | Propyn-3-yl |
| 1370 | $CH_3$ | 4-I—$C_6H_4$ | 3-Methyl-but-2-en-1-yl |
| 1371 | $CH_3$ | 2-CN—$C_6H_4$ | H |
| 1372 | $CH_3$ | 2-CN—$C_6H_4$ | $CH_3$ |
| 1373 | $CH_3$ | 2-CN—$C_6H_4$ | $C_2H_5$ |
| 1374 | $CH_3$ | 2-CN—$C_6H_4$ | n-$C_3H_7$ |
| 1375 | $CH_3$ | 2-CN—$C_6H_4$ | i-$C_3H_7$ |
| 1376 | $CH_3$ | 2-CN—$C_6H_4$ | n-$C_4H_9$ |
| 1377 | $CH_3$ | 2-CN—$C_6H_4$ | t-$C_4H_9$ |
| 1378 | $CH_3$ | 2-CN—$C_6H_4$ | n-$C_6H_{13}$ |
| 1379 | $CH_3$ | 2-CN—$C_6H_4$ | Prop-1-en-3-yl |
| 1380 | $CH_3$ | 2-CN—$C_6H_4$ | (E)-1-Chloroprop-1-en-3-yl |
| 1381 | $CH_3$ | 2-CN—$C_6H_4$ | Propyn-3-yl |
| 1382 | $CH_3$ | 2-CN—$C_6H_4$ | 3-Methyl-but-2-en-1-yl |
| 1383 | $CH_3$ | 3-CN—$C_6H_4$ | H |
| 1384 | $CH_3$ | 3-CN—$C_6H_4$ | $CH_3$ |
| 1385 | $CH_3$ | 3-CN—$C_6H_4$ | $C_2H_5$ |
| 1386 | $CH_3$ | 3-CN—$C_6H_4$ | n-$C_3H_7$ |
| 1387 | $CH_3$ | 3-CN—$C_6H_4$ | i-$C_3H_7$ |
| 1388 | $CH_3$ | 3-CN—$C_6H_4$ | n-$C_4H_9$ |
| 1389 | $CH_3$ | 3-CN—$C_6H_4$ | t-$C_4H_9$ |
| 1390 | $CH_3$ | 3-CN—$C_6H_4$ | n-$C_6H_{13}$ |
| 1391 | $CH_3$ | 3-CN—$C_6H_4$ | Prop-1-en-3-yl |
| 1392 | $CH_3$ | 3-CN—$C_6H_4$ | (E)-1-Chloroprop-1-en-3-yl |
| 1393 | $CH_3$ | 3-CN—$C_6H_4$ | Propyn-3-yl |
| 1394 | $CH_3$ | 3-CN—$C_6H_4$ | 3-Methyl-but-2-en-1-yl |
| 1395 | $CH_3$ | 4-CN—$C_6H_4$ | H |
| 1396 | $CH_3$ | 4-CN—$C_6H_4$ | $CH_3$ |
| 1397 | $CH_3$ | 4-CN—$C_6H_4$ | $C_2H_5$ |

TABLE A-continued

| No. | $R^3$ | $R^4$ | $R^5$ |
|---|---|---|---|
| 1398 | $CH_3$ | 4-CN—$C_6H_4$ | n-$C_3H_7$ |
| 1399 | $CH_3$ | 4-CN—$C_6H_4$ | i-$C_3H_7$ |
| 1400 | $CH_3$ | 4-CN—$C_6H_4$ | n-$C_4H_9$ |
| 1401 | $CH_3$ | 4-CN—$C_6H_4$ | t-$C_4H_9$ |
| 1402 | $CH_3$ | 4-CN—$C_6H_4$ | n-$C_6H_{13}$ |
| 1403 | $CH_3$ | 4-CN—$C_6H_4$ | Prop-1-en-3-yl |
| 1404 | $CH_3$ | 4-CN—$C_6H_4$ | (E)-1-Chloroprop-1-en-3-yl |
| 1405 | $CH_3$ | 4-CN—$C_6H_4$ | Propyn-3-yl |
| 1406 | $CH_3$ | 4-CN—$C_6H_4$ | 3-Methyl-but-2-en-1-yl |
| 1407 | $CH_3$ | 2-$NO_2$—$C_6H_4$ | H |
| 1408 | $CH_3$ | 2-$NO_2$—$C_6H_4$ | $CH_3$ |
| 1409 | $CH_3$ | 2-$NO_2$—$C_6H_4$ | $C_2H_5$ |
| 1410 | $CH_3$ | 2-$NO_2$—$C_6H_4$ | n-$C_3H_7$ |
| 1411 | $CH_3$ | 2-$NO_2$—$C_6H_4$ | i-$C_3H_7$ |
| 1412 | $CH_3$ | 2-$NO_2$—$C_6H_4$ | n-$C_4H_9$ |
| 1413 | $CH_3$ | 2-$NO_2$—$C_6H_4$ | t-$C_4H_9$ |
| 1414 | $CH_3$ | 2-$NO_2$—$C_6H_4$ | n-$C_6H_{13}$ |
| 1415 | $CH_3$ | 2-$NO_2$—$C_6H_4$ | Prop-1-en-3-yl |
| 1416 | $CH_3$ | 2-$NO_2$—$C_6H_4$ | (E)-1-Chloroprop-1-en-3-yl |
| 1417 | $CH_3$ | 2-$NO_2$—$C_6H_4$ | Propyn-3-yl |
| 1418 | $CH_3$ | 2-$NO_2$—$C_6H_4$ | 3-Methyl-but-2-en-1-yl |
| 1419 | $CH_3$ | 3-$NO_2$—$C_6H_4$ | H |
| 1420 | $CH_3$ | 3-$NO_2$—$C_6H_4$ | $CH_3$ |
| 1421 | $CH_3$ | 3-$NO_2$—$C_6H_4$ | $C_2H_5$ |
| 1422 | $CH_3$ | 3-$NO_2$—$C_6H_4$ | n-$C_3H_7$ |
| 1423 | $CH_3$ | 3-$NO_2$—$C_6H_4$ | i-$C_3H_7$ |
| 1424 | $CH_3$ | 3-$NO_2$—$C_6H_4$ | n-$C_4H_9$ |
| 1425 | $CH_3$ | 3-$NO_2$—$C_6H_4$ | t-$C_4H_9$ |
| 1426 | $CH_3$ | 3-$NO_2$—$C_6H_4$ | n-$C_6H_{13}$ |
| 1427 | $CH_3$ | 3-$NO_2$—$C_6H_4$ | Prop-1-en-3-yl |
| 1428 | $CH_3$ | 3-$NO_2$—$C_6H_4$ | (E)-1-Chloroprop-1-en-3-yl |
| 1429 | $CH_3$ | 3-$NO_2$—$C_6H_4$ | Propyn-3-yl |
| 1430 | $CH_3$ | 3-$NO_2$—$C_6H_4$ | 3-Methyl-but-2-en-1-yl |
| 1431 | $CH_3$ | 4-$NO_2$—$C_6H_4$ | H |
| 1432 | $CH_3$ | 4-$NO_2$—$C_6H_4$ | $CH_3$ |
| 1433 | $CH_3$ | 4-$NO_2$—$C_6H_4$ | $C_2H_5$ |
| 1434 | $CH_3$ | 4-$NO_2$—$C_6H_4$ | n-$C_3H_7$ |
| 1435 | $CH_3$ | 4-$NO_2$—$C_6H_4$ | i-$C_3H_7$ |
| 1436 | $CH_3$ | 4-$NO_2$—$C_6H_4$ | n-$C_4H_9$ |
| 1437 | $CH_3$ | 4-$NO_2$—$C_6H_4$ | t-$C_4H_9$ |
| 1438 | $CH_3$ | 4-$NO_2$—$C_6H_4$ | n-$C_6H_{13}$ |
| 1439 | $CH_3$ | 4-$NO_2$—$C_6H_4$ | Prop-1-en-3-yl |
| 1440 | $CH_3$ | 4-$NO_2$—$C_6H_4$ | (E)-1-Chloroprop-1-en-3-yl |
| 1441 | $CH_3$ | 4-$NO_2$—$C_6H_4$ | Propyn-3-yl |
| 1442 | $CH_3$ | 4-$NO_2$—$C_6H_4$ | 3-Methyl-but-2-en-1-yl |
| 1443 | $CH_3$ | 2-$CH_3$—$C_6H_4$ | H |
| 1444 | $CH_3$ | 2-$CH_3$—$C_6H_4$ | $CH_3$ |
| 1445 | $CH_3$ | 2-$CH_3$—$C_6H_4$ | $C_2H_5$ |
| 1446 | $CH_3$ | 2-$CH_3$—$C_6H_4$ | n-$C_3H_7$ |
| 1447 | $CH_3$ | 2-$CH_3$—$C_6H_4$ | i-$C_3H_7$ |
| 1448 | $CH_3$ | 2-$CH_3$—$C_6H_4$ | n-$C_4H_9$ |
| 1449 | $CH_3$ | 2-$CH_3$—$C_6H_4$ | t-$C_4H_9$ |
| 1450 | $CH_3$ | 2-$CH_3$—$C_6H_4$ | n-$C_6H_{13}$ |
| 1451 | $CH_3$ | 2-$CH_3$—$C_6H_4$ | Prop-1-en-3-yl |
| 1452 | $CH_3$ | 2-$CH_3$—$C_6H_4$ | (E)-1-Chloroprop-1-en-3-yl |
| 1453 | $CH_3$ | 2-$CH_3$—$C_6H_4$ | Propyn-3-yl |
| 1454 | $CH_3$ | 2-$CH_3$—$C_6H_4$ | 3-Methyl-but-2-en-1-yl |
| 1455 | $CH_3$ | 3-$CH_3$—$C_6H_4$ | H |
| 1456 | $CH_3$ | 3-$CH_3$—$C_6H_4$ | $CH_3$ |
| 1457 | $CH_3$ | 3-$CH_3$—$C_6H_4$ | $C_2H_5$ |
| 1458 | $CH_3$ | 3-$CH_3$—$C_6H_4$ | n-$C_3H_7$ |
| 1459 | $CH_3$ | 3-$CH_3$—$C_6H_4$ | i-$C_3H_7$ |
| 1460 | $CH_3$ | 3-$CH_3$—$C_6H_4$ | n-$C_4H_9$ |
| 1461 | $CH_3$ | 3-$CH_3$—$C_6H_4$ | t-$C_4H_9$ |
| 1462 | $CH_3$ | 3-$CH_3$—$C_6H_4$ | n-$C_6H_{13}$ |
| 1463 | $CH_3$ | 3-$CH_3$—$C_6H_4$ | Prop-1-en-3-yl |
| 1464 | $CH_3$ | 3-$CH_3$—$C_6H_4$ | (E)-1-Chloroprop-1-en-3-yl |
| 1465 | $CH_3$ | 3-$CH_3$—$C_6H_4$ | Propyn-3-yl |
| 1466 | $CH_3$ | 3-$CH_3$—$C_6H_4$ | 3-Methyl-but-2-en-1-yl |
| 1467 | $CH_3$ | 4-$CH_3$—$C_6H_4$ | H |
| 1468 | $CH_3$ | 4-$CH_3$—$C_6H_4$ | $CH_3$ |
| 1469 | $CH_3$ | 4-$CH_3$—$C_6H_4$ | $C_2H_5$ |
| 1470 | $CH_3$ | 4-$CH_3$—$C_6H_4$ | n-$C_3H_7$ |
| 1471 | $CH_3$ | 4-$CH_3$—$C_6H_4$ | i-$C_3H_7$ |
| 1472 | $CH_3$ | 4-$CH_3$—$C_6H_4$ | n-$C_4H_9$ |
| 1473 | $CH_3$ | 4-$CH_3$—$C_6H_4$ | t-$C_4H_9$ |
| 1474 | $CH_3$ | 4-$CH_3$—$C_6H_4$ | n-$C_6H_{13}$ |

TABLE A-continued

| No. | $R^3$ | $R^4$ | $R^5$ |
|---|---|---|---|
| 1475 | $CH_3$ | 4-$CH_3$—$C_6H_4$ | Prop-1-en-3-yl |
| 1476 | $CH_3$ | 4-$CH_3$—$C_6H_4$ | (E)-1-Chloroprop-1-en-3-yl |
| 1477 | $CH_3$ | 4-$CH_3$—$C_6H_4$ | Propyn-3-yl |
| 1478 | $CH_3$ | 4-$CH_3$—$C_6H_4$ | 3-Methyl-but-2-en-1-yl |
| 1479 | $CH_3$ | 2,3-$(CH_3)_2$—$C_6H_3$ | H |
| 1480 | $CH_3$ | 2,3-$(CH_3)_2$—$C_6H_3$ | $CH_3$ |
| 1481 | $CH_3$ | 2,3-$(CH_3)_2$—$C_6H_3$ | $C_2H_5$ |
| 1482 | $CH_3$ | 2,3-$(CH_3)_2$—$C_6H_3$ | n-$C_3H_7$ |
| 1483 | $CH_3$ | 2,3-$(CH_3)_2$—$C_6H_3$ | i-$C_3H_7$ |
| 1484 | $CH_3$ | 2,3-$(CH_3)_2$—$C_6H_3$ | n-$C_4H_9$ |
| 1485 | $CH_3$ | 2,3-$(CH_3)_2$—$C_6H_3$ | t-$C_4H_9$ |
| 1486 | $CH_3$ | 2,3-$(CH_3)_2$—$C_6H_3$ | n-$C_6H_{13}$ |
| 1487 | $CH_3$ | 2,3-$(CH_3)_2$—$C_6H_3$ | Prop-1-en-3-yl |
| 1488 | $CH_3$ | 2,3-$(CH_3)_2$—$C_6H_3$ | (E)-1-Chloroprop-1-en-3-yl |
| 1489 | $CH_3$ | 2,3-$(CH_3)_2$—$C_6H_3$ | Propyn-3-yl |
| 1490 | $CH_3$ | 2,3-$(CH_3)_2$—$C_6H_3$ | 3-Methyl-but-2-en-1-yl |
| 1491 | $CH_3$ | 2,4-$(CH_3)_2$—$C_6H_3$ | H |
| 1492 | $CH_3$ | 2,4-$(CH_3)_2$—$C_6H_3$ | $CH_3$ |
| 1493 | $CH_3$ | 2,4-$(CH_3)_2$—$C_6H_3$ | $C_2H_5$ |
| 1494 | $CH_3$ | 2,4-$(CH_3)_2$—$C_6H_3$ | n-$C_3H_7$ |
| 1495 | $CH_3$ | 2,4-$(CH_3)_2$—$C_6H_3$ | i-$C_3H_7$ |
| 1496 | $CH_3$ | 2,4-$(CH_3)_2$—$C_6H_3$ | n-$C_4H_9$ |
| 1497 | $CH_3$ | 2,4-$(CH_3)_2$—$C_6H_3$ | t-$C_4H_9$ |
| 1498 | $CH_3$ | 2,4-$(CH_3)_2$—$C_6H_3$ | n-$C_6H_{13}$ |
| 1499 | $CH_3$ | 2,4-$(CH_3)_2$—$C_6H_3$ | Prop-1-en-3-yl |
| 1500 | $CH_3$ | 2,4-$(CH_3)_2$—$C_6H_3$ | (E)-1-Chloroprop-1-en-3-yl |
| 1501 | $CH_3$ | 2,4-$(CH_3)_2$—$C_6H_3$ | Propyn-3-yl |
| 1502 | $CH_3$ | 2,4-$(CH_3)_2$—$C_6H_3$ | 3-Methyl-but-2-en-1-yl |
| 1503 | $CH_3$ | 2,5-$(CH_3)_2$—$C_6H_3$ | H |
| 1504 | $CH_3$ | 2,5-$(CH_3)_2$—$C_6H_3$ | $CH_3$ |
| 1505 | $CH_3$ | 2,5-$(CH_3)_2$—$C_6H_3$ | $C_2H_5$ |
| 1506 | $CH_3$ | 2,5-$(CH_3)_2$—$C_6H_3$ | n-$C_3H_7$ |
| 1507 | $CH_3$ | 2,5-$(CH_3)_2$—$C_6H_3$ | i-$C_3H_7$ |
| 1508 | $CH_3$ | 2,5-$(CH_3)_2$—$C_6H_3$ | n-$C_4H_9$ |
| 1509 | $CH_3$ | 2,5-$(CH_3)_2$—$C_6H_3$ | t-$C_4H_9$ |
| 1510 | $CH_3$ | 2,5-$(CH_3)_2$—$C_6H_3$ | n-$C_6H_{13}$ |
| 1511 | $CH_3$ | 2,5-$(CH_3)_2$—$C_6H_3$ | Prop-1-en-3-yl |
| 1512 | $CH_3$ | 2,5-$(CH_3)_2$—$C_6H_3$ | (E)-1-Chloroprop-1-en-3-yl |
| 1513 | $CH_3$ | 2,5-$(CH_3)_2$—$C_6H_3$ | Propyn-3-yl |
| 1514 | $CH_3$ | 2,5-$(CH_3)_2$—$C_6H_3$ | 3-Methyl-but-2-en-1-yl |
| 1515 | $CH_3$ | 2,6-$(CH_3)_2$—$C_6H_3$ | H |
| 1516 | $CH_3$ | 2,6-$(CH_3)_2$—$C_6H_3$ | $CH_3$ |
| 1517 | $CH_3$ | 2,6-$(CH_3)_2$—$C_6H_3$ | $C_2H_5$ |
| 1518 | $CH_3$ | 2,6-$(CH_3)_2$—$C_6H_3$ | n-$C_3H_7$ |
| 1519 | $CH_3$ | 2,6-$(CH_3)_2$—$C_6H_3$ | i-$C_3H_7$ |
| 1520 | $CH_3$ | 2,6-$(CH_3)_2$—$C_6H_3$ | n-$C_4H_9$ |
| 1521 | $CH_3$ | 2,6-$(CH_3)_2$—$C_6H_3$ | t-$C_4H_9$ |
| 1522 | $CH_3$ | 2,6-$(CH_3)_2$—$C_6H_3$ | n-$C_6H_{13}$ |
| 1523 | $CH_3$ | 2,6-$(CH_3)_2$—$C_6H_3$ | Prop-1-en-3-yl |
| 1524 | $CH_3$ | 2,6-$(CH_3)_2$—$C_6H_3$ | (E)-1-Chloroprop-1-en-3-yl |
| 1525 | $CH_3$ | 2,6-$(CH_3)_2$—$C_6H_3$ | Propyn-3-yl |
| 1526 | $CH_3$ | 2,6-$(CH_3)_2$—$C_6H_3$ | 3-Methyl-but-2-en-1-yl |
| 1527 | $CH_3$ | 3,4-$(CH_3)_2$—$C_6H_3$ | H |
| 1528 | $CH_3$ | 3,4-$(CH_3)_2$—$C_6H_3$ | $CH_3$ |
| 1529 | $CH_3$ | 3,4-$(CH_3)_2$—$C_6H_3$ | $C_2H_5$ |
| 1530 | $CH_3$ | 3,4-$(CH_3)_2$—$C_6H_3$ | n-$C_3H_7$ |
| 1531 | $CH_3$ | 3,4-$(CH_3)_2$—$C_6H_3$ | i-$C_3H_7$ |
| 1532 | $CH_3$ | 3,4-$(CH_3)_2$—$C_6H_3$ | n-$C_4H_9$ |
| 1533 | $CH_3$ | 3,4-$(CH_3)_2$—$C_6H_3$ | t-$C_4H_9$ |
| 1534 | $CH_3$ | 3,4-$(CH_3)_2$—$C_6H_3$ | n-$C_6H_{13}$ |
| 1535 | $CH_3$ | 3,4-$(CH_3)_2$—$C_6H_3$ | Prop-1-en-3-yl |
| 1536 | $CH_3$ | 3,4-$(CH_3)_2$—$C_6H_3$ | (E)-1-Chloroprop-1-en-3-yl |
| 1537 | $CH_3$ | 3,4-$(CH_3)_2$—$C_6H_3$ | Propyn-3-yl |
| 1538 | $CH_3$ | 3,4-$(CH_3)_2$—$C_6H_3$ | 3-Methyl-but-2-en-1-yl |
| 1539 | $CH_3$ | 3,5-$(CH_3)_2$—$C_6H_3$ | H |
| 1540 | $CH_3$ | 3,5-$(CH_3)_2$—$C_6H_3$ | $CH_3$ |
| 1541 | $CH_3$ | 3,5-$(CH_3)_2$—$C_6H_3$ | $C_2H_5$ |
| 1542 | $CH_3$ | 3,5-$(CH_3)_2$—$C_6H_3$ | n-$C_3H_7$ |
| 1543 | $CH_3$ | 3,5-$(CH_3)_2$—$C_6H_3$ | i-$C_3H_7$ |
| 1544 | $CH_3$ | 3,5-$(CH_3)_2$—$C_6H_3$ | n-$C_4H_9$ |
| 1545 | $CH_3$ | 3,5-$(CH_3)_2$—$C_6H_3$ | t-$C_4H_9$ |
| 1546 | $CH_3$ | 3,5-$(CH_3)_2$—$C_6H_3$ | n-$C_6H_{13}$ |
| 1547 | $CH_3$ | 3,5-$(CH_3)_2$—$C_6H_3$ | Prop-1-en-3-yl |
| 1548 | $CH_3$ | 3,5-$(CH_3)_2$—$C_6H_3$ | (E)-1-Chloroprop-1-en-3-yl |
| 1549 | $CH_3$ | 3,5-$(CH_3)_2$—$C_6H_3$ | Propyn-3-yl |
| 1550 | $CH_3$ | 3,5-$(CH_3)_2$—$C_6H_3$ | 3-Methyl-but-2-en-1-yl |
| 1551 | $CH_3$ | 2-$C_2H_5$—$C_6H_4$ | H |
| 1552 | $CH_3$ | 2-$C_2H_5$—$C_6H_4$ | $CH_3$ |
| 1553 | $CH_3$ | 2-$C_2H_5$—$C_6H_4$ | $C_2H_5$ |
| 1554 | $CH_3$ | 2-$C_2H_5$—$C_6H_4$ | n-$C_3H_7$ |
| 1555 | $CH_3$ | 2-$C_2H_5$—$C_6H_4$ | t-$C_4H_9$ |
| 1556 | $CH_3$ | 2-$C_2H_5$—$C_6H_4$ | n-$C_6H_{13}$ |
| 1557 | $CH_3$ | 2-$C_2H_5$—$C_6H_4$ | Prop-1-en-3-yl |
| 1558 | $CH_3$ | 2-$C_2H_5$—$C_6H_4$ | (E)-1-Chloroprop-1-en-3-yl |
| 1559 | $CH_3$ | 2-$C_2H_5$—$C_6H_4$ | Propyn-3-yl |
| 1560 | $CH_3$ | 2-$C_2H_5$—$C_6H_4$ | 3-Methyl-but-2-en-1-yl |
| 1561 | $CH_3$ | 3-$C_2H_5$—$C_6H_4$ | H |
| 1562 | $CH_3$ | 3-$C_2H_5$—$C_6H_4$ | $CH_3$ |
| 1563 | $CH_3$ | 3-$C_2H_5$—$C_6H_4$ | $C_2H_5$ |
| 1564 | $CH_3$ | 3-$C_2H_5$—$C_6H_4$ | n-$C_3H_7$ |
| 1565 | $CH_3$ | 3-$C_2H_5$—$C_6H_4$ | i-$C_3H_7$ |
| 1566 | $CH_3$ | 3-$C_2H_5$—$C_6H_4$ | n-$C_4H_9$ |
| 1567 | $CH_3$ | 3-$C_2H_5$—$C_6H_4$ | t-$C_4H_9$ |
| 1568 | $CH_3$ | 3-$C_2H_5$—$C_6H_4$ | n-$C_6H_{13}$ |
| 1569 | $CH_3$ | 3-$C_2H_5$—$C_6H_4$ | Prop-1-en-3-yl |
| 1570 | $CH_3$ | 3-$C_2H_5$—$C_6H_4$ | (E)-1-Chloroprop-1-en-3-yl |
| 1571 | $CH_3$ | 3-$C_2H_5$—$C_6H_4$ | Propyn-3-yl |
| 1572 | $CH_3$ | 3-$C_2H_5$—$C_6H_4$ | 3-Methyl-but-2-en-1-yl |
| 1573 | $CH_3$ | 4-$C_2H_5$—$C_6H_4$ | H |
| 1574 | $CH_3$ | 4-$C_2H_5$—$C_6H_4$ | $CH_3$ |
| 1575 | $CH_3$ | 4-$C_2H_5$—$C_6H_4$ | $C_2H_5$ |
| 1576 | $CH_3$ | 4-$C_2H_5$—$C_6H_4$ | n-$C_3H_7$ |
| 1577 | $CH_3$ | 4-$C_2H_5$—$C_6H_4$ | i-$C_3H_7$ |
| 1578 | $CH_3$ | 4-$C_2H_5$—$C_6H_4$ | n-$C_4H_9$ |
| 1579 | $CH_3$ | 4-$C_2H_5$—$C_6H_4$ | t-$C_4H_9$ |
| 1580 | $CH_3$ | 4-$C_2H_5$—$C_6H_4$ | n-$C_6H_{13}$ |
| 1581 | $CH_3$ | 4-$C_2H_5$—$C_6H_4$ | Prop-1-en-3-yl |
| 1582 | $CH_3$ | 4-$C_2H_5$—$C_6H_4$ | (E)-1-Chloroprop-1-en-3-yl |
| 1583 | $CH_3$ | 4-$C_2H_5$—$C_6H_4$ | Propyn-3-yl |
| 1584 | $CH_3$ | 4-$C_2H_5$—$C_6H_4$ | 3-Methyl-but-2-en-1-yl |
| 1585 | $CH_3$ | 2-i-$C_3H_7$—$C_6H_4$ | H |
| 1586 | $CH_3$ | 2-i-$C_3H_7$—$C_6H_4$ | $CH_3$ |
| 1587 | $CH_3$ | 2-i-$C_3H_7$—$C_6H_4$ | $C_2H_5$ |
| 1588 | $CH_3$ | 2-i-$C_3H_7$—$C_6H_4$ | n-$C_3H_7$ |
| 1589 | $CH_3$ | 2-i-$C_3H_7$—$C_6H_4$ | i-$C_3H_7$ |
| 1590 | $CH_3$ | 2-i-$C_3H_7$—$C_6H_4$ | n-$C_4H_9$ |
| 1591 | $CH_3$ | 2-i-$C_3H_7$—$C_6H_4$ | t-$C_4H_9$ |
| 1592 | $CH_3$ | 2-i-$C_3H_7$—$C_6H_4$ | n-$C_6H_{13}$ |
| 1593 | $CH_3$ | 2-i-$C_3H_7$—$C_6H_4$ | Prop-1-en-3-yl |
| 1594 | $CH_3$ | 2-i-$C_3H_7$—$C_6H_4$ | (E)-1-Chloroprop-1-en-3-yl |
| 1595 | $CH_3$ | 2-i-$C_3H_7$—$C_6H_4$ | Propyn-3-yl |
| 1596 | $CH_3$ | 2-i-$C_3H_7$—$C_6H_4$ | 3-Methyl-but-2-en-1-yl |
| 1597 | $CH_3$ | 3-i-$C_3H_7$—$C_6H_4$ | H |
| 1598 | $CH_3$ | 3-i-$C_3H_7$—$C_6H_4$ | $CH_3$ |
| 1599 | $CH_3$ | 3-i-$C_3H_7$—$C_6H_4$ | $C_2H_5$ |
| 1600 | $CH_3$ | 3-i-$C_3H_7$—$C_6H_4$ | n-$C_3H_7$ |
| 1601 | $CH_3$ | 3-i-$C_3H_7$—$C_6H_4$ | i-$C_3H_7$ |
| 1602 | $CH_3$ | 3-i-$C_3H_7$—$C_6H_4$ | n-$C_4H_9$ |
| 1603 | $CH_3$ | 3-i-$C_3H_7$—$C_6H_4$ | t-$C_4H_9$ |
| 1604 | $CH_3$ | 3-i-$C_3H_7$—$C_6H_4$ | n-$C_6H_{13}$ |
| 1605 | $CH_3$ | 3-i-$C_3H_7$—$C_6H_4$ | Prop-1-en-3-yl |
| 1606 | $CH_3$ | 3-i-$C_3H_7$—$C_6H_4$ | (E)-1-Chloroprop-1-en-3-yl |
| 1607 | $CH_3$ | 3-i-$C_3H_7$—$C_6H_4$ | Propyn-3-yl |
| 1608 | $CH_3$ | 3-i-$C_3H_7$—$C_6H_4$ | 3-Methyl-but-2-en-1-yl |
| 1609 | $CH_3$ | 4-i-$C_3H_7$—$C_6H_4$ | H |
| 1610 | $CH_3$ | 4-i-$C_3H_7$—$C_6H_4$ | $CH_3$ |
| 1611 | $CH_3$ | 4-i-$C_3H_7$—$C_6H_4$ | $C_2H_5$ |
| 1612 | $CH_3$ | 4-i-$C_3H_7$—$C_6H_4$ | n-$C_3H_7$ |
| 1613 | $CH_3$ | 4-i-$C_3H_7$—$C_6H_4$ | i-$C_3H_7$ |
| 1614 | $CH_3$ | 4-i-$C_3H_7$—$C_6H_4$ | n-$C_4H_9$ |
| 1615 | $CH_3$ | 4-i-$C_3H_7$—$C_6H_4$ | t-$C_4H_9$ |
| 1616 | $CH_3$ | 4-i-$C_3H_7$—$C_6H_4$ | n-$C_6H_{13}$ |
| 1617 | $CH_3$ | 4-i-$C_3H_7$—$C_6H_4$ | Prop-1-en-3-yl |
| 1618 | $CH_3$ | 4-i-$C_3H_7$—$C_6H_4$ | (E)-1-Chloroprop-1-en-3-yl |
| 1619 | $CH_3$ | 4-i-$C_3H_7$—$C_6H_4$ | Propyn-3-yl |
| 1620 | $CH_3$ | 4-i-$C_3H_7$—$C_6H_4$ | 3-Methyl-but-2-en-1-yl |
| 1621 | $CH_3$ | 2-OH—$C_6H_4$ | H |
| 1622 | $CH_3$ | 2-OH—$C_6H_4$ | $CH_3$ |
| 1623 | $CH_3$ | 2-OH—$C_6H_4$ | $C_2H_5$ |
| 1624 | $CH_3$ | 2-OH—$C_6H_4$ | n-$C_3H_7$ |
| 1625 | $CH_3$ | 2-OH—$C_6H_4$ | i-$C_3H_7$ |
| 1626 | $CH_3$ | 2-OH—$C_6H_4$ | n-$C_4H_9$ |
| 1627 | $CH_3$ | 2-OH—$C_6H_4$ | t-$C_4H_9$ |
| 1628 | $CH_3$ | 2-OH—$C_6H_4$ | n-$C_6H_{13}$ |

TABLE A-continued

| No. | $R^3$ | $R^4$ | $R^5$ |
|---|---|---|---|
| 1629 | $CH_3$ | 2-OH—$C_6H_4$ | Prop-1-en-3-yl |
| 1630 | $CH_3$ | 2-OH—$C_6H_4$ | (E)-1-Chloroprop-1-en-3-yl |
| 1631 | $CH_3$ | 2-OH—$C_6H_4$ | Propyn-3-yl |
| 1632 | $CH_3$ | 2-OH—$C_6H_4$ | 3-Methyl-but-2-en-1-yl |
| 1633 | $CH_3$ | 3-OH—$C_6H_4$ | H |
| 1634 | $CH_3$ | 3-OH—$C_6H_4$ | $CH_3$ |
| 1635 | $CH_3$ | 3-OH—$C_6H_4$ | $C_2H_5$ |
| 1636 | $CH_3$ | 3-OH—$C_6H_4$ | n-$C_3H_7$ |
| 1637 | $CH_3$ | 3-OH—$C_6H_4$ | i-$C_3H_7$ |
| 1638 | $CH_3$ | 3-OH—$C_6H_4$ | n-$C_4H_9$ |
| 1639 | $CH_3$ | 3-OH—$C_6H_4$ | t-$C_4H_9$ |
| 1640 | $CH_3$ | 3-OH—$C_6H_4$ | n-$C_6H_{13}$ |
| 1641 | $CH_3$ | 3-OH—$C_6H_4$ | Prop-1-en-3-yl |
| 1642 | $CH_3$ | 3-OH—$C_6H_4$ | (E)-1-Chloroprop-1-en-3-yl |
| 1643 | $CH_3$ | 3-OH—$C_6H_4$ | Propyn-3-yl |
| 1644 | $CH_3$ | 3-OH—$C_6H_4$ | 3-Methyl-but-2-en-1-yl |
| 1645 | $CH_3$ | 4-OH—$C_6H_4$ | H |
| 1646 | $CH_3$ | 4-OH—$C_6H_4$ | $CH_3$ |
| 1647 | $CH_3$ | 4-OH—$C_6H_4$ | $C_2H_5$ |
| 1648 | $CH_3$ | 4-OH—$C_6H_4$ | n-$C_3H_7$ |
| 1649 | $CH_3$ | 4-OH—$C_6H_4$ | i-$C_3H_7$ |
| 1650 | $CH_3$ | 4-OH—$C_6H_4$ | n-$C_4H_9$ |
| 1651 | $CH_3$ | 4-OH—$C_6H_4$ | t-$C_4H_9$ |
| 1652 | $CH_3$ | 4-OH—$C_6H_4$ | n-$C_6H_{13}$ |
| 1653 | $CH_3$ | 4-OH—$C_6H_4$ | Prop-1-en-3-yl |
| 1654 | $CH_3$ | 4-OH—$C_6H_4$ | (E)-1-Chloroprop-1-en-3-yl |
| 1655 | $CH_3$ | 4-OH—$C_6H_4$ | Propyn-3-yl |
| 1656 | $CH_3$ | 4-OH—$C_6H_4$ | 3-Methyl-but-2-en-1-yl |
| 1657 | $CH_3$ | 2-$OCH_3$—$C_6H_4$ | H |
| 1658 | $CH_3$ | 2-$OCH_3$—$C_6H_4$ | $CH_3$ |
| 1659 | $CH_3$ | 2-$OCH_3$—$C_6H_4$ | $C_2H_5$ |
| 1660 | $CH_3$ | 2-$OCH_3$—$C_6H_4$ | n-$C_3H_7$ |
| 1661 | $CH_3$ | 2-$OCH_3$—$C_6H_4$ | i-$C_3H_7$ |
| 1662 | $CH_3$ | 2-$OCH_3$—$C_6H_4$ | n-$C_4H_9$ |
| 1663 | $CH_3$ | 2-$OCH_3$—$C_6H_4$ | t-$C_4H_9$ |
| 1664 | $CH_3$ | 2-$OCH_3$—$C_6H_4$ | n-$C_6H_{13}$ |
| 1665 | $CH_3$ | 2-$OCH_3$—$C_6H_4$ | Prop-1-en-3-yl |
| 1666 | $CH_3$ | 2-$OCH_3$—$C_6H_4$ | (E)-1-Chloroprop-1-en-3-yl |
| 1667 | $CH_3$ | 2-$OCH_3$—$C_6H_4$ | Propyn-3-yl |
| 1668 | $CH_3$ | 2-$OCH_3$—$C_6H_4$ | 3-Methyl-but-2-en-1-yl |
| 1669 | $CH_3$ | 3-$OCH_3$—$C_6H_4$ | H |
| 1670 | $CH_3$ | 3-$OCH_3$—$C_6H_4$ | $CH_3$ |
| 1671 | $CH_3$ | 3-$OCH_3$—$C_6H_4$ | $C_2H_5$ |
| 1672 | $CH_3$ | 3-$OCH_3$—$C_6H_4$ | n-$C_3H_7$ |
| 1673 | $CH_3$ | 3-$OCH_3$—$C_6H_4$ | i-$C_3H_7$ |
| 1674 | $CH_3$ | 3-$OCH_3$—$C_6H_4$ | n-$C_4H_9$ |
| 1675 | $CH_3$ | 3-$OCH_3$—$C_6H_4$ | t-$C_4H_9$ |
| 1676 | $CH_3$ | 3-$OCH_3$—$C_6H_4$ | n-$C_6H_{13}$ |
| 1677 | $CH_3$ | 3-$OCH_3$—$C_6H_4$ | Prop-1-en-3-yl |
| 1678 | $CH_3$ | 3-$OCH_3$—$C_6H_4$ | (E)-1-Chloroprop-1-en-3-yl |
| 1679 | $CH_3$ | 3-$OCH_3$—$C_6H_4$ | Propyn-3-yl |
| 1680 | $CH_3$ | 3-$OCH_3$—$C_6H_4$ | 3-Methyl-but-2-en-1-yl |
| 1681 | $CH_3$ | 4-$OCH_3$—$C_6H_4$ | H |
| 1682 | $CH_3$ | 4-$OCH_3$—$C_6H_4$ | $CH_3$ |
| 1683 | $CH_3$ | 4-$OCH_3$—$C_6H_4$ | $C_2H_5$ |
| 1684 | $CH_3$ | 4-$OCH_3$—$C_6H_4$ | n-$C_3H_7$ |
| 1685 | $CH_3$ | 4-$OCH_3$—$C_6H_4$ | i-$C_3H_7$ |
| 1686 | $CH_3$ | 4-$OCH_3$—$C_6H_4$ | n-$C_4H_9$ |
| 1687 | $CH_3$ | 4-$OCH_3$—$C_6H_4$ | t-$C_4H_9$ |
| 1688 | $CH_3$ | 4-$OCH_3$—$C_6H_4$ | n-$C_6H_{13}$ |
| 1689 | $CH_3$ | 4-$OCH_3$—$C_6H_4$ | Prop-1-en-3-yl |
| 1690 | $CH_3$ | 4-$OCH_3$—$C_6H_4$ | (E)-1-Chloroprop-1-en-3-yl |
| 1691 | $CH_3$ | 4-$OCH_3$—$C_6H_4$ | Propyn-3-yl |
| 1692 | $CH_3$ | 4-$OCH_3$—$C_6H_4$ | 3-Methyl-but-2-en-1-yl |
| 1693 | $CH_3$ | 2-$OC_2H_5$—$C_6H_4$ | H |
| 1694 | $CH_3$ | 2-$OC_2H_5$—$C_6H_4$ | $CH_3$ |
| 1695 | $CH_3$ | 2-$OC_2H_5$—$C_6H_4$ | $C_2H_5$ |
| 1696 | $CH_3$ | 2-$OC_2H_5$—$C_6H_4$ | n-$C_3H_7$ |
| 1697 | $CH_3$ | 2-$OC_2H_5$—$C_6H_4$ | i-$C_3H_7$ |
| 1698 | $CH_3$ | 2-$OC_2H_5$—$C_6H_4$ | n-$C_4H_9$ |
| 1699 | $CH_3$ | 2-$OC_2H_5$—$C_6H_4$ | t-$C_4H_9$ |
| 1700 | $CH_3$ | 2-$OC_2H_5$—$C_6H_4$ | n-$C_6H_{13}$ |
| 1701 | $CH_3$ | 2-$OC_2H_5$—$C_6H_4$ | Prop-1-en-3-yl |
| 1702 | $CH_3$ | 2-$OC_2H_5$—$C_6H_4$ | (E)-1-Chloroprop-1-en-3-yl |
| 1703 | $CH_3$ | 2-$OC_2H_5$—$C_6H_4$ | Propyn-3-yl |
| 1704 | $CH_3$ | 2-$OC_2H_5$—$C_6H_4$ | 3-Methyl-but-2-en-1-yl |
| 1705 | $CH_3$ | 3-$OC_2H_5$—$C_6H_4$ | H |

TABLE A-continued

| No. | $R^3$ | $R^4$ | $R^5$ |
|---|---|---|---|
| 1706 | $CH_3$ | 3-$OC_2H_5$—$C_6H_4$ | $CH_3$ |
| 1707 | $CH_3$ | 3-$OC_2H_5$—$C_6H_4$ | $C_2H_5$ |
| 1708 | $CH_3$ | 3-$OC_2H_5$—$C_6H_4$ | n-$C_3H_7$ |
| 1709 | $CH_3$ | 3-$OC_2H_5$—$C_6H_4$ | i-$C_3H_7$ |
| 1710 | $CH_3$ | 3-$OC_2H_5$—$C_6H_4$ | n-$C_4H_9$ |
| 1711 | $CH_3$ | 3-$OC_2H_5$—$C_6H_4$ | t-$C_4H_9$ |
| 1712 | $CH_3$ | 3-$OC_2H_5$—$C_6H_4$ | n-$C_6H_{13}$ |
| 1713 | $CH_3$ | 3-$OC_2H_5$—$C_6H_4$ | Prop-1-en-3-yl |
| 1714 | $CH_3$ | 3-$OC_2H_5$—$C_6H_4$ | (E)-1-Chloroprop-1-en-3-yl |
| 1715 | $CH_3$ | 3-$OC_2H_5$—$C_6H_4$ | Propyn-3-yl |
| 1716 | $CH_3$ | 3-$OC_2H_5$—$C_6H_4$ | 3-Methyl-but-2-en-1-yl |
| 1717 | $CH_3$ | 4-$OC_2H_5$—$C_6H_4$ | H |
| 1718 | $CH_3$ | 4-$OC_2H_5$—$C_6H_4$ | $CH_3$ |
| 1719 | $CH_3$ | 4-$OC_2H_5$—$C_6H_4$ | $C_2H_5$ |
| 1720 | $CH_3$ | 4-$OC_2H_5$—$C_6H_4$ | n-$C_3H_7$ |
| 1721 | $CH_3$ | 4-$OC_2H_5$—$C_6H_4$ | i-$C_3H_7$ |
| 1722 | $CH_3$ | 4-$OC_2H_5$—$C_6H_4$ | n-$C_4H_9$ |
| 1723 | $CH_3$ | 4-$OC_2H_5$—$C_6H_4$ | t-$C_4H_9$ |
| 1724 | $CH_3$ | 4-$OC_2H_5$—$C_6H_4$ | n-$C_6H_{13}$ |
| 1725 | $CH_3$ | 4-$OC_2H_5$—$C_6H_4$ | Prop-1-en-3-yl |
| 1726 | $CH_3$ | 4-$OC_2H_5$—$C_6H_4$ | (E)-1-Chloroprop-1-en-3-yl |
| 1727 | $CH_3$ | 4-$OC_2H_5$—$C_6H_4$ | Propyn-3-yl |
| 1728 | $CH_3$ | 4-$OC_2H_5$—$C_6H_4$ | 3-Methyl-but-2-en-1-yl |
| 1729 | $CH_3$ | 2-O-(i-$C_3H_7$)—$C_6H_4$ | H |
| 1730 | $CH_3$ | 2-O-(i-$C_3H_7$)—$C_6H_4$ | $CH_3$ |
| 1731 | $CH_3$ | 2-O-(i-$C_3H_7$)—$C_6H_4$ | $C_2H_5$ |
| 1732 | $CH_3$ | 2-O-(i-$C_3H_7$)—$C_6H_4$ | n-$C_3H_7$ |
| 1733 | $CH_3$ | 2-O-(i-$C_3H_7$)—$C_6H_4$ | i-$C_3H_7$ |
| 1734 | $CH_3$ | 2-O-(i-$C_3H_7$)—$C_6H_4$ | n-$C_4H_9$ |
| 1735 | $CH_3$ | 2-O-(i-$C_3H_7$)—$C_6H_4$ | t-$C_4H_9$ |
| 1736 | $CH_3$ | 2-O-(i-$C_3H_7$)—$C_6H_4$ | n-$C_6H_{13}$ |
| 1737 | $CH_3$ | 2-O-(i-$C_3H_7$)—$C_6H_4$ | Prop-1-en-3-yl |
| 1738 | $CH_3$ | 2-O-(i-$C_3H_7$)—$C_6H_4$ | (E)-1-Chloroprop-1-en-3-yl |
| 1739 | $CH_3$ | 2-O-(i-$C_3H_7$)—$C_6H_4$ | Propyn-3-yl |
| 1740 | $CH_3$ | 2-O-(i-$C_3H_7$)—$C_6H_4$ | 3-Methyl-but-2-en-1-yl |
| 1741 | $CH_3$ | 3-O-(i-$C_3H_7$)—$C_6H_4$ | H |
| 1742 | $CH_3$ | 3-O-(i-$C_3H_7$)—$C_6H_4$ | $CH_3$ |
| 1743 | $CH_3$ | 3-O-(i-$C_3H_7$)—$C_6H_4$ | $C_2H_5$ |
| 1744 | $CH_3$ | 3-O-(i-$C_3H_7$)—$C_6H_4$ | n-$C_3H_7$ |
| 1745 | $CH_3$ | 3-O-(i-$C_3H_7$)—$C_6H_4$ | i-$C_3H_7$ |
| 1746 | $CH_3$ | 3-O-(i-$C_3H_7$)—$C_6H_4$ | n-$C_4H_9$ |
| 1747 | $CH_3$ | 3-O-(i-$C_3H_7$)—$C_6H_4$ | t-$C_4H_9$ |
| 1748 | $CH_3$ | 3-O-(i-$C_3H_7$)—$C_6H_4$ | n-$C_6H_{13}$ |
| 1749 | $CH_3$ | 3-O-(i-$C_3H_7$)—$C_6H_4$ | Prop-1-en-3-yX |
| 1750 | $CH_3$ | 3-O-(i-$C_3H_7$)—$C_6H_4$ | (E)-1-Chloroprop-1-en-3-yl |
| 1751 | $CH_3$ | 3-O-(i-$C_3H_7$)—$C_6H_4$ | Propyn-3-yl |
| 1752 | $CH_3$ | 3-O-(i-$C_3H_7$)—$C_6H_4$ | 3-Methyl-but-2-en-1-yl |
| 1753 | $CH_3$ | 4-O-(i-$C_3H_7$)—$C_6H_4$ | H |
| 1754 | $CH_3$ | 4-O-(i-$C_3H_7$)—$C_6H_4$ | $CH_3$ |
| 1755 | $CH_3$ | 4-O-(i-$C_3H_7$)—$C_6H_4$ | $C_2H_5$ |
| 1756 | $CH_3$ | 4-O-(i-$C_3H_7$)—$C_6H_4$ | n-$C_3H_7$ |
| 1757 | $CH_3$ | 4-O-(i-$C_3H_7$)—$C_6H_4$ | i-$C_3H_7$ |
| 1758 | $CH_3$ | 4-O-(i-$C_3H_7$)—$C_6H_4$ | n-$C_4H_9$ |
| 1759 | $CH_3$ | 4-O-(i-$C_3H_7$)—$C_6H_4$ | t-$C_4H_9$ |
| 1760 | $CH_3$ | 4-O-(i-$C_3H_7$)—$C_6H_4$ | n-$C_6H_{13}$ |
| 1761 | $CH_3$ | 4-O-(i-$C_3H_7$)—$C_6H_4$ | Prop-1-en-3-yl |
| 1762 | $CH_3$ | 4-O-(i-$C_3H_7$)—$C_6H_4$ | (E)-1-Chloroprop-1-en-3-yl |
| 1763 | $CH_3$ | 4-O-(i-$C_3H_7$)—$C_6H_4$ | Propyn-3-yl |
| 1764 | $CH_3$ | 4-O-(i-$C_3H_7$)—$C_6H_4$ | 3-Methyl-but-2-en-1-yl |
| 1765 | $CH_3$ | 2-O-(t-$C_4H_9$)—$C_6H_4$ | H |
| 1766 | $CH_3$ | 2-O-(t-$C_4H_9$)—$C_6H_4$ | $CH_3$ |
| 1767 | $CH_3$ | 2-O-(t-$C_4H_9$)—$C_6H_4$ | $C_2H_5$ |
| 1768 | $CH_3$ | 2-O-(t-$C_4H_9$)—$C_6H_4$ | n-$C_3H_7$ |
| 1769 | $CH_3$ | 2-O-(t-$C_4H_9$)—$C_6H_4$ | i-$C_3H_7$ |
| 1770 | $CH_3$ | 2-O-(t-$C_4H_9$)—$C_6H_4$ | n-$C_4H_9$ |
| 1771 | $CH_3$ | 2-O-(t-$C_4H_9$)—$C_6H_4$ | t-$C_4H_9$ |
| 1772 | $CH_3$ | 2-O-(t-$C_4H_9$)—$C_6H_4$ | n-$C_6H_{13}$ |
| 1773 | $CH_3$ | 2-O-(t-$C_4H_9$)—$C_6H_4$ | Prop-1-en-3-yl |
| 1774 | $CH_3$ | 2-O-(t-$C_4H_9$)—$C_6H_4$ | (E)-1-Chloroprop-1-en-3-yl |
| 1775 | $CH_3$ | 2-O-(t-$C_4H_9$)—$C_6H_4$ | Propyn-3-yl |
| 1776 | $CH_3$ | 2-O-(t-$C_4H_9$)—$C_6H_4$ | 3-Methyl-but-2-en-1-yl |
| 1777 | $CH_3$ | 3-O-(t-$C_4H_9$)—$C_6H_4$ | H |
| 1778 | $CH_3$ | 3-O-(t-$C_4H_9$)—$C_6H_4$ | $CH_3$ |
| 1779 | $CH_3$ | 3-O-(t-$C_4H_9$)—$C_6H_4$ | $C_2H_5$ |
| 1780 | $CH_3$ | 3-O-(t-$C_4H_9$)—$C_6H_4$ | n-$C_3H_7$ |
| 1781 | $CH_3$ | 3-O-(t-$C_4H_9$)—$C_6H_4$ | i-$C_3H_7$ |
| 1782 | $CH_3$ | 3-O-(t-$C_4H_9$)—$C_6H_4$ | n-$C_4H_9$ |

TABLE A-continued

| No. | $R^3$ | $R^4$ | $R^5$ |
|---|---|---|---|
| 1783 | $CH_3$ | 3-O-(t-$C_4H_9$)—$C_6H_4$ | t-$C_4H_9$ |
| 1784 | $CH_3$ | 3-O-(t-$C_4H_9$)—$C_6H_4$ | n-$C_6H_{13}$ |
| 1785 | $CH_3$ | 3-O-(t-$C_4H_9$)—$C_6H_4$ | Prop-1-en-3-yl |
| 1786 | $CH_3$ | 3-O-(t-$C_4H_9$)—$C_6H_4$ | (E)-1-Chloroprop-1-en-3-yl |
| 1787 | $CH_3$ | 3-O-(t-$C_4H_9$)—$C_6H_4$ | Propyn-3-yl |
| 1788 | $CH_3$ | 3-O-(t-$C_4H_9$)—$C_6H_4$ | 3-Methyl-but-2-en-1-yl |
| 1789 | $CH_3$ | 4-O-(t-$C_4H_9$)—$C_6H_4$ | H |
| 1790 | $CH_3$ | 4-O-(t-$C_4H_9$)—$C_6H_4$ | $CH_3$ |
| 1791 | $CH_3$ | 4-O-(t-$C_4H_9$)—$C_6H_4$ | $C_2H_5$ |
| 1792 | $CH_3$ | 4-O-(t-$C_4H_9$)—$C_6H_4$ | n-$C_3H_7$ |
| 1793 | $CH_3$ | 4-O-(t-$C_4H_9$)—$C_6H_4$ | i-$C_3H_7$ |
| 1794 | $CH_3$ | 4-O-(t-$C_4H_9$)—$C_6H_4$ | n-$C_4H_9$ |
| 1795 | $CH_3$ | 4-O-(t-$C_4H_9$)—$C_6H_4$ | t-$C_4H_9$ |
| 1796 | $CH_3$ | 4-O-(t-$C_4H_9$)—$C_6H_4$ | n-$C_6H_{13}$ |
| 1797 | $CH_3$ | 4-O-(t-$C_4H_9$)—$C_6H_4$ | Prop-1-en-3-yl |
| 1798 | $CH_3$ | 4-O-(t-$C_4H_9$)—$C_6H_4$ | (E)-1-Chloroprop-1-en-3-yl |
| 1799 | $CH_3$ | 4-O-(t-$C_4H_9$)—$C_6H_4$ | Propyn-3-yl |
| 1800 | $CH_3$ | 4-O-(t-$C_4H_9$)—$C_6H_4$ | 3-Methyl-but-2-en-1-yl |
| 1801 | $CH_3$ | 2-$CF_3$—$C_6H_4$ | H |
| 1802 | $CH_3$ | 2-$CF_3$—$C_6H_4$ | $CH_3$ |
| 1803 | $CH_3$ | 2-$CF_3$—$C_6H_4$ | $C_2H_5$ |
| 1804 | $CH_3$ | 2-$CF_3$—$C_6H_4$ | n-$C_3H_7$ |
| 1805 | $CH_3$ | 2-$CF_3$—$C_6H_4$ | i-$C_3H_7$ |
| 1806 | $CH_3$ | 2-$CF_3$—$C_6H_4$ | n-$C_4H_9$ |
| 1807 | $CH_3$ | 2-$CF_3$—$C_6H_4$ | t-$C_4H_9$ |
| 1808 | $CH_3$ | 2-$CF_3$—$C_6H_4$ | n-$C_6H_{13}$ |
| 1809 | $CH_3$ | 2-$CF_3$—$C_6H_4$ | Prop-1-en-3-yl |
| 1810 | $CH_3$ | 2-$CF_3$—$C_6H_4$ | (E)-1-Chloroprop-1-en-3-yl |
| 1811 | $CH_3$ | 2-$CF_3$—$C_6H_4$ | Propyn-3-yl |
| 1812 | $CH_3$ | 2-$CF_3$—$C_6H_4$ | 3-Methyl-but-2-en-1-yl |
| 1813 | $CH_3$ | 3-$CF_3$—$C_6H_4$ | H |
| 1814 | $CH_3$ | 3-$CF_3$—$C_6H_4$ | $CH_3$ |
| 1815 | $CH_3$ | 3-$CF_3$—$C_6H_4$ | $C_2H_5$ |
| 1816 | $CH_3$ | 3-$CF_3$—$C_6H_4$ | n-$C_3H_7$ |
| 1817 | $CH_3$ | 3-$CF_3$—$C_6H_4$ | i-$C_3H_7$ |
| 1818 | $CH_3$ | 3-$CF_3$—$C_6H_4$ | n-$C_4H_9$ |
| 1819 | $CH_3$ | 3-$CF_3$—$C_6H_4$ | t-C4H, |
| 1820 | $CH_3$ | 3-$CF_3$—$C_6H_4$ | n-$C_6H_{13}$ |
| 1821 | $CH_3$ | 3-$CF_3$—$C_6H_4$ | Prop-1-en-3-yl |
| 1822 | $CH_3$ | 3-$CF_3$—$C_6H_4$ | (E)-1-Chloroprop-1-en-3-yl |
| 1823 | $CH_3$ | 3-$CF_3$—$C_6H_4$ | Propyn-3-yl |
| 1824 | $CH_3$ | 3-$CF_3$—$C_6H_4$ | 3-Methyl-but-2-en-1-yl |
| 1825 | $CH_3$ | 4-$CF_3$—$C_6H_4$ | H |
| 1826 | $CH_3$ | 4-$CF_3$—$C_6H_4$ | $CH_3$ |
| 1827 | $CH_3$ | 4-$CF_3$—$C_6H_4$ | $C_2H_5$ |
| 1828 | $CH_3$ | 4-$CF_3$—$C_6H_4$ | n-$C_3H_7$ |
| 1829 | $CH_3$ | 4-$CF_3$—$C_6H_4$ | i-$C_3H_7$ |
| 1830 | $CH_3$ | 4-$CF_3$—$C_6H_4$ | n-$C_4H_9$ |
| 1831 | $CH_3$ | 4-$CF_3$—$C_6H_4$ | t-$C_4H_9$ |
| 1832 | $CH_3$ | 4-$CF_3$—$C_6H_4$ | n-$C_6H_{13}$ |
| 1833 | $CH_3$ | 4-$CF_3$—$C_6H_4$ | Prop-1-en-3-yl |
| 1834 | $CH_3$ | 4-$CF_3$—$C_6H_4$ | (E)-1-Chloroprop-1-en-3-yl |
| 1835 | $CH_3$ | 4-$CF_3$—$C_6H_4$ | Propyn-3-yl |
| 1836 | $CH_3$ | 4-$CF_3$—$C_6H_4$ | 3-Methyl-but-2-en-1-yl |
| 1837 | $CH_3$ | 2-$NH_2$—$C_6H_4$ | H |
| 1838 | $CH_3$ | 2-$NH_2$—$C_6H_4$ | $CH_3$ |
| 1839 | $CH_3$ | 2-$NH_2$—$C_6H_4$ | $C_2H_5$ |
| 1840 | $CH_3$ | 2-$NH_2$—$C_6H_4$ | n-$C_3H_7$ |
| 1841 | $CH_3$ | 2-$NH_2$—$C_6H_4$ | i-$C_3H_7$ |
| 1842 | $CH_3$ | 2-$NH_2$—$C_6H_4$ | n-$C_4H_9$ |
| 1843 | $CH_3$ | 2-$NH_2$—$C_6H_4$ | t-$C_4H_9$ |
| 1844 | $CH_3$ | 2-$NH_2$—$C_6H_4$ | n-$C_6H_{13}$ |
| 1845 | $CH_3$ | 2-$NH_2$—$C_6H_4$ | Prop-1-en-3-yl |
| 1846 | $CH_3$ | 2-$NH_2$—$C_6H_4$ | (E)-1-Chloroprop-1-en-3-yl |
| 1847 | $CH_3$ | 2-$NH_2$—$C_6H_4$ | Propyn-3-yl |
| 1848 | $CH_3$ | 2-$NH_2$—$C_6H_4$ | 3-Methyl-but-2-en-1-yl |
| 1849 | $CH_3$ | 3-$NH_2$—$C_6H_4$ | H |
| 1850 | $CH_3$ | 3-$NH_2$—$C_6H_4$ | $CH_3$ |
| 1851 | $CH_3$ | 3-$NH_2$—$C_6H_4$ | $C_2H_5$ |
| 1852 | $CH_3$ | 3-$NH_2$—$C_6H_4$ | n-$C_3H_7$ |
| 1853 | $CH_3$ | 3-$NH_2$—$C_6H_4$ | i-$C_3H_7$ |
| 1854 | $CH_3$ | 3-$NH_2$—$C_6H_4$ | n-$C_4H_9$ |
| 1855 | $CH_3$ | 3-$NH_2$—$C_6H_4$ | t-$C_4H_9$ |
| 1856 | $CH_3$ | 3-$NH_2$—$C_6H_4$ | n-$C_6H_{13}$ |
| 1857 | $CH_3$ | 3-$NH_2$—$C_6H_4$ | Prop-1-en-3-yl |
| 1858 | $CH_3$ | 3-$NH_2$—$C_6H_4$ | (E)-1-Ch1oroprop-1-en-3-yl |
| 1859 | $CH_3$ | 3-$NH_2$—$C_6H_4$ | Propyn-3-yl |

TABLE A-continued

| No. | $R^3$ | $R^4$ | $R^5$ |
|---|---|---|---|
| 1860 | $CH_3$ | 3-$NH_2$—$C_6H_4$ | 3-Methyl-but-2-en-1-yl |
| 1861 | $CH_3$ | 4-$NH_2$—$C_6H_4$ | H |
| 1862 | $CH_3$ | 4-$NH_2$—$C_6H_4$ | $CH_3$ |
| 1863 | $CH_3$ | 4-$NH_2$—$C_6H_4$ | $C_2H_5$ |
| 1864 | $CH_3$ | 4-$NH_2$—$C_6H_4$ | n-$C_3H_7$ |
| 1865 | $CH_3$ | 4-$NH_2$—$C_6H_4$ | i-$C_3H_7$ |
| 1866 | $CH_3$ | 4-$NH_2$—$C_6H_4$ | n-$C_4H_9$ |
| 1867 | $CH_3$ | 4-$NH_2$—$C_6H_4$ | t-$C_4H_9$ |
| 1868 | $CH_3$ | 4-$NH_2$—$C_6H_4$ | n-$C_6H_{13}$ |
| 1869 | $CH_3$ | 4-$NH_2$—$C_6H_4$ | Prop-1-en-3-yl |
| 1870 | $CH_3$ | 4-$NH_2$—$C_6H_4$ | (E)-1-Chloroprop-1-en-3-yl |
| 1871 | $CH_3$ | 4-$NH_2$—$C_6H_4$ | Propyn-3-yl |
| 1872 | $CH_3$ | 4-$NH_2$—$C_6H_4$ | 3-Methyl-but-2-en-1-yl |
| 1873 | $CH_3$ | 2-$NMe_2$—$C_6H_4$ | H |
| 1874 | $CH_3$ | 2-$NMe_2$—$C_6H_4$ | $CH_3$ |
| 1875 | $CH_3$ | 2-$NMe_2$—$C_6H_4$ | $C_2H_5$ |
| 1876 | $CH_3$ | 2-$NMe_2$—$C_6H_4$ | n-$C_3H_7$ |
| 1877 | $CH_3$ | 2-$NMe_2$—$C_6H_4$ | i-$C_3H_7$ |
| 1878 | $CH_3$ | 2-$NMe_2$—$C_6H_4$ | n-$C_4H_9$ |
| 1879 | $CH_3$ | 2-$NMe_2$—$C_6H_4$ | t-$C_4H_9$ |
| 1880 | $CH_3$ | 2-$NMe_2$—$C_6H_4$ | n-$C_6H_{13}$ |
| 1881 | $CH_3$ | 2-$NMe_2$—$C_6H_4$ | Prop-1-en-3-yl |
| 1882 | $CH_3$ | 2-$NMe_2$—$C_6H_4$ | (E)-1-Chloroprop-1-en-3-yl |
| 1883 | $CH_3$ | 2-$NMe_2$—$C_6H_4$ | Propyn-3-yl |
| 1884 | $CH_3$ | 2-$NMe_2$—$C_6H_4$ | 3-Methyl-but-2-en-1-yl |
| 1885 | $CH_3$ | 3-$NMe_2$—$C_6H_4$ | H |
| 1886 | $CH_3$ | 3-$NMe_2$—$C_6H_4$ | $CH_3$ |
| 1887 | $CH_3$ | 3-$NMe_2$—$C_6H_4$ | $C_2H_5$ |
| 1888 | $CH_3$ | 3-$NMe_2$—$C_6H_4$ | n-$C_3H_7$ |
| 1889 | $CH_3$ | 3-$NMe_2$—$C_6H_4$ | i-$C_3H_7$ |
| 1890 | $CH_3$ | 3-$NMe_2$—$C_6H_4$ | n-$C_4H_9$ |
| 1891 | $CH_3$ | 3-$NMe_2$—$C_6H_4$ | t-$C_4H_9$ |
| 1892 | $CH_3$ | 3-$NMe_2$—$C_6H_4$ | n-$C_6H_{13}$ |
| 1693 | $CH_3$ | 3-$NMe_2$—$C_6H_4$ | Prop-1-en-3-yl |
| 1894 | $CH_3$ | 3-$NMe_2$—$C_6H_4$ | (E)-1-Chloroprop-1-en-3-yl |
| 1895 | $CH_3$ | 3-$NMe_2$—$C_6H_4$ | Propyn-3-yl |
| 1896 | $CH_3$ | 3-$NMe_2$—$C_6H_4$ | 3-Methyl-but-2-en-1-yl |
| 1897 | $CH_3$ | 4-$NMe_2$—$C_6H_4$ | H |
| 1898 | $CH_3$ | 4-$NMe_2$—$C_6H_4$ | $CH_3$ |
| 1899 | $CH_3$ | 4-$NMe_2$—$C_6H_4$ | $C_2H_5$ |
| 1900 | $CH_3$ | 4-$NMe_2$—$C_6H_4$ | n-$C_3H_7$ |
| 1901 | $CH_3$ | 4-$NMe_2$—$C_6H_4$ | i-$C_3H_7$ |
| 1902 | $CH_3$ | 4-$NMe_2$—$C_6H_4$ | n-$C_4H_9$ |
| 1903 | $CH_3$ | 4-$NMe_2$—$C_6H_4$ | t-$C_4H_9$ |
| 1904 | $CH_3$ | 4-$NMe_2$—$C_6H_4$ | n-$C_6H_{13}$ |
| 1905 | $CH_3$ | 4-$NMe_2$—$C_6H_4$ | Prop-1-en-3-yl |
| 1906 | $CH_3$ | 4-$NMe_2$—$C_6H_4$ | (E)-1-Chloroprop-1-en-3-yl |
| 1907 | $CH_3$ | 4-$NMe_2$—$C_6H_4$ | Propyn-3-yl |
| 1908 | $CH_3$ | 4-$NMe_2$—$C_6H_4$ | 3-Methyl-but-2-en-1-yl |
| 1909 | $CH_3$ | 2-Aminothiocarbo-nyl-$C_6H_4$ | H |
| 1910 | $CH_3$ | 2-Aminothiocarbo-nyl-$C_6H_4$ | $CH_3$ |
| 1911 | $CH_3$ | 2-Aminothiocarbo-nyl-$C_6H_4$ | $C_2H_5$ |
| 1912 | $CH_3$ | 2-Aminothiocarbo-nyl-$C_6H_4$ | n-$C_3H_7$ |
| 1913 | $CH_3$ | 2-Aminothiocarbo-nyl-$C_6H_4$ | i-$C_3H_7$ |
| 1914 | $CH_3$ | 2-Aminothiocarbo-nyl-$C_6H_4$ | n-$C_4H_9$ |
| 1915 | $CH_3$ | 2-Aminothiocarbo-nyl-$C_6H_4$ | t-$C_4H_9$ |
| 1916 | $CH_3$ | 2-Aminothiocarbo-nyl-$C_6H_4$ | n-$C_6H_{13}$ |
| 1917 | $CH_3$ | 2-Aminothiocarbo-nyl-$C_6H_4$ | Prop-1-en-3-yl |
| 1918 | $CH_3$ | 2-Aminothiocarbo-nyl-$C_6H_4$ | (E)-1-Chloroprop-1-en-3-yl |
| 1919 | $CH_3$ | 2-Aminothiocarbo-nyl-$C_6H_4$ | Propyn-3-yl |
| 1920 | $CH_3$ | 2-Aminothiocarbo-nyl-$C_6H_4$ | 3-Methyl-but-2-en-1-yl |
| 1921 | $CH_3$ | 3-Aminothiocarbo-nyl-$C_6H_4$ | H |
| 1922 | $CH_3$ | 3-Aminothiocarbo-nyl-$C_6H_4$ | $CH_3$ |

TABLE A-continued

| No. | $R^3$ | $R^4$ | $R^5$ |
|---|---|---|---|
| 1923 | $CH_3$ | 3-Aminothiocarbo-nyl-$C_6H_4$ | $C_2H_5$ |
| 1924 | $CH_3$ | 3-Aminothiocarbo-nyl-$C_6H_4$ | n-$C_3H_7$ |
| 1925 | $CH_3$ | 3-Aminothiocarbo-nyl-$C_6H_4$ | i-$C_3H_7$ |
| 1926 | $CH_3$ | 3-Aminothiocarbo-nyl-$C_6H_4$ | n-$C_4H_9$ |
| 1927 | $CH_3$ | 3-Aminothiocarbo-nyl-$C_6H_4$ | t-$C_4H_9$ |
| 1928 | $CH_3$ | 3-Aminothiocarbo-nyl-$C_6H_4$ | n-$C_6H_{13}$ |
| 1929 | $CH_3$ | 3-Aminothiocarbo-nyl-$C_6H_4$ | Prop-1-en-3-yl |
| 1930 | $CH_3$ | 3-Aminothiocarbo-nyl-$C_6H_4$ | (E)-1-Chloroprop-1-en-3-yl |
| 1931 | $CH_3$ | 3-Aminothiocarbo-nyl-$C_6H_4$ | Propyn-3-yl |
| 1932 | $CH_3$ | 3-Aminothiocarbo-nyl-$C_6H_4$ | 3-Methyl-but-2-en-1-yl |
| 1933 | $CH_3$ | 4-Aminothiocarbo-nyl-$C_6H_4$ | H |
| 1934 | $CH_3$ | 4-Aminothiocarbo-nyl-$C_6H_4$ | $CH_3$ |
| 1935 | $CH_3$ | 4-Aminothiocarbo-nyl-$C_6H_4$ | $C_2H_5$ |
| 1936 | $CH_3$ | 4-Aminothiocarbo-nyl-$C_6H_4$ | n-$C_3H_7$ |
| 1937 | $CH_3$ | 4-Aminothiocarbo-nyl-$C_6H_4$ | i-$C_3H_7$ |
| 1938 | $CH_3$ | 4-Aminothiocarbo-nyl-$C_6H_4$ | n-$C_4H_9$ |
| 1939 | $CH_3$ | 4-Aminothiocarbo-nyl-$C_6H_4$ | t-$C_4H_9$ |
| 1940 | $CH_3$ | 4-Aminothiocarbo-nyl-$C_6H_4$ | n-$C_6H_{13}$ |
| 1941 | $CH_3$ | 4-Aminothiocarbo-nyl-$C_6H_4$ | Prop-1-en-3-yl |
| 1942 | $CH_3$ | 4-Aminothiocarbo-nyl-$C_6H_4$ | (E)-1-Chloroprop-1-en-3-yl |
| 1943 | $CH_3$ | 4-Aminothiocarbo-nyl-$C_6H_4$ | Propyn-3-yl |
| 1944 | $CH_3$ | 4-Aminothiocarbo-nyl-$C_6H_4$ | 3-Methyl-but-2-en-1-yl |
| 1945 | $CH_3$ | 2-$OCF_3$—$C_6H_4$ | H |
| 1946 | $CH_3$ | 2-$OCF_3$—$C_6H_4$ | $CH_3$ |
| 1947 | $CH_3$ | 2-$OCF_3$—$C_6H_4$ | $C_2H_5$ |
| 1948 | $CH_3$ | 2-$OCF_3$—$C_6H_4$ | n-$C_3H_7$ |
| 1949 | $CH_3$ | 2-$OCF_3$—$C_6H_4$ | i-$C_3H_7$ |
| 1950 | $CH_3$ | 2-$OCF_3$—$C_6H_4$ | n-$C_4H_9$ |
| 1951 | $CH_3$ | 2-$OCF_3$—$C_6H_4$ | t-$C_4H_9$ |
| 1952 | $CH_3$ | 2-$OCF_3$—$C_6H_4$ | n-$C_6H_{13}$ |
| 1953 | $CH_3$ | 2-$C_2H_5$—$C_6H_4$ | i-$C_3H_7$ |
| 1954 | $CH_3$ | 2-$C_2H_5$—$C_6H_4$ | n-$C_4H_9$ |
| 1955 | $CH_3$ | 2-$OCF_3$—$C_6H_4$ | Prop-1-en-3-yl |
| 1956 | $CH_3$ | 2-$OCF_3$—$C_6H_4$ | (E)-1-Chloroprop-1-en-3-yl |
| 1957 | $CH_3$ | 2-$OCF_3$—$C_6H_4$ | Propyn-3-yl |
| 1958 | $CH_3$ | 2-$OCF_3$—$C_6H_4$ | 3-Methyl-but-2-en-1-yl |
| 1959 | $CH_3$ | 3-$OCF_3$—$C_6H_4$ | H |
| 1960 | $CH_3$ | 3-$OCF_3$—$C_6H_4$ | $CH_3$ |
| 1961 | $CH_3$ | 3-$OCF_3$—$C_6H_4$ | $C_2H_5$ |
| 1962 | $CH_3$ | 3-$OCF_3$—$C_6H_4$ | n-$C_3H_7$ |
| 1963 | $CH_3$ | 3-$OCF_3$—$C_6H_4$ | i-$C_3H_7$ |
| 1964 | $CH_3$ | 3-$OCF_3$—$C_6H_4$ | n-$C_4H_9$ |
| 1965 | $CH_3$ | 3-$OCF_3$—$C_6H_4$ | t-$C_4H_9$ |
| 1966 | $CH_3$ | 3-$OCF_3$—$C_6H_4$ | n-$C_6H_{13}$ |
| 1967 | $CH_3$ | 3-$OCF_3$—$C_6H_4$ | Prop-1-en-3-yl |
| 1968 | $CH_3$ | 3-$OCF_3$—$C_6H_4$ | (E)-1-Chloroprop-1-en-3-yl |
| 1969 | $CH_3$ | 3-$OCF_3$—$C_6H_4$ | Propyn-3-yl |
| 1970 | $CH_3$ | 3-$OCF_3$—$C_6H_4$ | 3-Methyl-but-2-en-1-yl |
| 1971 | $CH_3$ | 4-$OCF_3$—$C_6H_4$ | H |
| 1972 | $CH_3$ | 4-$OCF_3$—$C_6H_4$ | $CH_3$ |
| 1973 | $CH_3$ | 4-$OCF_3$—$C_6H_4$ | $C_2H_5$ |
| 1974 | $CH_3$ | 4-$OCF_3$—$C_6H_4$ | n-$C_3H_7$ |
| 1975 | $CH_3$ | 4-$OCF_3$—$C_6H_4$ | i-$C_3H_7$ |
| 1976 | $CH_3$ | 4-$OCF_3$—$C_6H_4$ | n-$C_4H_9$ |
| 1977 | $CH_3$ | 4-$OCF_3$—$C_6H_4$ | t-$C_4H_9$ |

TABLE A-continued

| No. | $R^3$ | $R^4$ | $R^5$ |
|---|---|---|---|
| 1978 | $CH_3$ | 4-$OCF_3$—$C_6H_4$ | n-$C_6H_{13}$ |
| 1979 | $CH_3$ | 4-$OCF_3$—$C_6H_4$ | Prop-1-en-3-yl |
| 1980 | $CH_3$ | 4-$OCF_3$—$C_6H_4$ | (E)-1-Chloroprop-1-en-3-yl |
| 1981 | $CH_3$ | 4-$OCF_3$—$C_6H_4$ | Propyn-3-yl |
| 1982 | $CH_3$ | 4-$OCF_3$—$C_6H_4$ | 3-Methyl-but-2-en-1-yl |
| 1983 | $CH_3$ | 2-$SCH_3$—$C_6H_4$ | H |
| 1984 | $CH_3$ | 2-$SCH_3$—$C_6H_4$ | $CH_3$ |
| 1985 | $CH_3$ | 2-$SCH_3$—$C_6H_4$ | $C_2H_5$ |
| 1986 | $CH_3$ | 2-$SCH_3$—$C_6H_4$ | n-$C_3H_7$ |
| 1987 | $CH_3$ | 2-$SCH_3$—$C_6H_4$ | i-$C_3H_7$ |
| 1988 | $CH_3$ | 2-$SCH_3$—$C_6H_4$ | n-$C_4H_9$ |
| 1989 | $CH_3$ | 2-$SCH_3$—$C_6H_4$ | t-$C_4H_9$ |
| 1990 | $CH_3$ | 2-$SCH_3$—$C_6H_4$ | n-$C_6H_{13}$ |
| 1991 | $CH_3$ | 2-$SCH_3$—$C_6H_4$ | Prop-1-en-3-yl |
| 1992 | $CH_3$ | 2-$SCH_3$—$C_6H_4$ | (E)-1-Chloroprop-1-en-3-yl |
| 1993 | $CH_3$ | 2-$SCH_3$—$C_6H_4$ | Propyn-3-yl |
| 1994 | $CH_3$ | 2-$SCH_3$—$C_6H_4$ | 3-Methyl-but-2-en-1-yl |
| 1995 | $CH_3$ | 3-$SCH_3$—$C_6H_4$ | H |
| 1996 | $CH_3$ | 3-$SCH_3$—$C_6H_4$ | $CH_3$ |
| 1997 | $CH_3$ | 3-$SCH_3$—$C_6H_4$ | $C_2H_5$ |
| 1998 | $CH_3$ | 3-$SCH_3$—$C_6H_4$ | n-$C_3H_7$ |
| 1999 | $CH_3$ | 3-$SCH_3$—$C_6H_4$ | i-$C_3H_7$ |
| 2000 | $CH_3$ | 3-$SCH_3$—$C_6H_4$ | n-$C_4H_9$ |
| 2001 | $CH_3$ | 3-$SCH_3$—$C_6H_4$ | t-$C_4H_9$ |
| 2002 | $CH_3$ | 3-$SCH_3$—$C_6H_4$ | n-$C_6H_{13}$ |
| 2003 | $CH_3$ | 3-$SCH_3$—$C_6H_4$ | Prop-1-en-3-yl |
| 2004 | $CH_3$ | 3-$SCH_3$—$C_6H_4$ | (E)-1-Chloroprop-1-en-3-yl |
| 2005 | $CH_3$ | 3-$SCH_3$—$C_6H_4$ | Propyn-3-yl |
| 2006 | $CH_3$ | 3-$SCH_3$—$C_6H_4$ | 3-Methyl-but-2-en-1-yl |
| 2007 | $CH_3$ | 4-$SCH_3$—$C_6H_4$ | H |
| 2008 | $CH_3$ | 4-$SCH_3$—$C_6H_4$ | $CH_3$ |
| 2009 | $CH_3$ | 4-$SCH_3$—$C_6H_4$ | $C_2H_5$ |
| 2010 | $CH_3$ | 4-$SCH_3$—$C_6H_4$ | n-$C_3H_7$ |
| 2011 | $CH_3$ | 4-$SCH_3$—$C_6H_4$ | i-$C_3H_7$ |
| 2012 | $CH_3$ | 4-$SCH_3$—$C_6H_4$ | n-$C_4H_9$ |
| 2013 | $CH_3$ | 4-$SCH_3$—$C_6H_4$ | t-$C_4H_9$ |
| 2014 | $CH_3$ | 4-$SCH_3$—$C_6H_4$ | n-$C_6H_{13}$ |
| 2015 | $CH_3$ | 4-$SCH_3$—$C_6H_4$ | Prop-1-en-3-yl |
| 2016 | $CH_3$ | 4-$SCH_3$—$C_6H_4$ | (E)-1-Chloroprop-1-en-3-yl |
| 2017 | $CH_3$ | 4-$SCH_3$—$C_6H_4$ | Propyn-3-yl |
| 2018 | $CH_3$ | 4-$SCH_3$—$C_6H_4$ | 3-Methyl-but-2-en-1-yl |
| 2019 | $CH_3$ | 2-Methyl-sulfonyl-$C_6H_4$ | H |
| 2020 | $CH_3$ | 2-Methyl-sulfonyl-$C_6H_4$ | $CH_3$ |
| 2021 | $CH_3$ | 2-Methyl-sulfonyl-$C_6H_4$ | $C_2H_5$ |
| 2022 | $CH_3$ | 2-Methyl-sulfonyl-$C_6H_4$ | n-$C_3H_7$ |
| 2023 | $CH_3$ | 2-Methyl-sulfonyl-$C_6H_4$ | i-$C_3H_7$ |
| 2024 | $CH_3$ | 2-Methyl-sulfonyl-$C_6H_4$ | n-$C_4H_9$ |
| 2025 | $CH_3$ | 2-Methyl-sulfonyl-$C_6H_4$ | t-$C_4H_9$ |
| 2026 | $CH_3$ | 2-Methyl-sulfonyl-$C_6H_4$ | n-$C_6H_{13}$ |
| 2027 | $CH_3$ | 2-Methyl-sulfonyl-$C_6H_4$ | Prop-1-en-3-yl |
| 2028 | $CH_3$ | 2-Methyl-sulfonyl-$C_6H_4$ | (E)-1-Chloroprop-1-en-3-yl |
| 2029 | $CH_3$ | 2-Methyl-sulfonyl-$C_6H_4$ | Propyn-3-yl |
| 2030 | $CH_3$ | 2-Methyl-sulfonyl-$C_6H_4$ | 3-Methyl-but-2-en-1-yl |
| 2031 | $CH_3$ | 3-Methyl-sulfonyl-$C_6H_4$ | H |
| 2032 | $CH_3$ | 3-Methyl-sulfonyl-$C_6H_4$ | $CH_3$ |
| 2033 | $CH_3$ | 3-Methyl-sulfonyl-$C_6H_4$ | $C_2H_5$ |
| 2034 | $CH_3$ | 3-Methyl-sulfonyl-$C_6H_4$ | n-$C_3H_7$ |
| 2035 | $CH_3$ | 3-Methyl-sulfonyl-$C_6H_4$ | i-$C_3H_7$ |
| 2036 | $CH_3$ | 3-Methyl-sulfonyl-$C_6H_4$ | n-$C_4H_9$ |

TABLE A-continued

| No. | $R^3$ | $R^4$ | $R^5$ |
|---|---|---|---|
| 2037 | $CH_3$ | 3-Methyl-sulfonyl-$C_6H_4$ | t-$C_4H_9$ |
| 2038 | $CH_3$ | 3-Methyl-sulfonyl-$C_6H_4$ | n-$C_6H_{13}$ |
| 2039 | $CH_3$ | 3-Methyl-sulfonyl-$C_6H_4$ | Prop-1-en-3-yl |
| 2040 | $CH_3$ | 3-Methyl-sulfonyl-$C_6H_4$ | (E)-1-Chloroprop-1-en-3-yl |
| 2041 | $CH_3$ | 3-Methyl-sulfonyl-$C_6H_4$ | Propyn-3-yl |
| 2042 | $CH_3$ | 3-Methyl-sulfonyl-$C_6H_4$ | 3-Methyl-but-2-en-1-yl |
| 2043 | $CH_3$ | 4-Methyl-sulfonyl-$C_6H_4$ | H |
| 2044 | $CH_3$ | 4-Methyl-sulfonyl-$C_6H_4$ | $CH_3$ |
| 2045 | $CH_3$ | 4-Methyl-sulfonyl-$C_6H_4$ | $C_2H_5$ |
| 2046 | $CH_3$ | 4-Methyl-sulfonyl-$C_6H_4$ | n-$C_3H_7$ |
| 2047 | $CH_3$ | 4-Methyl-sulfonyl-$C_6H_4$ | i-$C_3H_7$ |
| 2048 | $CH_3$ | 4-Methyl-sulfonyl-$C_6H_4$ | n-$C_4H_9$ |
| 2049 | $CH_3$ | 4-Methyl-sulfonyl-$C_6H_4$ | t-$C_4H_9$ |
| 2050 | $CH_3$ | 4-Methyl-sulfonyl-$C_6H_4$ | n-$C_6H_{13}$ |
| 2051 | $CH_3$ | 4-Methyl-sulfonyl-$C_6H_4$ | Prop-1-en-3-yl |
| 2052 | $CH_3$ | 4-Methyl-sulfonyl-$C_6H_4$ | (E)-1-Chloroprop-1-en-3-yl |
| 2053 | $CH_3$ | 4-Methyl-sulfonyl-$C_6H_4$ | Propyn-3-yl |
| 2054 | $CH_3$ | 4-Methyl-sulfonyl-$C_6H_4$ | 3-Methyl-but-2-en-1-yl |
| 2055 | $CH_3$ | 2-Methoxycarbo-nyl-$C_6H_4$ | H |
| 2056 | $CH_3$ | 2-Methoxycarbo-nyl-$C_6H_4$ | $CH_3$ |
| 2057 | $CH_3$ | 2-Methoxycarbo-nyl-$C_6H_4$ | $C_2H_5$ |
| 2058 | $CH_3$ | 2-Methoxycarbo-nyl-$C_6H_4$ | n-$C_3H_7$ |
| 2059 | $CH_3$ | 2-Methoxycarbo nyl-$C_6H_4$ | i-$C_3H_7$ |
| 2060 | $CH_3$ | 2-Methoxycarbo-nyl-$C_6H_4$ | n-$C_4H_9$ |
| 2061 | $CH_3$ | 2-Methoxycarbo-nyl-$C_6H_4$ | t-$C_4H_9$ |
| 2062 | $CH_3$ | 2-Methoxycarbo-nyl-$C_6H_4$ | n-$C_6H_{13}$ |
| 2063 | $CH_3$ | 2-Methoxycarbo-nyl-$C_6H_4$ | Prop-1-en-3-yl |
| 2064 | $CH_3$ | 2-Methoxycarbo-nyl-$C_6H_4$ | (E)-1-Chloroprop-1-en-3-yl |
| 2065 | $CH_3$ | 2-Methoxycarbo-nyl-$C_6H_4$ | Propyn-3-yl |
| 2066 | $CH_3$ | 2-Methoxycarbo-nyl-$C_6H_4$ | 3-Methyl-but-2-en-1-yl |
| 2067 | $CH_3$ | 3-Methoxycarbo-nyl-$C_6H_4$ | H |
| 2068 | $CH_3$ | 3-Methoxycarbo-nyl-$C_6H_4$ | $CH_3$ |
| 2069 | $CH_3$ | 3-Methoxycarbo-nyl-$C_6H_4$ | $C_2H_5$ |
| 2070 | $CH_3$ | 3-Methoxycarbo-nyl-$C_6H_4$ | n-$C_3H_7$ |
| 2071 | $CH_3$ | 3-Methoxycarbo-nyl-$C_6H_4$ | i-$C_3H_7$ |
| 2072 | $CH_3$ | 3-Methoxycarbo-nyl-$C_6H_4$ | n-$C_4H_9$ |
| 2073 | $CH_3$ | 3-Methoxycarbo-nyl-$C_6H_4$ | t-$C_4H_9$ |
| 2074 | $CH_3$ | 3-Methoxycarbo-nyl-$C_6H_4$ | n-$C_6H_{13}$ |
| 2075 | $CH_3$ | 3-Methoxycarbo-nyl-$C_6H_4$ | Prop-1-en-3-yl |

TABLE A-continued

| No. | $R^3$ | $R^4$ | $R^5$ |
|---|---|---|---|
| 2076 | $CH_3$ | 3-Methoxycarbo-nyl-$C_6H_4$ | (E)-1-Chloroprop-1-en-3-yl |
| 2077 | $CH_3$ | 3-Methoxycarbo-nyl-$C_6H_4$ | Propyn-3-yl |
| 2078 | $CH_3$ | 3-Methoxycarbo-nyl-$C_6H_4$ | 3-Methyl-but-2-en-1-yl |
| 2079 | $CH_3$ | 4-Methoxycarbo-nyl-$C_6H_4$ | H |
| 2080 | $CH_3$ | 4-Methoxycarbo-nyl-$C_6H_4$ | $CH_3$ |
| 2081 | $CH_3$ | 4-Methoxycarbo-nyl-$C_6H_4$ | $C_2H_5$ |
| 2082 | $CH_3$ | 4-Methoxycarbo-nyl-$C_6H_4$ | n-$C_3H_7$ |
| 2083 | $CH_3$ | 4-Methoxycarbo-nyl-$C_6H_4$ | i-$C_3H_7$ |
| 2084 | $CH_3$ | 4-Methoxycarbo-nyl-$C_6H_4$ | n-$C_4H_9$ |
| 2085 | $CH_3$ | 4-Methoxycarbo-nyl-$C_6H_4$ | t-$C_4H_9$ |
| 2086 | $CH_3$ | 4-Methoxycarbo-nyl-$C_6H_4$ | n-$C_6H_{13}$ |
| 2087 | $CH_3$ | 4-Methoxycarbo-nyl-$C_6H_4$ | Prop-1-en-3-yl |
| 2088 | $CH_3$ | 4-Methoxycarbo-nyl-$C_6H_4$ | (E)-1-Chloroprop-1-en-3-yl |
| 2089 | $CH_3$ | 4-Methoxycarbo-nyl-$C_6H_4$ | Propyn-3-yl |
| 2090 | $CH_3$ | 4-Methoxycarbo-nyl-$C_6H_4$ | 3-Methyl-but-2-en-1-yl |
| 2091 | $CH_3$ | 2-Ethoxy-carbonyl-$C_6H_4$ | H |
| 2092 | $CH_3$ | 2-Ethoxy-carbonyl-$C_6H_4$ | $CH_3$ |
| 2093 | $CH_3$ | 2-Ethoxy-carbonyl-$C_6H_4$ | $C_2H_5$ |
| 2094 | $CH_3$ | 2-Ethoxy-carbonyl-$C_6H_4$ | n-$C_3H_7$ |
| 2095 | $CH_3$ | 2-Ethoxy-carbonyl-$C_6H_4$ | i-$C_3H_7$ |
| 2096 | $CH_3$ | 2-Ethoxy-carbonyl-$C_6H_4$ | n-$C_4H_9$ |
| 2097 | $CH_3$ | 2-Ethoxy-carbonyl-$C_6H_4$ | t-$C_4H_9$ |
| 2098 | $CH_3$ | 2-Ethoxy-carbonyl-$C_6H_4$ | n-$C_6H_{13}$ |
| 2099 | $CH_3$ | 2-Ethoxy-carbonyl-$C_6H_4$ | Prop-1-en-3-yl |
| 2100 | $CH_3$ | 2-Ethoxy-carbonyl-$C_6H_4$ | (E)-1-Chloroprop-1-en-3-yl |
| 2101 | $CH_3$ | 2-Ethoxy-carbonyl-$C_6H_4$ | Propyn-3-yl |
| 2102 | $CH_3$ | 2-Ethoxy-carbonyl-$C_6H_4$ | 3-Methyl-but-2-en-1-yl |
| 2103 | $CH_3$ | 3-Ethoxy-carbonyl-$C_6H_4$ | H |
| 2104 | $CH_3$ | 3-Ethoxy-carbonyl-$C_6H_4$ | $CH_3$ |
| 2105 | $CH_3$ | 3-Ethoxy-carbonyl-$C_6H_4$ | $C_2H_5$ |
| 2106 | $CH_3$ | 3-Ethoxy-carbonyl-$C_6H_4$ | n-$C_3H_7$ |
| 2107 | $CH_3$ | 3-Ethoxy-carbonyl-$C_6H_4$ | i-$C_3H_7$ |
| 2108 | $CH_3$ | 3-Ethoxy-carbonyl-$C_6H_4$ | n-$C_4H_9$ |
| 2109 | $CH_3$ | 3-Ethoxy-carbonyl-$C_6H_4$ | t-$C_4H_9$ |
| 2110 | $CH_3$ | 3-Ethoxy-carbonyl-$C_6H_4$ | n-$C_6H_{13}$ |
| 2111 | $CH_3$ | 3-Ethoxy-carbonyl-$C_6H_4$ | Prop-1-en-3-yl |
| 2112 | $CH_3$ | 3-Ethoxy-carbonyl-$C_6H_4$ | (E)-1-Chloroprop-1-en-3-yl |
| 2113 | $CH_3$ | 3-Ethoxy-carbonyl-$C_6H_4$ | Propyn-3-yl |

TABLE A-continued

| No. | $R^3$ | $R^4$ | $R^5$ |
|---|---|---|---|
| 2114 | $CH_3$ | 3-Ethoxy-carbonyl-$C_6H_4$ | 3-Methyl-but-2-en-1-yl |
| 2115 | $CH_3$ | 4-Ethoxy-carbonyl-$C_6H_4$ | H |
| 2116 | $CH_3$ | 4-Ethoxy-carbonyl-$C_6H_4$ | $CH_3$ |
| 2117 | $CH_3$ | 4-Ethoxy-carbonyl-$C_6H_4$ | $C_2H_5$ |
| 2118 | $CH_3$ | 4-Ethoxy-carbonyl-$C_6H_4$ | n-$C_3H_7$ |
| 2119 | $CH_3$ | 4-Ethoxy-carbonyl-$C_6H_4$ | i-$C_3H_7$ |
| 2120 | $CH_3$ | 4-Ethoxy-carbonyl-$C_6H_4$ | n-$C_4H_9$ |
| 2121 | $CH_3$ | 4-Ethoxy-carbonyl-$C_6H_4$ | t-$C_4H_9$ |
| 2122 | $CH_3$ | 4-Ethoxy-carbonyl-$C_6H_4$ | n-$C_6H_{13}$ |
| 2123 | $CH_3$ | 4-Ethoxy-carbonyl-$C_6H_4$ | Prop-1-en-3-yl |
| 2124 | $CH_3$ | 4-Ethoxy-carbonyl-$C_6H_4$ | (E)-1-Chloroprop-1-en-3-yl |
| 2125 | $CH_3$ | 4-Ethoxy-carbonyl-$C_6H_4$ | Propyn-3-yl |
| 2126 | $CH_3$ | 4-Ethoxy-carbonyl-$C_6H_4$ | 3-Methyl-but-2-en-1-yl |
| 2127 | $CH_3$ | 2-Amino-carbonyl-$C_6H_4$ | H |
| 2128 | $CH_3$ | 2-Amino-carbonyl-$C_6H_4$ | $CH_3$ |
| 2129 | $CH_3$ | 2-Amino-carbonyl-$C_6H_4$ | $C_2H_5$ |
| 2130 | $CH_3$ | 2-Amino-carbonyl-$C_6H_4$ | n-$C_3H_7$ |
| 2131 | $CH_3$ | 2-Amino-carbonyl-$C_6H_4$ | i-$C_3H_7$ |
| 2132 | $CH_3$ | 2-Amino-carbonyl-$C_6H_4$ | n-$C_4H_9$ |
| 2133 | $CH_3$ | 2-Amino-carbonyl-$C_6H_4$ | t-$C_4H_9$ |
| 2134 | $CH_3$ | 2-Amino-carbonyl-$C_6H_4$ | n-$C_6H_{13}$ |
| 2135 | $CH_3$ | 2-Amino-carbonyl-$C_6H_4$ | Prop-1-en-3-yl |
| 2136 | $CH_3$ | 2-Amino-carbonyl-$C_6H_4$ | (E)-1-Chloroprop-1-en-3-yl |
| 2137 | $CH_3$ | 2-Amino-carbonyl-$C_6H_4$ | Propyn-3-yl |
| 2138 | $CH_3$ | 2-Amino-carbonyl-$C_6H_4$ | 3-Methyl-but-2-en-1-yl |
| 2139 | $CH_3$ | 3-Amino-carbonyl-$C_6H_4$ | H |
| 2140 | $CH_3$ | 3-Amino-carbonyl-$C_6H_4$ | $CH_3$ |
| 2141 | $CH_3$ | 3-Amino-carbonyl-$C_6H_4$ | $C_2H_5$ |
| 2142 | $CH_3$ | 3-Amino-carbonyl-$C_6H_4$ | n-$C_3H_7$ |
| 2143 | $CH_3$ | 3-Amino-carbonyl-$C_6H_4$ | i-$C_3H_7$ |
| 2144 | $CH_3$ | 3-Amino-carbonyl-$C_6H_4$ | n-$C_4H_9$ |
| 2145 | $CH_3$ | 3-Amino-carbonyl-$C_6H_4$ | t-$C_4H_9$ |
| 2146 | $CH_3$ | 3-Amino-carbonyl-$C_6H_4$ | n-$C_6H_{13}$ |
| 2147 | $CH_3$ | 3-Amino-carbonyl-$C_6H_4$ | Prop-1-en-3-yl |
| 2148 | $CH_3$ | 3-Amino-carbonyl-$C_6H_4$ | (E)-1-Chloroprop-1-en-3-yl |
| 2149 | $CH_3$ | 3-Amino-carbonyl-$C_6H_4$ | Propyn-3-yl |
| 2150 | $CH_3$ | 3-Amino-carbonyl-$C_6H_4$ | 3-Methyl-but-2-en-1-yl |
| 2151 | $CH_3$ | 4-Amino-carbonyl-$C_6H_4$ | H |
| 2152 | $CH_3$ | 4-Amino-carbonyl-$C_6H_4$ | $CH_3$ |
| 2153 | $CH_3$ | 4-Amino-carbonyl-$C_6H_4$ | $C_2H_5$ |
| 2154 | $CH_3$ | 4-Amino-carbonyl-$C_6H_4$ | n-$C_3H_7$ |
| 2155 | $CH_3$ | 4-Amino-carbonyl-$C_6H_4$ | i-$C_3H_7$ |
| 2156 | $CH_3$ | 4-Amino-carbonyl-$C_6H_4$ | n-$C_4H_9$ |
| 2157 | $CH_3$ | 4-Amino-carbonyl-$C_6H_4$ | t-$C_4H_9$ |
| 2158 | $CH_3$ | 4-Amino-carbonyl-$C_6H_4$ | n-$C_6H_{13}$ |
| 2159 | $CH_3$ | 4-Amino-carbonyl-$C_6H_4$ | Prop-1-en-3-yl |
| 2160 | $CH_3$ | 4-Amino-carbonyl-$C_6H_4$ | (E)-1-Chloroprop-1-en-3-yl |
| 2161 | $CH_3$ | 4-Amino-carbonyl-$C_6H_4$ | Propyn-3-yl |
| 2162 | $CH_3$ | 4-Amino-carbonyl-$C_6H_4$ | 3-Methyl-but-2-en-1-yl |
| 2163 | $CH_3$ | 2-(N-Methylamino-carbonyl)-$C_6H_4$ | H |
| 2164 | $CH_3$ | 2-(N-Methylamino-carbonyl)-$C_6H_4$ | $CH_3$ |
| 2165 | $CH_3$ | 2-(N-Methylamino-carbonyl)-$C_6H_4$ | $C_2H_5$ |
| 2166 | $CH_3$ | 2-(N-Methylamino-carbonyl)-$C_6H_4$ | n-$C_3H_7$ |
| 2167 | $CH_3$ | 2-(N-Methylamino-carbonyl)-$C_6H_4$ | i-$C_3H_7$ |
| 2168 | $CH_3$ | 2-(N-Methylamino-carbonyl)-$C_6H_4$ | n-$C_4H_9$ |
| 2169 | $CH_3$ | 2-(N-Methylamino-carbonyl)-$C_6H_4$ | t-$C_4H_9$ |
| 2170 | $CH_3$ | 2-(N-Methylamino-carbonyl)-$C_6H_4$ | n-$C_6H_{13}$ |
| 2171 | $CH_3$ | 2-(N-Methylamino-carbonyl)-$C_6H_4$ | Prop-1-en-3-yl |
| 2172 | $CH_3$ | 2-(N-Methylamino-carbonyl)-$C_6H_4$ | (E)-1-Chloroprop-1-en-3-yl |
| 2173 | $CH_3$ | 2-(N-Methylamino-carbonyl)-$C_6H_4$ | Propyn-3-yl |
| 2174 | $CH_3$ | 2-(N-Methylamino-carbonyl)-$C_6H_4$ | 3-Methyl-but-2-en-1-yl |
| 2175 | $CH_3$ | 3-(N-Methylamino-carbonyl)-$C_6H_4$ | H |
| 2176 | $CH_3$ | 3-(N-Methylamino-carbonyl)-$C_6H_4$ | $CH_3$ |
| 2177 | $CH_3$ | 3-(N-Methylamino-carbonyl)-$C_6H_4$ | $C_2H_5$ |
| 2178 | $CH_3$ | 3-(N-Methylamino-carbonyl)-$C_6H_4$ | n-$C_3H_7$ |
| 2179 | $CH_3$ | 3-(N-Methylamino-carbonyl)-$C_6H_4$ | i-$C_3H_7$ |
| 2180 | $CH_3$ | 3-(N-Methylamino-carbonyl)-$C_6H_4$ | n-$C_4H_9$ |
| 2181 | $CH_3$ | 3-(N-Methylamino-carbonyl)-$C_6H_4$ | t-$C_4H_9$ |
| 2182 | $CH_3$ | 3-(N-Methylamino-carbonyl)-$C_6H_4$ | n-$C_6H_{13}$ |
| 2183 | $CH_3$ | 3-(N-Methylamino-carbonyl)-$C_6H_4$ | Prop-1-en-3-yl |
| 2184 | $CH_3$ | 3-(N-Methylamino-carbonyl)-$C_6H_4$ | (E)-1-Chloroprop-1-en-3-yl |
| 2185 | $CH_3$ | 3-(N-Methylamino-carbonyl)-$C_6H_4$ | Propyn-3-yl |
| 2186 | $CH_3$ | 3-(N-Methylamino-carbonyl)-$C_6H_4$ | 3-Methyl-but-2-en-1-yl |
| 2187 | $CH_3$ | 4-(N-Methylamino-carbonyl)-$C_6H_4$ | H |
| 2188 | $CH_3$ | 4-(N-Methylamino-carbonyl)-$C_6H_4$ | $CH_3$ |
| 2189 | $CH_3$ | 4-(N-Methylamino-carbonyl)-$C_6H_4$ | $C_2H_5$ |
| 2190 | $CH_3$ | 4-(N-Methylamino-carbonyl)-$C_6H_4$ | n-$C_3H_7$ |

TABLE A-continued

| No. | $R^3$ | $R^4$ | $R^5$ |
|---|---|---|---|
| 2191 | $CH_3$ | 4-(N-Methylamino-carbonyl)-$C_6H_4$ | i-$C_3H_7$ |
| 2192 | $CH_3$ | 4-(N-Methylamino-carbonyl)-$C_6H_4$ | n-$C_4H_9$ |
| 2193 | $CH_3$ | 4-(N-Methylamino-carbonyl)-$C_6H_4$ | t-$C_4H_9$ |
| 2194 | $CH_3$ | 4-(N-Methylamino-carbonyl)-$C_6H_4$ | n-$C_6H_{13}$ |
| 2195 | $CH_3$ | 4-(N-Methylamino-carbonyl)-$C_6H_4$ | Prop-1-en-3-yl |
| 2196 | $CH_3$ | 4-(N-Methylamino-carbonyl)-$C_6H_4$ | (E)-1-Chloroprop-1-en-3-yl |
| 2197 | $CH_3$ | 4-(N-Methylamino-carbonyl)-$C_6H_4$ | Propyn-3-yl |
| 2198 | $CH_3$ | 4-(N-Methylamino-carbonyl)-$C_6H_4$ | 3-Methyl-but-2-en-1-yl |
| 2199 | $CH_3$ | 2-Dimethylamino-carbonyl-$C_6H_4$ | H |
| 2200 | $CH_3$ | 2-Dimethylamino-carbonyl-$C_6H_4$ | $CH_3$ |
| 2201 | $CH_3$ | 2-Dimethylamino-carbonyl-$C_6H_4$ | $C_2H_5$ |
| 2202 | $CH_3$ | 2-Dimethylamino-carbonyl-$C_6H_4$ | n-$C_3H_7$ |
| 2203 | $CH_3$ | 2-Dimethylamino-carbonyl-$C_6H_4$ | i-$C_3H_7$ |
| 2204 | $CH_3$ | 2-Dimethylamino-carbonyl-$C_6H_4$ | n-$C_4H_9$ |
| 2205 | $CH_3$ | 2-Dimethylamino-carbonyl-$C_6H_4$ | t-$C_4H_9$ |
| 2206 | $CH_3$ | 2-Dimethylamino-carbonyl-$C_6H_4$ | n-$C_6H_{13}$ |
| 2207 | $CH_3$ | 2-Dimethylamino-carbonyl-$C_6H_4$ | Prop-1-en-3-yl |
| 2208 | $CH_3$ | 2-Dimethylamino-carbonyl-$C_6H_4$ | (E)-1-Chloroprop-1-en-3-yl |
| 2209 | $CH_3$ | 2-Dimethylamino-carbonyl-$C_6H_4$ | Propyn-3-yl |
| 2210 | $CH_3$ | 2-Dimethylamino-carbonyl-$C_6H_4$ | 3-Methyl-but-2-en-1-yl |
| 2211 | $CH_3$ | 3-Dimethylamino-carbonyl-$C_6H_4$ | H |
| 2212 | $CH_3$ | 3-Dimethylamino-carbonyl-$C_6H_4$ | $CH_3$ |
| 2213 | $CH_3$ | 3-Dimethylamino-carbonyl-$C_6H_4$ | $C_2H_5$ |
| 2214 | $CH_3$ | 3-Dimethylamino-carbonyl-$C_6H_4$ | n-$C_3H_7$ |
| 2215 | $CH_3$ | 3-Dimethylamino-carbonyl-$C_6H_4$ | i-$C_3H_7$ |
| 2216 | $CH_3$ | 3-Dimethylamino-carbonyl-$C_6H_4$ | n-$C_4H_9$ |
| 2217 | $CH_3$ | 3-Dimethylamino-carbonyl-$C_6H_4$ | t-$C_4H_9$ |
| 2218 | $CH_3$ | 3-Dimethylamino-carbonyl-$C_6H_4$ | n-$C_6H_{13}$ |
| 2219 | $CH_3$ | 3-Dimethylamino-carbonyl-$C_6H_4$ | Prop-1-en-3-yl |
| 2220 | $CH_3$ | 3-Dimethylamino-carbonyl-$C_6H_4$ | (E)-1-Chloroprop-1-en-3-yl |
| 2221 | $CH_3$ | 3-Dimethylamino-carbonyl-$C_6H_4$ | Propyn-3-yl |
| 2222 | $CH_3$ | 3-Dimethylamino-carbonyl-$C_6H_4$ | 3-Methyl-but-2-en-1-yl |
| 2223 | $CH_3$ | 4-Dimethylamino-carbonyl-$C_6H_4$ | H |
| 2224 | $CH_3$ | 4-Dimethylamino-carbonyl-$C_6H_4$ | $CH_3$ |
| 2225 | $CH_3$ | 4-Dimethylamino-carbonyl-$C_6H_4$ | $C_2H_5$ |
| 2226 | $CH_3$ | 4-Dimethylamino-carbonyl-$C_6H_4$ | n-$C_3H_7$ |
| 2227 | $CH_3$ | 4-Dimethylamino-carbonyl-$C_6H_4$ | i-$C_3H_7$ |
| 2228 | $CH_3$ | 4-Dimethylamino-carbonyl-$C_6H_4$ | n-$C_4H_9$ |
| 2229 | $CH_3$ | 4-Dimethylamino-carbonyl-$C_6H_4$ | t-$C_4H_9$ |
| 2230 | $CH_3$ | 4-Dimethylamino-carbonyl-$C_6H_4$ | n-$C_6H_{13}$ |
| 2231 | $CH_3$ | 4-Dimethylamino-carbonyl-$C_6H_4$ | Prop-1-en-3-yl |
| 2232 | $CH_3$ | 4-Dimethylamino-carbonyl-$C_6H_4$ | (E)-1-Chloroprop-1-en-3-yl |
| 2233 | $CH_3$ | 4-Dimethylamino-carbonyl-$C_6H_4$ | Propyn-3-yl |
| 2234 | $CH_3$ | 4-Dimethylamino-carbonyl-$C_6H_4$ | 3-Methyl-but-2-en-1-yl |

The compounds I are suitable as fungicides.

The compounds I are distinguished by an outstanding activity against a broad spectrum of phytopathogenic fungi, in particular from the class of the Ascomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybean, coffee, sugar cane, grapes, fruit and decorative plants and vegetable plants such as cucumbers, beans and cucurbits, and on the seeds of these plants.

They are specifically suitable for the control of the following plant diseases: Erysiphe graminis (powdery mildew) in cereals, Erysiphe cichoracearum and Sphaerotheca fuliginea on cucurbits, Podosphaera leucotricha on apples, Uncinula necator on vines, Puccinia species on cereals, Rhizoctonia species on cotton and lawns, Ustilago species on cereals and sugar cane, Venturia inaequalis (scab) on apples, Helminthosporium species on cereals, Septoria nodorum on wheat, Botrytis cinerea (gray mold) on strawberries, vines, Cercospora arachidicola on groundnuts, Pseudocercosporella herpotrichoides on wheat, barley, Pyricularia oryzae on rice, Phytophthora infestans on potatoes and tomatoes, Fusarium and Verticillium species on various plants, Plasmopara viticola on vines, Alternaria species on vegetables and fruit.

The compounds I are applied by treating the fungi or the plants, seeds, materials or the soil to be protected from fungal attack with a fungicidally effective amount of the active compounds. They are applied before or after the infection of the materials, plants or seeds by the fungi.

They can be converted into the customary formulations, such as solutions, emulsions, suspensions, dusts, powders, pastes and granules. The application form depends on the particular intended use; it should in any case guarantee a fine and uniform dispersion of the ortho-substituted benzyl ester of a cyclopropanecarboxylic acid. The formulations are prepared in a known manner, eg. by extending the active compound with solvents and/or carriers, if desired using emulsifiers and dispersants, it also being possible to use other organic solvents as auxiliary solvents when water is used as a diluent. Suitable auxiliary substances for this purpose are essentially: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90% by weight of active compound.

Depending on the type of effect desired, the application rates are from 0.01 to 2.0 kg of active compound per ha.

In seed treatment, active compound amounts of from 0.001 to 0.1 g, preferably from 0.01 to 0.05 g, per kilogram of seed are in general needed.

The compositions according to the invention can also be present in the application form as fungicides together with other active compounds, the eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfides, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)-phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazole carbamate, 2-methoxycarbonylaminobenzimidazole, 2-(fur-2-yl) benzimidazole, 2-(thiazol-4-yl)benzimidazole, N-(1,1,2, 2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diyl-bis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and also various fungicides, such as dodecylguanidine acetate, 3-[3-(3,5-dimethyl-2-oxycyclohexyl)-2-hydroxyethyl]glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl) methyl)-1H-1,2,4-triazole.

The compounds of the formula I are additionally suitable for controlling pests from the class of insects, arachnids and nematodes effectively. They can be employed as pesticides in plant protection and in the hygiene, stored products protection and veterinary sectors.

The harmful insects include from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica* 12*-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala,* Phyllophaga sp., *Phyllopertha horticola, Phyllotreta nemorum, Phyllotreta striolata, Popillia japonica, Sitona lineatus, Sitophilus granaria.*

From the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina* [sic], *Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterous insects (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active compounds can be applied as such or in the form of their formulations or the application forms prepared therefrom, eg. in the form of directly sprayable solutions, powders, suspensions or dispersions, emulsions, oil dispersions, pastes, dusts, scattering compositions or granules by spraying, atomizing, dusting, scattering or pouring. The application forms depend entirely on the purposes of use; they should in any case as far as possible guarantee the finest dispersion of the active compounds according to the invention.

The active compound concentrations in the ready-for-application preparations can be varied within quite substantial ranges.

In general, they are from 0.0001 to 10%, preferably from 0.01 to 1%.

The active compounds can also be used with great success in ultra-low volume processes (ULV), where it is possible to apply formulations containing more than 95% by weight of active compound or even the active compound without additives.

The application rate of active compound for controlling pests under outdoor conditions is from 0.1 to 2.0, preferably from 0.2 to 1.0 kg/ha.

For the preparation of directly sprayable solutions, emulsions, pastes or oil dispersions, mineral oil fractions of medium to high boiling point, such as kerosene or diesel oil, and also coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water are suitable.

Aqueous application forms can be prepared from emulsion concentrates, pastes or wettable powders (oil dispersions) by addition of water. For the preparation of emulsions, pastes or oil dispersions, the substances can be homogenized in water as such or dissolved in an oil or solvent, by means of wetting agents, tackifiers, dispersants or emulsifiers. However, concentrates consisting of active substance, wetting agent, tackifier, dispersant or emulsifier and possibly solvent or oil can also be prepared, which are suitable for dilution with water.

Suitable surface-active substances are alkali metal, alkaline earth metal and ammonium salts of lignosulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ether, condensation products of sulfonated naphthalene and naphthalene derivatives with formaldehyde, condensation products of naphthalene or of naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ether, ethoxylated polyoxypropylene, lauryl alcohol polyglycol ether acetal, sorbitol esters, lignin-sulfite waste liquors and methylcellulose.

Powders, scattering compositions and dusts can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably 95% to 100% (according to NMR spectrum).

Examples of formulations are:

I. 5 parts by weight of a compound according to the invention are intimately mixed with 95 parts by weight of finely divided kaolin. A dust which contains 5% by weight of the active compound is obtained in this way.

II. 30 parts by weight of a compound according to the invention are intimately mixed with a mixture of 92 parts by weight of powdered silica gel and 8 parts by weight of paraffin oil which has been sprayed on the surface of this silica gel. A preparation of the active compound having good adhesion is obtained in this way (active compound content 23% by weight).

III. 10 parts by weight of a compound according to the invention are dissolved in a mixture which consists of 90 parts by weight of xylene, 6 parts by weight of the addition product of 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are well mixed with 3 parts by weight of the sodium salt of diisobutylnaphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of a compound according to the invention are mixed with 10 parts by weight of N-methyl-α-pyrrolidone and a solution is obtained which is suitable for application in the form of very small drops (active compound content 90% by weight).

VII. 20 parts by weight of a compound according to the invention are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of a compound according to the invention are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray liquor is obtained which contains 0.1% by weight of the active compound.

Granules, eg. coated, impregnated and homogeneous granules, can be produced by binding the active compounds to solid carriers. Solid carriers are eg. mineral earths, such as silica gel, silicic acids, silica gels silicates, talc, kaolin, attapulgite, limestone, lime, chalk, bole, loess, clay, dolomite, diatomaceous earth, calcium sulfate and magnesium sulfate, magnesium oxide, ground synthetic materials, fertilizers, such as eg. ammonium sulfate, ammonium phosphate, ammonium nitrate, ureas and vegetable products, such as grain meal, tree bark, wood and nut shell meal, cellulose powder and other solid carriers.

Oils of various types, herbicides, fungicides, other pesticides and bactericides can be added to the active compounds, if appropriate even only immediately before application (tank mix). These agents can be admixed to the compositions according to the invention in the weight ratio 1:10–10:1.

SYNTHESIS EXAMPLES

The procedures presented in the synthesis examples below were utilized with appropriate modification of the starting compounds to obtain further compounds I. The compounds thus obtained are shown in the following tables with physical data.

Example 1

Preparation of Methyl (E,E)-2-methoxyimino-2-[2'-(1"-methyl, 1"-acetyl)iminooxymethyl]phenylacetate 21 g (0.21 mol) of diacetyl monoxime are added under protective gas and with slight cooling at room temperature to 6.4 g (0.21 mol) of sodium hydride (80%) in 150 ml of dry dimethylformamide and the mixture is stirred for 30 min at room temperature. A solution of 60 g (0.21 mol) of methyl 2-methoxyimino-2-(2'bromomethyl)phenylacetate in 360 ml of dimethylformamide is then added dropwise and the mixture is stirred at room temperature for 16 h. After addition of 10% strength hydrochloric acid, it is extracted with methyl tert-butyl ether. The combined organic phases are washed with water, dried over $Na_2SO_4$ and concentrated. The residue is suspended in a little cold methanol. After filtering off with suction, 38 g (59%) of the title compound are obtained as light brown crystals having a melting point of 69–71° C.

$^1$H-NMR ($CDCl_3$):δ=1.87(s,3H); 2.30(s,3H); 3.85(s,3H); 4.05(s,3H); 5.15(s,2H); 7.17–7.48(m,4H) ppm.

Example 2

Preparation of Methyl (E,E,E)-2-methoxyimino-2-[2'-(1"-methyl, 1"-(1"'-ethoxyiminoethyl)) iminooxymethyl]phenylacetate 0.96 g (9.8 mmol) of O-ethylhydroxylamine hydrochloride and 0.6 g of dry molecular sieve beads (3 A) are added to a solution of 2.5 g (8.2 mmol) of methyl (E,E)-2-methoxyimino-2-[2'-(1"-methyl, 1"-acetyl) iminooxymethyl]phenylacetate in 60 ml of warm methanol after cooling to room temperature and the mixture is allowed to stand at room temperature for 5 days. After filtering off the molecular sieve, the solution is concentrated, the residue is partitioned between methyl tert-butyl ether and water, and the organic phase is washed with water, dried over $Na_2SO_4$ and concentrated. After triturating the residue with n-hexane and filtering off with suction, 1.8 g (63%) of the title compound are obtained as pale yellow crystals having a melting point of 69–72° C.

$^1$H-NMR ($CDCl_3$):δ=1.27(t,3H); 1.96(s,3H); 1.99(s,3H); 3.84(s,3H); 4.04(s,3H); 4.17(q,2H); 5.06(s,2H); 7.17–7.49 (m,4H) ppm Example 3

Preparation of (E,E,E)-2-methoxyimino-2-[2'-(1"-methyl, 1"-(1"'-ethoxyiminoethyl))iminooxymethyl] phenylacetic Acid Monomethylamide 0.90 g (2.60 mmol) of methyl (E,E,E)-2-methoxyimino-2-[2'-(1"-methyl,1"-(1"'-ethoxyiminoethyl)) iminooxymethyl]-phenylacetate is dissolved in 50 ml of tetrahydrofuran, treated with 2.0 g of 40% strength aqueous monomethylamine solution and stirred at room temperature for 16 h. The mixture is then treated with water and extracted with methyl tert-butyl ether, and the organic phase is washed with water, dried over $Na_2SO_4$ and concentrated on a rotary evaporator. As a residue, 0.80 g (89%) of the title compound remains as a pale yellow oil.

$^1$H-NMR ($CDCl_3$):δ=1.28(t,3H); 1.97(s,3H); 1.99(s,3H); 2.90(d,3H); 3.96(s,3H); 4.18(q,2H); 5.07(s,2H); 6.74(br,1H) ;7.17–7.48(m,4H) ppm.

Example 4

Preparation of 4-hydroxyimino-2,2-dimethylpentan-3-one

A solution of 40 g of hydrogen chloride in 156 g of diethyl ether is added dropwise at room temperature to 96 g (0.84 mol) of 2,2-dimethyl-3-pentanone in 960 g of toluene. After cooling to −10° C., a solution of 95 g of n-butyl nitrite in 470 g of diethyl ether is added dropwise. The mixture is stirred at from −10° C. to 0° C. for 4 hours and then allowed to come to room temperature. After a total of 16 h, the reaction mixture is washed three times with 1 l of ice-water each time and then extracted twice with 1 l of 1M sodium hydroxide solution each time. The alkaline phase is separated off and neutralized with 20% strength sulfuric acid. The crude product is filtered off with suction and, after drying, recrystallized from n-hexane. 66 g (55%) of the title compound are obtained as a pale yellow powder of melting point 107–110° C.

$^1$H-NMR ($CDCl_3$):δ=1.29(s,9H); 1.99(s,3H); 8.30(s,1H) ppm.

Example 5

Preparation of Methyl (E)-2-methoxyimino-2-[2'-(1"-methyl, 1"-(1"',1"'-dimethylethylcarbonyl)) iminooxymethyl]phenylacetate 25 g (0.17 mol) of 4-hydroxyimino-2,2-dimethylpentan-3-one are added in portions under protective gas to 6.4 g (0.21 mol) of sodium hydride (80%) in 150 ml of dry dimethylformamide, the reaction mixture warming to 50° C. Stirring is continued for 30 min, then a solution of 50 g (0.17 mol) of methyl 2-methoxyimino-2-(2'-bromomethyl) phenylacetate in 300 ml of dimethylformamide is added dropwise and the mixture is stirred at room temperature for 16 h. After addition of 10% strength hydrochloric acid, it is extracted with methyl tert-butyl ether. The combined organic phases are washed with water, dried over $Na_2SO_2$ [sic] and concentrated. The black oily residue is purified by column chromatography on silica gel (methyl tert-butyl ether/n-hexane) and the product thus obtained is suspended in ice-cold methanol. After filtering off with suction, 24 g (41%) of the title compound are obtained as an almost colorless powder of melting point 58–62° C.

$^1$H-NMR ($CDCl_3$):δ=1.19(s,9H); 1.90(s,3H); 3.83(s,3H); 4.04(s,3H); 5.11(s,2H); 7.18–7.45(m,4H) ppm.

Example 6

Preparation of Methyl (E)-2-methoxyimino-2-[2'-(1"-methyl, 1"-(1"'-(6""-(4""'-chlorophenyl) hexyloxyimino), 2"',2"'-dimethylpropyl)) iminooxymethyl]phenylacetate 5.9 g (26 mmol) of O-6-(4'-chlorophenyl) hexylhydroxylamine, 3.6 g of dry molecular sieve beads (3 A) and 1.6 g (8.6 mmol) of p-toluenesulfonic acid hydrate are added to a solution of 3.0 g (8.6 mmol) of methyl (E)-2-methoxyimino-2-[2'-(1"-methyl, 1"-(1"',1"'-dimethylethylcarbonyl))iminooxymethyl]phenylacetate in 60 ml of warm methanol after cooling to room temperature and the mixture is refluxed for 3 h. After filtering off the molecular sieve, the solution is concentrated, the residue is partitioned between methyl tert-butyl ether and water, and the organic phase is washed with water, dried over $Na_2SO_4$ and concentrated. After column chromatography on silica gel (hexane/methyl tert-butyl ether), 3.8 g (79%) of the title compound are obtained as a pale yellow oil.

$^1$H-NMR ($CDCl_3$):δ=1.09(s,9H); 1.26–1.42(m,4H); 1.52–1.67(m,4H); 1.90(s,3H); 2.57(t,2H); 3.84(s,3H); 3.99 (t,2H); 4.03(s,3H); 5.02(s,2H); 7.07–7.47(m,8H) ppm.

Example 7

Preparation of (E)-2-methoxyimino-2-[2'-(1"-methyl, 1"-(1"'-(6""-(4""'-chlorophenyl) hexyloxyimino), 2"', 2"'-dimethylpropyl)) iminooxymethyl]phenylacetic Acid Monomethylamide 2.8 g (5.0 mmol) of methyl (E)-2-methoxyimino-2-[2'-(1"-methyl, 1"-(1"'-(6""-(4""'-chlorophenyl)

hexyloxyimino), 2"', 2"'-dimethylpropyl)iminooxymethyl] phenylacetate are dissolved in 10 ml of tetrahydrofuran, treated with 3.9 g of 40% strength aqueous monomethylamine solution and stirred at room temperature for 16 h. The mixture is then treated with water and extracted with methyl tert-butyl ether, and the organic phase is washed with water, dried over $Na_2SO_4$ and concentrated on a rotary evaporator. As a residue, 2.3 g (82%) of the title compound remain as a colorless oil.

$^1$H-NMR ($CDCl_3$):δ=1.08(s,9H); 1.26–1.41(m,4H); 1.53–1.67(m,4H); 1.89(s,3H); 2.56(t,2H); 2.87(d,3H); 3.93 (s,3H); 3.99(t,2H); 5.02(s,2H); 6.74(s,broad,1H); 7.05–7.45 (m,8H) ppm.

Example 8

Preparation of (E)-2-methoxyimino-2-[2'-(1"-methyl, 1"(1"'-methoxyimino, 1"'paramethoxyphenyl)methyl)iminooxymethyl] phenylacetic Acid Monomethylthioamide (Cpd. II.01, Table II)

1.9 g (4.5 mmol) of (E)-2-methoxyimino-2-[2'-(1"-methyl, 1"(1"'-methoxyimino, 1"'paramethoxyphenyl) methyl)iminooxymethyl]phenylacetic acid monomethylamide are dissolved in 80 ml of xylene, treated with 1.8 g (4.5 mmol) of Lawesson's reagent and stirred at 100° C. for 45 min.

The reaction solution is concentrated and the residue is purified by column chromatography.

1.5 g (75%) of the title compound are isolated as an isomer mixture in the form of a yellowish oil.

IR [cm$^{-1}$] Film:

834, 977, 1027, 1065, 1175, 1251, 1358, 1512, 1608, 2936, 3330

Example 9

Isomerization of (E)-2-methoxyimono-2-[2'-(1"-methyl, 1"-(1"'-(Z/E)methoxyimino, 1"'-phenyl) methyl)-(E)-iminooxymethyl]phenylacetic Acid Monomethylamide to (E)-2-methoxyimino-2-[2'-(1"-methyl, 1"-(1"'-(E)-methoxyimino, 1"'-phenyl) methyl]-(E)-iminooxymethyl]phenylacetic Acid Monomethylamide 5 g of E,E,E/E,Z,E isomer mixture (30:70) are dissolved in 50 ml of methanol, treated with 15 ml of methanol saturated with HCl and allowed to stand at room temperature for 18 hours. The reaction solution is added to ice-water and extracted with dichloromethane, and the extract is dried over $Na_2SO_4$. After concentrating on the rotary evaporator, 5 g of an oil (E,E,E:E,Z,E, approx. 65:35) are obtained. The desired (E,E,E)-isomer crystallizes on addition of methanol (2.1 g=42%) in the form of a colorless solid.

M.p. (E,E,E-isomer): 134–136° C.

Note: The filtrate can be isomerized again using methanol HCl.

TABLE I

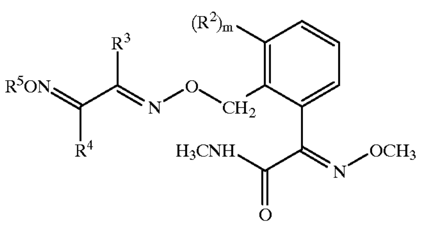

| No. | $R^2_m$ | $R^3$ | $R^4$ | $R^5$ | Data |
|---|---|---|---|---|---|
| I.01 | H | $CH_3$ | $CH_3$ | H | m.p.: 135–138° C. |
| I.02 | H | $CH_3$ | $CH_3$ | $CH_3$ | m.p.: 78–82° C. |
| I.03 | H | $CH_3$ | $CH_3$ | $C_2H_5$ | oil; IR(Film): 3350, 2975, 2937, 1669, 1526, 1366, 1092, 1039, 980, 920, 890 |
| I.04 | H | $CH_3$ | $CH_3$ | i-$C_3H_7$ | oil; $^1$H-NMR($CDCl_3$)I: δ = 1.26(d,6H); 1.95(s,3H); 2.0(s,3H); 2.91(d,3H); 3.96(s,3H); 4.37(q,1H); 5.06(s,2H); 6.72(s,br,1H); 7.17–7.50(m,4H) ppm |
| I.05 | H | $CH_3$ | $CH_3$ | n-$C_4H_9$ | m.p.: 89–93° C. |
| I.06 | H | $CH_3$ | $CH_3$ | t-$C_4H_9$ | oil; $^1$H-NMR($CDCl_3$): δ = 1.29(s,9H); 1.94(s,3H); 2.00(s,3H); 2.90(d,3H); 3.96(s,3H); 5.06(s,2H); 6.70(s,br,1H); 7.17–747(m,4H) ppm |
| I.07 | H | $CH_3$ | $CH_3$ | n-$C_6H_{13}$ | m.p.: 83–85° C. |

TABLE I-continued

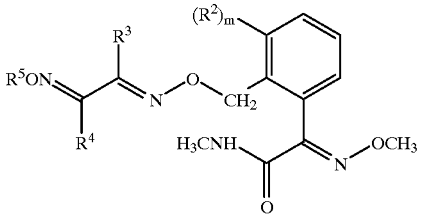

| No. | $R^2_m$ | $R^3$ | $R^4$ | $R^5$ | Data |
|---|---|---|---|---|---|
| I.08 | H | $CH_3$ | $CH_3$ | $CH_2CN$ | m.p.: 92–96° C. |
| I.09 | H | $CH_3$ | $CH_3$ | $CH_2CH_2CN$ | m.p.: 92–96° C. |
| I.10 | H | $CH_3$ | $CH_3$ | 3-Methyl-but-2-en-1-yl | m.p.: 86–88° C. |
| I.11 | H | $CH_3$ | $CH_3$ | 4-Cl—$C_6H_4$—$CH_2$ | m.p.: 152–154° C. |
| I.12 | H | $CH_3$ | $CH_3$ | 2-Naphthyl-$CH_2$ | oil; $^1$H-NMR($CDCl_3$): δ = 1.98(s,3H); 2.02(s,3H) 2.87(d,3H); 3.92(s,3H); 5.06(s,2H); 5.33(s,2H); 6.70(s,br,1H); 7.17–7,88(m,11H) ppm |
| I.13 | H | $CH_3$ | $CH_3$ | 6-(4'-Chloro-phenyl)hex-1-yl | oil; $^1$H-NMR($CDCl_3$): δ = 1.27–1.70(m,8H); 1.95(s,3H); 1.98(s,3H); 2.58(t,2H); 2.90(d,3H); 3.95(s,3H); 4.10(t,2H); 5.06(s,2H); 6.71(s,br,1H); 7.08–7.46(m,8H) ppm |
| I.14 | H | $CH_3$ | $CH_3$ | 3-$CF_3$—$C_6H_4$ | m.p.: 119–124° C. |
| I.15 | H | $CH_3$ | $CH_3$ | 4-$CF_3$, 6-Cl-py-rid-2-yl | m.p.: 129–132° C. |
| I.16 | H | $CH_3$ | $CH_3$ | 4-$CF_3$-pyrid-2-yl | m.p.: 144–147° C. |
| I.17 | H | $CH_3$ | $CH_3$ | (E)-1-Chloropro-pen-3-yl | m.p.: 96–98° C. |
| I.18 | H | $CH_3$ | $CH_3$ | (E)-4-(4'-Chlorophenyl)-but-2-en-1-yl | oil; $^1$H-NMR($CDCl_3$): 1.97(s,6H); 2.90(d,3H); 3.36(d,2H); 3.96(s,3H); 4.60(d,2H); 5.06(s,2H); 5.65–5,92(m,2H); 7.68(s,br,1H); 7.09–7,48(m,8H) ppm |
| I.19 | H | $CH_3$ | $CH_3$ | Propyn-3-yl | m.p.: 106–109° C. |
| I.20 | H | $CH_3$ | $CH_3$ | 2-Hydroxy-prop-1-yl | JR: 884, 929, 980, 1036, 1092, 1366, 1529, 1665, 2937, 3370 |
| I.21 | H | $CH_3$ | $CH_3$ | 6-Hydroxy-2-me-thyl-pyrimi-din-4-ylmethyl | 217–220° C. |
| I.22 | H | $CH_3$ | $CH_3$ | 6-Hydroxy-2-iso-propyl-pyrimi din-4-ylmethyl | 219–221° C. |
| I.23 | H | $CH_3$ | $CH_3$ | 6-Hydroxy-2-cy-clopropyl-pyri-midin-4-ylmethyl | 220–224° C. |
| I.24 | H | $CH_3$ | $CH_3$ | 5-(2'-Furan)-pent-1-yl | 57–61° C. |
| I.25 | H | $CH_3$ | $CH_3$ | 5-(2'-N-Methyl-pyrrol)-pent-1-yl | 40–44° C. |
| I.26 | H | $CH_3$ | $CH_3$ | 2-(4'-Chloro-phenyl)-oxazol-4-ylmethyl | 110–120° C. |
| I.27 | H | $CH_3$ | $CH_3$ | 3-Trifluoro-methylpyrid-2-yl | 104–107° C. |

TABLE I-continued

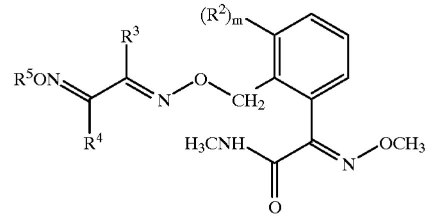

| No. | $R^2_m$ | $R^3$ | $R^4$ | $R^5$ | Data |
|---|---|---|---|---|---|
| I.28 | H | $CH_3$ | $CH_3$ | 5-Trifluoro-methylpyrid-2-yl | 126–130° C. |
| I.29 | H | $CH_3$ | $CH_3$ | 6-(2'-Thio-phen)-hex-1-yl | 694, 893, 980, 1037, 1092, 1365, 1525, 1673, 2935, 3340, 3400 |
| I.30 | H | $CH_3$ | t-$C_4H_9$ | H | oil; $^1$H-NMR($CDCl_3$): δ = 1.10(s,9H); 1.95(s,3H); 2.88(d,3H); 3.95(s,3H); 5.05(s,2H); 6.76(s,br,1H); 7.17–7,47(m,4H); 8.04(s,1H) ppm |
| I.31 | H | $CH_3$ | t-$C_4H_9$ | $CH_3$ | oil; IR (Film): 3360, 2963, 2936, 1671, 1525, 1364, 1091, 1041, 979, 887 |
| I.32 | H | $CH_3$ | t-$C_4H_9$ | $C_2H_5$ | oil; IR (Film): 3350, 2969, 2935, 1669, 1524, 1364, 1093, 1041, 978, 917, 883 |
| I.33 | H | $CH_3$ | t-$C_4H_9$ | i-$C_3H_7$ | m.p.: 95–99° C. |
| I.34 | H | $CH_3$ | t-$C_4H_9$ | n-$C_4H_9$ | oil; IR (Film): 3360, 2958, 2935, 2872, 1671, 1525, 1364, 1092, 1037, 979, 922 |
| I.35 | H | $CH_3$ | t-$C_4H_9$ | t-$C_4H_9$ | m.p.: 89–92° C. |
| I.36 | H | $CH_3$ | t-$C_4H_9$ | n-$C_6H_{13}$ | oil; IR (Film): 3360, 2956, 2933, 2870, 1675, 1525, 1364, 1093, 1039, 979, 918 |
| I.37 | H | $CH_3$ | t-$C_4H_9$ | (E)-1-Chloro-propen-3-yl | oil; IR (Film): 3360, 2966, 2935, 1673, 1526, 1365, 1093, 1037, 980, 918, 881 |
| I.38 | H | $CH_3$ | t-$C_4H_9$ | Propyn-3-yl | oil; IR (Film): 3300, 2967, 2935, 1672, 1525, 1365, 1094, 1037, 1005, 979, 918 |
| I.39 | H | $CH_3$ | t-$C_4H_9$ | 3-Methyl-but-2-en-1-yl | oil; IR (Film): 3360, 2968, 2935, 1675, 1525, 1364, 1093, 1038, 979, 919, 880 |
| I.40 | H | $CH_3$ | t-$C_4H_9$ | 2-Naphthyl-$CH_2$ | oil; IR (Film): 3360, 2966, 2935, 1675, 1523, 1364, 1037, 1002, 979, 920, 752 |
| I.41 | H | $CH_3$ | t-$C_4H_9$ | 4-Cl—$C_6H_4$—$CH_2$ | oil; IR (Film): 3360, 2970, 2945, 1677, 1525, 1492, 1365, 1090, 1038, 1014, 980, 919, 881 |
| I.42 | H | $CH_3$ | t-$C_4H_9$ | (E)-4-(4'-Chlorophenyl)-but-2-en-1-yl | oil; IR (Film): 3360, 2967, 1676, 1525, 1491, 1365, 1093, 1037, 1015, |

TABLE I-continued

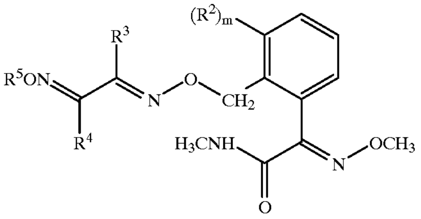

| No. | $R^2_m$ | $R^3$ | $R^4$ | $R^5$ | Data |
|---|---|---|---|---|---|
| | | | | | 979, 919 |
| I.43 | H | $CH_3$ | t-$C_4H_9$ | 6-(4'-Chloro-phenyl)hex-1-yl | oil; IR (Film): 3360, 2934, 1679, 1524, 1492, 1364, 1092, 1038, 1015, 979 |
| I.44 | H | $CH_3$ | t-$C_4H_9$ | 3-$CF_3$—$C_6H_4$ | oil; IR (Film): 3360, 2975, 1675, 1450, 1331, 1168, 1126, 1092, 1038, 980, 940, 926 |
| I.45 | H | $CH_3$ | $C_6H_5$ | H | m.p.: 165–167° C. |
| I.46 | H | $CH_3$ | $C_6H_5$ | $CH_3$ | m.p.: 134–136° C. |
| I.47 | H | $CH_3$ | $C_6H_5$ | $C_2H_5$ | oil; IR (Film): 3340, 2938, 1674, 1526, 1445, 1091, 1037, 979, 925, 767, 694 |
| I.48 | H | $CH_3$ | $C_6H_5$ | i-$C_3H_7$ | m.p.: 77–80° C. |
| I.49 | H | $CH_3$ | $C_6H_5$ | n-$C_4H_9$ | oil; IR (Film): 3340, 2958, 2936, 1675, 1525, 1445, 1092, 1070, 1036, 979, 694 |
| I.50 | H | $CH_3$ | $C_6H_5$ | 4-Cl—$C_6H_4$—$CH_2$ | oil; IR (Film): 3340, 2937, 1675, 1522, 1492, 1445, 1091, 1036, 1012, 979, 918 |
| I.51 | H | $CH_3$ | $C_6H_5$ | 3-$CF_3$—$C_6H_4$ | oil; IR (Film): 3340, 2930, 1675, 1449, 1328, 1169, 1126, 1062, 1038, 979, 944, 697 |
| I.52 | H | $CH_3$ | $C_6H_5$ | 6-(4'-Chloro-phenyl)hex-1-yl | oil; IR (Film): 3340, 2935, 2858, 1679, 1524, 1492, 1445, 1091, 1037, 1015, 979 |
| I.53 | H | $CH_3$ | $C_6H_5$ | (E)-4-(4'-Chlorophenyl)-but-2-en-1-yl | oil; IR (Film): 3340, 2937, 1675, 1525, 1491, 1444, 1092, 1036, 1015, 978, 918 |
| I.54 | H | $C_6H_5$ | $C_6H_5$ | $CH_3$ | m.p.: 60–65° C. |
| I.55 | H | $C_6H_5$ | $C_6H_5$ | $C_2H_5$ | m.p.: 45–48° C. |
| I.56 | H | $C_6H_5$ | $C_6H_5$ | n-$C_3H_7$ | oil, IR [$cm^{-1}$] (Film) 693, 766, 980, 1037, 1064, 1445, 1526, 1676, 2937, 2965, 3330, 3410 |
| I.57 | H | $C_6H_5$ | $C_6H_5$ | i-$C_3H_7$ | m.p.: 53–58° C. |
| I.58 | H | $C_6H_5$ | $C_6H_5$ | n-$C_4H_9$ | oil, IR [$cm^{-1}$] (Film) 693, 766, 978, 1015, 1036, 1445, 1525, 1677, 2936, 2958, 3340, 3420 |
| I.59 | H | $C_6H_5$ | $C_6H_5$ | t-$C_4H_9$ | m.p.: 45–50° C. |
| I.60 | H | $C_6H_5$ | $C_6H_5$ | n-$C_6H_{13}$ | oil, IR [$cm^{-1}$] (Film) 693, 766, 979, 1014, 1037, 1445, 1525, 1678, 2934, 2954, 3330, 3410 |
| I.61 | H | $C_6H_5$ | $C_6H_5$ | 3-Methyl-but-2-en-1-yl | oil, IR [$cm^{-1}$] (Film) 693, 766, 921, 979, 1037, 1445, 1493, |

TABLE I-continued

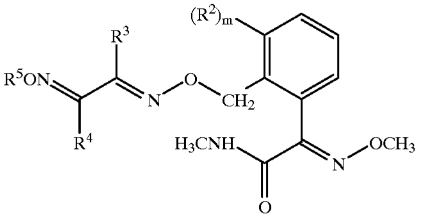

| No. | $R^2_m$ | $R^3$ | $R^4$ | $R^5$ | Data |
|---|---|---|---|---|---|
| | | | | | 1526, 1675, 2937, 3330, 3410 |
| I.62 | H | $CH_3$ | $CH_3$ | 4-Phenyl-but-1-yl | oil, IR [$cm^{-1}$] (Film) 700, 748, 894, 923, 979, 1037, 1365, 1524, 1673, 2938, 3340, 3410 |
| I.63 | H | $CH_3$ | $CH_3$ | 4-Phenoxy-but-1-yl | oil, IR [$cm^{-1}$] (Film) 755, 891, 980, 1037, 1245, 1498, 1525, 1600, 1674, 2939, 3350, 3410 |
| I.64 | H | $CH_3$ | $CH_3$ | 2-(2'-Fluoro-phenoxy)eth-1-yl | oil, IR [$cm^{-1}$] (Film) 749, 889, 924, 979, 1037, 1260, 1366, 1507, 1524, 1673, 2930, 3340, 3410 |
| I.65 | H | $CH_3$ | $CH_3$ | 3-(2'-Fluoro-phenoxy)-prop-1-yl | oil, IR [$cm^{-1}$] (Film) 749, 979, 1037, 1204, 1260, 1280, 1366, 1507, 1524, 1675, 2930, 3340, 3420 |
| I.66 | H | $CH_3$ | $CH_3$ | E-4-(2'-Fluoro-phenoxy)-but-1-yl | oil, IR [$cm^{-1}$] (Film) 749, 891, 980, 1037, 1205, 1259, 1366, 1507, 1524, 1675, 2930, 3340, 3420 |
| I.67 | H | $CH_3$ | $CH_3$ | 6-(4'-Chloro-phenoxy)-hex-1-yl | m.p.: 58–62° C. |
| I.68 | H | $CH_3$ | $CH_3$ | 2-(4'-Chloro-phenoxy)-prop-1-yl | oil, IR [$cm^{-1}$] (Film) 885, 979, 1007, 1037, 1091, 1241, 1366, 1490, 1525, 1674, 2930, 3340, 3420 |
| I.69 | H | $CH_3$ | $CH_3$ | $C_6H_5$—$C_2H_4$-O-$C_2H_4$- | oil, IR [$cm^{-1}$] (Film) 893, 920, 979, 1038, 1092, 1124, 1365, 1524, 1674, 2937, 3350, 3420 |
| I.70 | H | $CH_3$ | $CH_3$ | E-4-(3'-Methoxy-phenyl)-but-3-en-1-yl | oil, IR [$cm^{-1}$] (Film) 890, 978, 1038, 1156, 1365, 1525, 1579, 1598, 1675, 2937, 3320, 3390 |
| I.71 | H | $CH_3$ | $CH_3$ | E-4-(4'-Fluoro-phenyl)-but-3-en-l-yl | m.p.: 77–81° C. |
| I.72 | H | $CH_3$ | $CH_3$ | (3-Bromoisox-azol-5-yl)-methyl | IR [$cm^{-1}$] (Film) 769, 889, 904, 951, 988, 1001, 1035, 1359, 1526, 1677, 3420 |
| I.73 | H | $CH_3$ | $CH_3$ | (3-$CF_3$-isoxazol-5-yl)-methyl | IR [$cm^{-1}$] (KBr) 769, 893, 987, 999, 1034, 1150, 1192, 1221, 1674, 3430 |
| I.74 | H | $CH_3$ | $CH_3$ | (3-iso-Propylis-oxazol-5-yl)-methyl | oil, IR [$cm^{-1}$] (Film) 883, 900, 980, 1000, 1036, 1366, 1525, 1673, 2937, 2968, 3340 |
| I.75 | H | $CH_3$ | $CH_3$ | (3-Cyclopropyl-isoxazol-5-yl)- | oil, IR [$cm^{-1}$] (Film) 883, 907, 980, 1000, |

TABLE I-continued

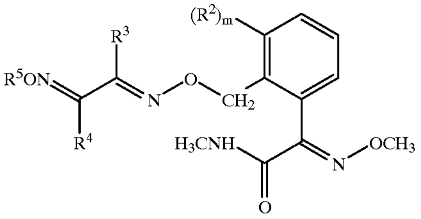

| No. | $R^2_m$ | $R^3$ | $R^4$ | $R^5$ | Data |
|---|---|---|---|---|---|
| | | | | methyl | 1036, 1366, 1434, 1526, 1608, 1673, 2930, 3340 |
| I.76 | H | $CH_3$ | $CH_3$ | (3-iso-Propyl-1,2,4-Oxadiazol-5-yl)-methyl | oil, IR [$cm^{-1}$] (Film) 882, 979, 1019, 1037, 1091, 1366, 1525, 1674, 2938, 2972, 3340 |
| I.77 | H | $CH_3$ | $CH_3$ | 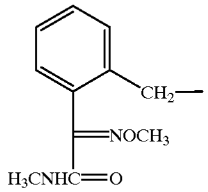 | m.p.: 160–165° C. |
| I.78 | H | $CH_3$ | 4-$OCH_3$—$C_6H_4$ | $CH_3$ | m.p.: 121–125° C. |
| I.79 | H | $CH_3$ | 4-$OCH_3$—$C_6H_4$ | $C_2H_5$ | oil, IR [$cm^{-1}$] (Film) 922, 979, 1036, 1091, 1176, 1252, 1512, 1608, 1675, 2937, 3340 |
| I.80 | H | $CH_3$ | 4-$OCH_3$—$C_6H_4$ | n-$C_3H_7$ | oil, IR [$cm^{-1}$] (Film) 979, 1037, 1067, 1176, 1252, 1512, 1608, 1676, 2936, 2965, 3350 |
| I.81 | H | $CH_3$ | 4-$OCH_3$—$C_6H_4$ | i-$C_3H_7$ | oil, IR [$cm^{-1}$] (Film) 977, 1037, 1122, 1174, 1252, 1512, 1608, 1676, 2937, 2974, 3340 |
| I.82 | H | $CH_3$ | 4-$OCH_3$—$C_6H_4$ | n-$C_4H_9$ | oil, IR [$cm^{-1}$] (Film) 835, 978, 1035, 1176, 1252, 1512, 1608, 1675, 2936, 2958, 3340 |
| I.83 | H | $CH_3$ | 4-$OCH_3$—$C_6H_4$ | t-$C_4H_9$ | IR [$cm^{-1}$] (Film) 958, 979, 1036, 1174, 1191, 1253, 1364, 1513, 1609, 1678, 2930, 2970, 3420 |
| I.84 | H | $CH_3$ | $C_6H_5$ | 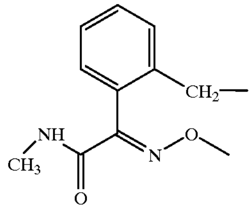 | m.p.: 120–124° C. |
| I.85 | H | $CH_3$ | $C_6H_5$ | 3-Fluorobenzyl | oil, IR [$cm^{-1}$] (Film) 695, 919, 979, 1002, 1036, 1447, 1488, 1525, 1591, 1676, 2920, 3330, 3410 |
| I.86 | H | $CH_3$ | $C_6H_5$ | 3-Bromobenzyl | oil, IR [$cm^{-1}$] (Film) |

TABLE I-continued

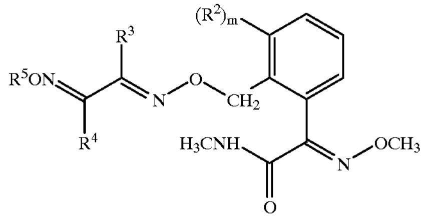

| No. | $R^2_m$ | $R^3$ | $R^4$ | $R^5$ | Data |
|---|---|---|---|---|---|
| | | | | | 696, 776, 979, 1002, 1036, 1069, 1092, 1445, 1524, 1676, 2920, 3330, 3400 |
| I.87 | H | $CH_3$ | $C_6H_5$ | 3-$CF_3$-Benzyl | oil, IR [$cm^{-1}$] (Film) 979, 1003, 1036, 1074, 1125, 1166, 1201, 1330, 1525, 1676, 2920, 3330 |
| I.88 | H | $CH_3$ | $C_6H_5$ | 4-Chlorophenyl | m.p. 58–62° C. |
| I.89 | H | $CH_3$ | $C_6H_5$ | 3,4-Dichloro-benzyl | oil, IR [$cm^{-1}$] (Film) 693, 880, 919, 979, 1002, 1035, 1445, 1471, 1525, 1676, 2930, 3340, 3420 |
| I.90 | H | $CH_3$ | $CH_3$ | 2-Methoxy-eth-1-yl | oil; IR [$cm^{-1}$] (Film) 891, 919, 980, 1038, 1093, 1127, 1366, 1525, 1673, 2870, 2937, 3340 |
| I.91 | H | $CH_3$ | 4-Cl—$C_6H_4$ | $CH_3$ | oil; IR [$cm^{-1}$] (Film) 875, 894, 979, 1012, 1037, 1091, 1491, 1525, 1674, 2890, 2938, 3340 |
| I.92 | H | $CH_3$ | 4-Cl—$C_6H_4$ | $C_2H_5$ | oil; IR [$cm^{-1}$] (Film) 924, 979, 1012, 1037, 1091, 1491, 1526, 1673, 2938, 2976, 3340 |
| I.93 | H | $CH_3$ | 4-Cl—$C_6H_4$ | n-$C_3H_7$ | oil; IR [$cm^{-1}$] (Film) 979, 1012, 1038, 1067, 1092, 1491, 1525, 1675, 2937, 2967, 3340 |
| I.94 | H | $CH_3$ | 4-Cl—$C_6H_4$ | i-$C_3H_7$ | oil; IR [$cm^{-1}$] (Film) 977, 1016, 1038, 1091, 1121, 1370, 1490, 1525, 1675, 2930, 2975, 3340 |
| I.95 | H | $CH_3$ | 4-Cl—$C_6H_4$ | n-$C_4H_9$ | oil; IR [$cm^{-1}$] (Film) 979, 1012, 1037, 1070, 1091, 1491, 1525, 1674, 2936, 2959, 3330 |
| I.96 | H | $CH_3$ | 4-Cl—$C_6H_4$ | t-$C_4H_9$ | m.p.: 67–71° C. |
| I.97 | H | $CH_3$ | 4-Cl—$C_6H_4$ | n-$C_6H_{13}$ | oil; IR [$cm^{-1}$] (Film) 979, 1011, 1038, 1091, 1491, 1525, 1675, 2872, 2934, 2954, 3330 |
| I.98 | H | $CH_3$ | 4-Cl—$C_6H_4$ | 3-Methyl-but-2-en-1-yl | oil; IR [$cm^{-1}$] (Film) 833, 878, 979, 1038, 1091, 1447, 1491, 1525, 1675, 2937, 3330 |
| I.99 | H | $CH_3$ | 4-Cl—$C_6H_4$ | Propargyl | m.p.: 109–114° C. |
| I.100 | H | $CH_3$ | 4-F—$C_6H_4$ | $CH_3$ | m.p.: 130–132° C. |
| I.101 | H | $CH_3$ | 4-F—$C_6H_4$ | $C_2H_5$ | m.p.: 105–110° C. |
| I.102 | H | $CH_3$ | 4-F—$C_6H_4$ | n-$C_3H_7$ | oil; IR [$cm^{-1}$] (Film) 840, 979, 1038, 1223, 1508, 1523, 1605, 1673, 2937, 2967, 3360 |
| I.103 | H | $CH_3$ | 4-F—$C_6H_4$ | i-$C_3H_7$ | oil; IR [$cm^{-1}$] (Film) |

TABLE I-continued

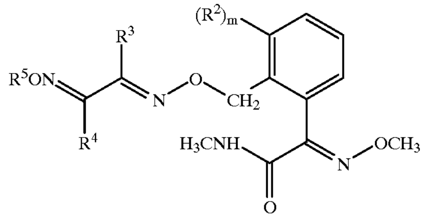

| No. | $R^2_m$ | $R^3$ | $R^4$ | $R^5$ | Data |
|---|---|---|---|---|---|
| | | | | | 840, 978, 1038, 1122, 1158, 1224, 1509, 1525, 1675, 2930, 2975, 3340 |
| I.104 | H | $CH_3$ | 4-F—$C_6H_4$ | t-$C_4H_9$ | m.p.: 95–100° C. |
| I.105 | H | $CH_3$ | 4-F—$C_6H_4$ | n-$C_4H_9$ | oil; IR [$cm^{-1}$] (Film) 840, 979, 1013, 1037, 1224, 1509, 1524, 1675, 2936, 2959, 3340 |
| I.106 | H | $CH_3$ | 4-F—$C_6H_4$ | n-$C_6H_{13}$ | oil; IR [$cm^{-1}$] (Film) 840, 979, 1011, 1038, 1225, 1509, 1524, 1605, 1676, 2935, 3340 |
| I.107 | H | $CH_3$ | 4-F—$C_6H_4$ | 3-Methyl-but-2-en-1-yl | oil; IR [$cm^{-1}$] (Film) 841, 980, 1038, 1159, 1224, 1509, 1525, 1605, 1675, 2938, 3350 |
| I.108 | H | $CH_3$ | 4-F—$C_6H_4$ | Propargyl | oil; IR [$cm^{-1}$] (Film) 841, 875, 980, 1005, 1035, 1222, 1509, 1525, 1602, 1674, 2110, 2930, 3250, 3340 |
| I.109 | H | $CH_3$ | 4-Cl—$C_6H_4$ | 3-iso-Propyl-1,2,4-oxadiazol-5-yl)-methyl | oil; IR [$cm^{-1}$] (Film) 874, 980, 1011, 1038, 1092, 1491, 1525, 1588, 1676, 2940, 2973, 3350 |
| I.110 | H | $CH_3$ | 4-Cl—$C_6H_4$ | Thiazol-4-yl-methyl | m.p.: 46–48° C. |
| I.111 | H | $CH_3$ | 4-Cl—$C_6H_4$ | (3-iso-Propyl-isoxazol-5-yl)-methyl | oil; IR [$cm^{-1}$] (Film) 981, 999, 1013, 1036, 1092, 1491, 1526, 1675, 2938, 2968, 3340 |
| I.112 | H | $CH_3$ | 4-Cl—$C_6H_4$ | (3-Bromo-isoxazo 1-5-yl)-methyl | m.p.: 46–49° C. |
| I.113 | H | $CH_3$ | 4-Cl—$C_6H_4$ | (3-$CF_3$-isoxazol-5-yl)-methyl | oil; IR [$cm^{-1}$] (Film) 970, 980, 999, 1013, 1036, 1092, 1155, 1190, 1491, 1671, 2940, 3340 |
| I.114 | H | $CH_3$ | 3-Cl—$C_6H_4$ | $CH_3$ | m.p.: 117–120° C. |
| I.115 | H | $CH_3$ | $C_2H_5$ | $CH_3$ | m.p.: 74–77° C. |
| I.116 | H | $CH_3$ | $C_2H_5$ | $C_2H_5$ | oil; IR [$cm^{-1}$] (Film) 768, 926, 960, 975, 1021, 1041, 1053, 1654, 1671, 2970, 3296 |
| I.117 | H | $CH_3$ | 4-$CH_3$—$C_6H_4$ | $CH_3$ | oil; IR [$cm^{-1}$] (Film) 980, 1006, 1037, 1092, 1447, 1461, 1528, 1669, 2939, 3349 |
| I.118 | H | $CH_3$ | 4-$CH_3$—$C_6H_4$ | $C_2H_5$ | oil; IR [$cm^{-1}$] (Film) 923, 954, 980, 1037, 1091, 1447, 1528, 1669, 2938, 2976, 3340 |
| I.119 | H | $CH_3$ | 4-$CH_3$—$C_6H_4$ | n-$C_3H_7$ | oil; IR [$cm^{-1}$] (Film) 911, 979, 1039, 1067, 1092, 1458, 1525, |

TABLE I-continued

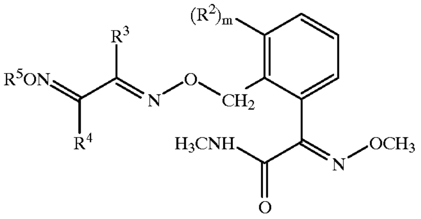

| No. | $R^2{}_m$ | $R^3$ | $R^4$ | $R^5$ | Data |
|---|---|---|---|---|---|
| | | | | | 1673, 2936, 2965, 3340 |
| I.120 | H | $CH_3$ | 3-Cl—$C_6H_4$ | $C_2H_5$ | oil; IR [$cm^{-1}$] (Film) 924, 979, 1012, 1037, 1091, 1411, 1525, 1673, 2937, 2976, 3350 |
| I.121 | H | $CH_3$ | 3-Cl—$C_6H_4$ | n-$C_3H_7$ | oil; IR [$cm^{-1}$] (Film) 917, 980, 1038, 1067, 1093, 1411, 1525, 1673, 2937, 2966, 3340 |
| I.122 | H | $CH_3$ | 3-Cl—$C_6H_4$ | i-$C_3H_7$ | oil; IR [$cm^{-1}$] (Film) 979, 1038, 1093, 1121, 1370, 1412, 1526, 1673, 2937, 2975, 3340 |
| I.123 | H | $CH_3$ | 3-Cl—$C_6H_4$ | n-$C_4H_9$ | oil; IR [$cm^{-1}$] (Film) 882, 979, 1037, 1071, 1092, 1412, 1525, 1674, 2936, 2959, 3350 |
| I.124 | H | $CH_3$ | 3-Cl—$C_6H_4$ | 3-Chloro-prop-2-en-1-yl | oil; IR [$cm^{-1}$] (Film) 789, 880, 932, 980, 1006, 1037, 1092, 1412, 1525, 1675, 2930, 3420 |
| I.125 | H | $CH_3$ | 3-Cl—$C_6H_4$ | Propargyl | oil; IR [$cm^{-1}$] (Film) 695, 885, 927, 980, 1006, 1035, 1092, 1412, 1525, 1674, 2110, 2930, 3290 |
| I.126 | H | $CH_3$ | 2-Cl—$C_6H_4$ | $CH_3$ | m.p.: 160–162° C. |
| I.127 | H | $CH_3$ | 2-Cl—$C_6H_4$ | $C_2H_5$ | m.p.: 125–127° C. |
| I.128 | H | $CH_3$ | 2-Cl—$C_6H_4$ | n-$C_3H_7$ | m.p.: 102–103° C. |
| I.129 | H | $CH_3$ | 3-$CH_3$-isox-azol-5-yl | $CH_3$ | oil; IR [$cm^{-1}$] (Film) 3345, 2940, 1675, 1526, 1446, 1412, 1068, 1038, 979, 959, 897 |
| I.130 | H | $CH_3$ | 3-$CH_3$-isox-azol-5-yl | $C_2H_5$ | oil; IR [$cm^{-1}$] (Film) 3340, 2939, 1675, 1526, 1446, 1412, 1091, 1037, 980, 957, 921 |
| I.131 | H | $CH_3$ | 3-$CH_3$-isox-azol-5-yl | n-$C_3H_7$ | oil; IR [$cm^{-1}$] (Film) 3350, 2938, 1675, 1526, 1447, 1412, 1068, 1037, 1011, 980, 960 |
| I.132 | H | $CH_3$ | 3-$CH_3$-isox-azol-5-yl | i-$C_3H_7$ | oil; IR [$cm^{-1}$] (Film) 3345, 2977, 2938, 1675, 1527, 1412, 1371, 1119, 1037, 982, 949 |
| I.133 | H | $CH_3$ | 3-$CH_3$-isox-azol-5-yl | n-$C_4H_9$ | oil; IR [$cm^{-1}$] (Film) 3340, 2959, 2937, 1676, 1526, 1447, 1412, 1071, 1036, 980, 951 |
| I.134 | H | $CH_3$ | 3-$CH_3$-isox-azol-5-yl | n-$C_6H_{13}$ | oil; IR [$cm^{-1}$] (Film) 3340, 2935, 1676, 1526, 1447, 1412, 1092, 1037, 1016, 980, 958 |

TABLE I-continued

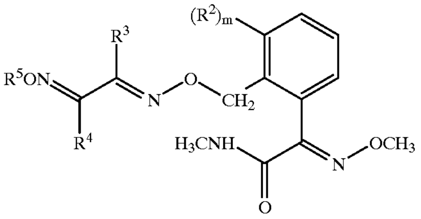

| No. | $R^2_m$ | $R^3$ | $R^4$ | $R^5$ | Data |
|---|---|---|---|---|---|
| I.135 | H | $CH_3$ | 3-$CH_3$-isox-azol-5-yl | Prop-1-en-3-yl | oil; IR [$cm^{-1}$] (Film) 3345, 2935, 1675, 1527, 1446, 1413, 1092, 1036, 1014, 981, 942, 919 |
| I.136 | H | $CH_3$ | 3-$CH_3$-isox-azol-5-yl | (E)-1-Chloro-prop-1-en-3-yl | oil; IR [$cm^{-1}$] (Film) 3340, 2938, 1674, 1527, 1446, 1412, 1092, 1036, 1014, 981, 949 |
| I.137 | Cl | $CH_3$ | $CH_3$ | $CH_3$ | m.p.: 120–122° C. |
| I.138 | Cl | $CH_3$ | $C_6H_5$ | $CH_3$ | m.p.: 190–192° C. |
| I.139 | Cl | $CH_3$ | $C_6H_5$ | $C_2H_5$ | oil; IR [$cm^{-1}$] (Film) 1039, 1444, 1528, 1676, 2038, 3350 |
| I.140 | H | $SCH_3$ | $CH_3$ | $CH_3$ | oil; IR [$cm^{-1}$] (Film) 3340, 1671, 1526, 1094, 1074, 1039, 1014, 980, 957, 877 |
| I.141 | H | $SCH_3$ | $CH_3$ | $C_2H_5$ | oil; IR [$cm^{-1}$] (Film) 3335, 2936, 1672, 1526, 1442, 1411, 1365, 1092, 1039, 981, 884 |
| I.142 | H | $SCH_3$ | $CH_3$ | n-$C_3H_7$ | oil; IR [$cm^{-1}$] (Film) 3340, 2965, 2936, 1672, 1526, 1365, 1094, 1064, 1037, 981, 960 |
| I.143 | H | $SCH_3$ | $CH_3$ | i-$C_3H_7$ | oil; IR [$cm^{-1}$] (Film) 3340, 2958, 2935, 2871, 1672, 1526, 1436, 1365, 1093, 1037, 980 |
| I.144 | H | $SCH_3$ | $CH_3$ | n-$C_6H_{13}$ | oil; IR [$cm^{-1}$] (Film) 3340, 2954, 2933, 28712 1672, 1526, 1436, 1365, 1093, 1037, 980 |
| I.145 | H | $SCH_3$ | $CH_3$ | Prop-1-en-3-yl | oil; IR [$cm^{-1}$] (Film) 3340, 2935, 1672, 1526, 1412, 1094, 1036, 980, 959, 923, 871 |
| I.146 | H | $SCH_3$ | $CH_3$ | 3-$CF_3$—$C_6H_4$—$CH_2$ | oil; IR [$cm^{-1}$] (Film) 3340, 2930, 1673, 1528, 1330, 1165, 1125, 1098, 1074, 1038, 982 |
| I.147 | H | $CH_3$ | 3-Pyridyl | $CH_3$ | oil; IR [$cm^{-1}$] (Film) 3340, 2939, 1672, 1526, 1412, 1071, 1038, 1005, 979, 896, 873 |

TABLE II

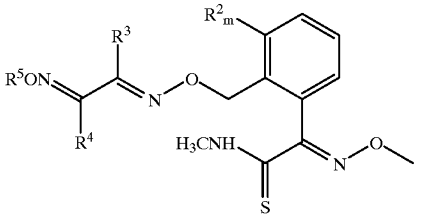

| No. | $R^2_m$ | $R^3$ | $R^4$ | $R^5$ | Data |
|---|---|---|---|---|---|
| II.01 | H | $CH_3$ | p-$OCH_3$—$C_6H_4$ | $CH_3$ | oil, IR [$cm^{-1}$] (Film) 834, 977, 1027, 1065, 1175, 1251, 1358, 1512, 1175, 1608, 2936, 3330 |
| II.02 | H | $CH_3$ | p-$OCH_3$—$C_6H_4$ | n-$C_3H_7$ | oil; IR [$cm^{-1}$] (Film) 977, 1027, 1066, 1176, 1251, 1358, 1512, 1607, 2935, 2964, 3340 |
| II.03 | H | $CH_3$ | p-$OCH_3$—$C_6H_4$ | n-$C_4H_9$ | oil, IR [$cm^{-1}$] (Film) 834, 975, 1027, 1175, 1252, 1359, 1512, 1607, 2934, 2957, 3340 |
| II.04 | H | $CH_3$ | $C_6H_5$ | 3-Fluoro-benzyl | m.p. 142–150° C. |
| II.05 | H | $CH_3$ | $C_6H_5$ | 3-$CF_3$-benzyl | oil, IR [$cm^{-1}$] (Film) 701, 1027, 1073, 1100, 1125, 1166, 1201, 1329, 1361, 1519, 2920, 3340 |
| II.06 | H | $CH_3$ | $C_6H_5$ | 3,4-Dichloro-benzyl | oil, IR [$cm^{-1}$] (Film) 694, 769, 877, 893, 975, 1028, 1357, 1471, 1519, 2935, 3340 |
| II.07 | H | $CH_3$ | $C_6H_5$ | 4-Chloro-phenyl | m.p. 55–60° C. |
| II.08 | H | $CH_3$ | $C_6H_5$ | 3-Bromobenzyl | oil, IR [$cm^{-1}$] (Film) 696, 773, 876, 893, 975, 1028, 1064, 1358, 1519, 2935, 3350 |
| II.09 | H | $CH_3$ | 4-Cl—$C_6H_4$ | i-$C_3H_7$ | oil, IR [$cm^{-1}$] (Film) 942, 974, 1027, 1091, 1121, 1358, 1369, 1490, 1518, 2920, 2975, 3350 |
| II.10 | H | $CH_3$ | 4-Cl—$C_6H_4$ | n-$C_4H_9$ | oil, IR [$cm^{-1}$] (Film) 830, 976, 1027, 1091, 1358, 1490, 1518, 2934, 2958, 3350 |
| II.11 | H | $CH_3$ | 4-Cl—$C_6H_4$ | t-$C_4H_9$ | oil, IR [$cm^{-1}$] (Film) 894, 973, 1030, 1089, 1188, 1364, 1490, 1519, 2934, 2977, 3350 |
| II.12 | H | $CH_3$ | 4-Cl—$C_6H_4$ | n-$C_6H_{13}$ | oil, IR [$cm^{-1}$] (Film) 830, 977, 1027, 1091, 1357, 1490, 1518, 2871, 2932, 2954, 3350 |
| II.13 | H | $CH_3$ | 4-F—$C_6H_4$ | $C_2H_5$ | oil, IR [$cm^{-1}$] (Film) 841, 976, 1027, 1058, 1225, 1358, 1509, 2936, 2970, 3360 |
| II.14 | H | $CH_3$ | 4-F—$C_6H_4$ | n-$C_3H_7$ | oil, IR [$cm^{-1}$] (Film) 840, 978, 1027, 1065, 1225, 1359, 1508, 1604, 2936, 2966, 3360 |
| II.15 | H | $CH_3$ | 4-F—$C_6H_4$ | t-$C_4H_9$ | m.p.: 113–119° C. |

Examples of the Action Against Harmful Fungi

It was possible to show the fungicidal action of the compounds of the general formula I by the following tests:

The active compounds were prepared as a 20% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and correspondingly diluted to the desired concentration with water.

1. Erysiphe graminis var. tritici

Leaves of wheat seedlings (Kanzler variety) were first treated with the aqueous preparation of the active compounds (containing 250 ppm). After about 24 h, the plants were dusted with spores of powdery mildew of wheat (Erysiphe graminis var. tritici). The plants treated in this way were then incubated for 7 days at 20–22° C. and a relative atmospheric humidity of 75–80%. The extent of fungal development was then determined.

In this test, the plants treated with the compounds according to the invention showed an attack of 5% or less, the plants treated with a known active compound (compound No. 195, Table 3, EP-A 463 488) showed 25% attack and the untreated plants showed 70% attack.

In a corresponding test (wheat seedlings of the Kanzler variety, application rate 250 ppm), the plants were first infected and incubated and then treated with the active compounds. In this test, the plants treated with the compounds according to the invention showed an attack of 5% or less and the untreated plants showed 60% attack.

Examples of the Action Against Animal Pests

It was possible to show the insecticidal action of the compounds of the general formula I by the following tests:

The active compounds were prepared a) as a 0.1% strength solution in acetone or b) as a 10% strength emulsion in a mixture of 70% by weight of cyclohexanol, 20% by weight of Nekanil® LN (Lutensol® AP6, wetting agent having emulsifying and dispersant action based on ethoxylated alkylphenols) and 10% by weight of Emulphor® EL (Emluan® EL, emulsifier based on ethoxylated fatty alcohols)

and correspondingly diluted to the desired concentration with acetone in the case of a) or with water in the case of b).

After termination of the tests, in each case the lowest concentration was determined at which the compounds still caused an 80–100% inhibition or mortality in comparison to untreated control tests (action threshold or minimum concentration).

*Aphis fabae* (Black Fly), Contact Action

Heavily infested dwarf beans (*Vicia faba*) were treated with the aqueous active compound preparation. The mortality rate was determined after 24 h.

In this test, the compounds I.68, I.69, I.70, I.71, I.81, I.86, I.94, I.97, I.103, I.105, I.106, II.12 and II.13 according to the invention showed action thresholds of 400 ppm or less.

*Nephotettix cincticeps* (Green Rice Leaf Hopper), Contact Action

Circular filters were treated with the aqueous active compound preparation and then occupied by 5 adult leaf hoppers. The mortality was assessed after 24 h.

In this test, the compounds I.02, I.04, I.10, I.17, I.24, I.29, I.46, I.47, I.48, I.52, I.55, I.74, I.75, I.78, I.79 and I.92 according to the invention showed action thresholds of 0.4 mg or less.

*Prodenia litura* (Egyptian Cotton Leaf Worm), Contact Action

Filters treated with the aqueous active compound preparation were occupied by 5 caterpillars. The first assessment is carried out after 4 h. If at least one caterpillar is still living, a feed mixture is added. The mortality was determined after 24 h.

In this test, the compounds I.04, I.17, I.78, I.79, I.91, I.92, I.94, I.101, I.102, I.103 and I.108 according to the invention showed action thresholds of 0.4 mg or less.

*Tetranychus telarius* (Common Red Spider Mite), Contact Action

Potted dwarf beans having the second successive pair of leaves were treated with aqueous active compound preparation. After 24 h, the plants were infected using heavily infested pieces of leaf. The attack was determined after 12 days in the greenhouse.

In this test, the compounds I.37, I.91, I.92, I.93, I.97, I.101, I.102, I.104, I.105, I.106, I.108, II.13, II.14 and II.15 showed action thresholds of 400 ppm or less.

We claim:

1. A phenylacetic acid compound of the formula I (I)

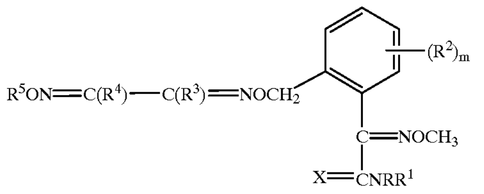

wherein m and the substituents have the following meanings:

X is oxygen or sulfur;

R is hydrogen or $C_1$–$C_4$-alkyl;

$R^1$ is hydrogen or $C_1$–$C_4$-alkyl;

$R^2$ is cyano, nitro, trifluoromethyl, halogen, $C_1$–$C_4$-alkyl or $C_1$–$C_4$-alkoxy;

m is 0, 1 or 2, it being possible for the $R^2$ radicals to be different if m is 2;

$R^3$ is hydrogen, cyano, nitro, hydroxyl, amino, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino or di-$C_1$–$C_4$-alkylamino;

$R^4$ is a heteroaryl radical selected from the group consisting of a 5-membered heteroaryl radical containing, in addition to carbon ring members, one to four nitrogen atoms, or one to three nitrogen atoms and a sulfur or an oxygen atom, or an oxygen atom, as ring members, a benzofused 5-membered heteroaryl radical wherein the 5-membered ring contains, in addition to carbon ring members, one to three nitrogen atoms, or one oxygen or sulfur atom, or one nitrogen atom and one oxygen or sulfur atom, as ring members, a 6-membered heteroaryl radical containing, in addition to carbon ring members, one to four nitrogen atoms as ring members, and a benzofused 6-membered heteroaryl radical, wherein the 6-membered ring contains, in addition to carbon ring members, one to four nitrogen atoms as ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy;

$R^5$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkoxy, heterocyclyl, heterocyclyloxy, benzyl, benzyloxy, aryl, aryloxy, arylthio, heteroaryl, hetaryloxy and hetarylthio, it being possible for the cyclic groups in turn to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, hetaryloxy, hetarylthio or $C(=NOR^6)—A_n—R^7$;

aryl, arylcarbonyl, arylsulfonyl, heteroaryl, hetarylcarbonyl or hetarylsulfonyl, it being possible for these radicals to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl, hetaryloxy or $C(=NOR^6)—A_n—R^7$; where A is oxygen, sulfur or nitrogen and where the nitrogen carries hydrogen or $C_1$–$C_6$-alkyl;

n is 0 or 1;

$R^6$ is hydrogen or $C_1$–$C_6$-alkyl and $R^7$ is hydrogen or $C_1$–$C_6$-alkyl, or its salt.

2. The compound of the formula I defined in claim 1, wherein $R^3$ is hydrogen, hydroxyl, cyclopropyl, halogen, $C_1$–$C_4$-alkyl, $C_1$–$C_4$-alkoxy or $C_1$–$C_4$-alkylthio, and $R^5$ is hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these groups to be partly or completely halogenated or to carry one to 3 of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, hetaryloxy and hetarylthio, it being possible for the aromatic and heteroaromatic radicals, in turn, to be partly or completely halogenated and/or to carry one to three of the following groups: cyano, nitro, hydroxyl, mercapto, amino, carboxyl, aminocarbonyl, halogen, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, hetaryloxy, hetarylthio or $C(=NOR^6)—A_n—R^7$;

aryl, heteroaryl, arylcarbonyl, hetarylcarbonyl, arylsulfonyl or hetarylsulfonyl, it being possible for these groups to be partly or completely halogenated or to carry one to 3 of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl, hetaryloxy or $C(=NOR^6)—A_n—R^7$; where A is oxygen, sulfur or nitrogen and where the nitrogen carries hydrogen or $C_1$–$C_6$-alkyl;

n is 0 or 1;

$R^6$ is hydrogen or $C_1$–$C_6$-alkyl and $R^7$ is hydrogen or $C_1$–$C_6$-alkyl, or its salt.

3. The compound of the formula I defined in claim 1, in which m is 0.

4. The compound of the formula I defined in claim 1, in which $R^1$ is methyl.

5. A composition against animal pests or harmful fungi, containing customary additives and an effective amount of a compound of the formula I defined in claim 1.

6. A method for controlling animal pests or harmful fungi, which comprises treating the pests or harmful fungi, their environment or the plants, surfaces, materials or spaces to be kept free from them with an effective amount of a compound of the formula I defined in claim 1.

7. A compound of the formula VIII (VIII)

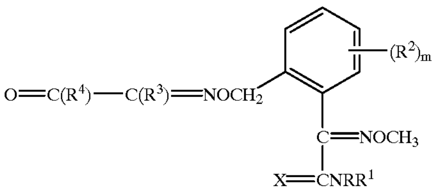

wherein m and the substituents have the following meanings:

X is oxygen or sulfur;

R is hydrogen or $C_1$–$C_4$-alkyl;

$R^1$ is hydrogen or $C_1$–$C_4$-alkyl;

$R^2$ is cyano, nitro, trifluoromethyl, halogen, $C_1$–$C_4$-alkyl or $C_1$–$C_4$-alkoxy;

m is 0, 1 or 2, it being possible for the $R^2$ radicals to be different if m is 2;

$R^3$ is hydrogen, cyano, nitro, hydroxyl, amino, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino or di-$C_1$–$C_4$-alkylamino;

$R^4$ is a heteroaryl radical selected from the group consisting of a 5-membered heteroaryl radical containing, in addition to carbon ring members, one to four nitrogen atoms, or one to three nitrogen atoms and a sulfur or an oxygen atom, as ring members, a benzofused 5-membered heteroaryl radical wherein the 5-membered ring contains, in addition to carbon ring members, one to three nitrogen atoms, or one nitrogen atom and one oxygen or sulfur atom, as ring members, a 6-membered heteroaryl radical containing, in addition to carbon ring members, one to four nitrogen atoms as ring members, and a benzofused 6-membered heteroaryl radical, wherein the 6-membered ring contains, in addition to carbon ring members, one to four nitrogen atoms as ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

8. The compound of the formula I defined in claim 2, wherein $R^4$ is a heteroaryl radical selected from the group consisting of a 5-membered heteroaryl radical containing, in addition to carbon ring members, one to four nitrogen atoms, or one to three nitrogen atoms and a sulfur or an oxygen atom, or an oxygen atom, as ring members, a benzofused 5-membered heteroaryl radical wherein the 5-membered ring contains, in addition to carbon ring members, one to three nitrogen atoms, or one oxygen or sulfur atom, or one nitrogen atom and one oxygen or sulfur atom, as ring members, a 6-membered heteroaryl radical containing, in addition to carbon ring members, one to four nitrogen atoms as ring members, and a benzofused 6-membered heteroaryl radical, wherein the 6-membered ring contains, in addition to carbon ring members, one to four nitrogen atoms as ring members, it being possible for these groups to be partly or completely halogenated or to carry one to 3 of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

9. The compound of the formula I defined in claim 1, wherein $R^4$ is a heteroaryl radical selected from the group consisting of a 5-membered heteroaryl radical containing, in addition to carbon ring members, one to four nitrogen atoms, or one to three nitrogen atoms and a sulfur or an oxygen atom, as ring members, a benzofused 5-membered heteroaryl radical wherein the 5-membered ring contains, in addition to carbon ring members, one to three nitrogen atoms, or one nitrogen atom and one oxygen or sulfur atom, as ring members, a 6-membered heteroaryl radical containing, in addition to carbon ring members, one to four nitrogen atoms as ring members, and a benzofused 6-membered heteroaryl radical, wherein the 6-membered ring contains, in addition to carbon ring members, one to four nitrogen atoms as ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

10. The compound of the formula I defined in claim 2, wherein $R^4$ is a heteroaryl radical selected from the group consisting of a 5-membered heteroaryl radical containing, in addition to carbon ring members, one to four nitrogen atoms, or one to three nitrogen atoms and a sulfur or an oxygen atom, as ring members, a benzofused 5-membered heteroaryl radical wherein the 5-membered ring contains, in addition to carbon ring members, one to three nitrogen atoms, or one nitrogen atom and one oxygen or sulfur atom, as ring members, a 6-membered heteroaryl radical containing, in addition to carbon ring members, one to four nitrogen atoms as ring members, and a benzofused 6-membered heteroaryl radical, wherein the 6-membered ring contains, in addition to carbon ring members, one to four nitrogen atoms as ring members, it being possible for these groups to be partly or completely halogenated or to carry one to 3 of the following groups:

cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

11. The compound of the formula I defined in claim 1, wherein $R^4$ is a heteroaryl radical selected from the group consisting of:

furyl, pyrrolyl, isoxazolyl, isothiazolyl, pyrazolyl, oxazolyl, thiazolyl, imidazolyl, oxadiazolyl, thiadiazolyl and triazolyl, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

12. The compound of the formula I defined in claim 1, wherein $R^4$ is a heteroaryl radical selected from the group consisting of:

pyrrolyl, isoxazolyl, isothiazolyl, pyrazolyl, oxazolyl, thiazolyl, imidazolyl, oxadiazolyl, thiadiazolyl and triazolyl, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

13. The compound of the formula I defined in claim 1, wherein $R^4$ is a benzofused heteroaryl radical which is selected from the group consisting of:

thienyl, furyl, pyrrolyl, isoxazolyl, isothiazolyl, oxazolyl and thiazolyl, wherein two adjacent carbon ring members or a nitrogen and an adjacent carbon ring member are bridged by a buta-1,3-diene-1,4-diyl group, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

14. The compound of the formula I defined in claim 1, wherein $R^4$ is a benzofused heteroaryl radical which is selected from the group consisting of:

pyrrolyl, isoxazolyl, isothiazolyl, oxazolyl and thiazolyl, wherein two adjacent carbon ring members or a nitrogen and an adjacent carbon ring member are bridged by a buta-1,3-diene-1,4-diyl group, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

15. The compound of the formula I defined in claim 1, wherein $R^4$ is a heteroaryl radical selected from the group consisting of:

pyridinyl, pyridazinyl, pyrimidinyl, pyrazinyl, triazinyl, tetrazinyl, and one of the foregoing heteroaryl rings in which two adjacent carbon ring members are bridged by a buta-1,3-diene-1,4-diyl group, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

16. The compound of the formula I defined in claim 1, wherein $R^4$ is a 5-membered or 6-membered heteroaryl radical containing, in addition to carbon ring members, one, two or three nitrogen atoms as ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

17. The compound of the formula I defined in claim 16, wherein the radical $R^4$ is bonded to the molecule through one of the nitrogen ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

18. The compound of the formula I defined in claim 1, wherein $R^4$ is a 5-membered heteroaryl radical containing, in addition to carbon ring members, one, two or three nitrogen atoms as ring members which is bonded to the molecule through one of the nitrogen ring members, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

19. The compound of the formula I defined in claim 1, wherein $R^4$ is a 5-membered heteroaryl radical selected from the group consisting of:

oxazolyl, thiazolyl, isoxazolyl, isothiazolyl, pyrazolyl and imidazolyl, it being possible for the heteroaryl radical to be partly or completely halogenated or to carry one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, heteroaryl and hetaryloxy.

20. The compound of the formula I defined in claim 1, wherein $R^3$ is methyl.

21. The compound of the formula I defined in claim 1, wherein $R^5$ is methyl or ethyl.

* * * * *